United States Patent [19]
Yoshimura et al.

[11] Patent Number: 5,692,027
[45] Date of Patent: Nov. 25, 1997

[54] RADIOGRAPHIC APPARATUS AND SUPPORTING DEVICE AND METHOD FOR THE SAME

[75] Inventors: Takahiro Yoshimura; Eiichi Arai; Kouichi Sonobe, all of Kyoto, Japan

[73] Assignee: J. Morita Manufacturing Corporation, Kyoto, Japan

[21] Appl. No.: 420,578

[22] Filed: Apr. 12, 1995

[30] Foreign Application Priority Data

Apr. 13, 1994 [JP] Japan .................... 6-075135
Mar. 29, 1995 [JP] Japan .................... 7-071944

[51] Int. Cl.$^6$ ........................................ A61B 6/14
[52] U.S. Cl. ............................... 378/38; 378/116
[58] Field of Search ..................... 378/38–40, 116

[56] References Cited

U.S. PATENT DOCUMENTS

| | | | |
|---|---|---|---|
| 4,160,906 | 7/1979 | Daniels et al. | 378/116 |
| 4,250,386 | 2/1981 | Pfeifer | 378/116 |
| 4,974,243 | 11/1990 | McArdle et al. | 378/38 |
| 5,093,852 | 3/1992 | Nishikawa et al. | 378/38 |

FOREIGN PATENT DOCUMENTS

| | | |
|---|---|---|
| 3609260A1 | 9/1987 | Germany. |
| 3937077A1 | 5/1990 | Germany. |

*Primary Examiner*—Craig E. Church
*Attorney, Agent, or Firm*—Koda & Androlia

[57] ABSTRACT

To enhance the controllability of input operation of radiographic conditions, allowing to select the desired radiographic mode easily out of multiple radiographic modes.

An operation panel 19 is provided in a patient frame 3 which incorporates a chin rest for holding the head of a patient, and this operation panel 19 comprises display means 63 for displaying the radiographic conditions, and input means 64 for entering the radiographic conditions. The input means 64 further comprises plural keys 52, 55 to 61, 66 to 69 for selecting radiographic modes, up and down cursor keys 70, 71 for selecting plural setting conditions corresponding to a selected radiographic mode, and left and right cursor keys 72, 73 for setting parameters of every setting condition. In a display unit 51 of the display means 63, there are display regions 130, 131, 132 for radiographic mode, setting conditions and parameters, respectively.

5 Claims, 38 Drawing Sheets

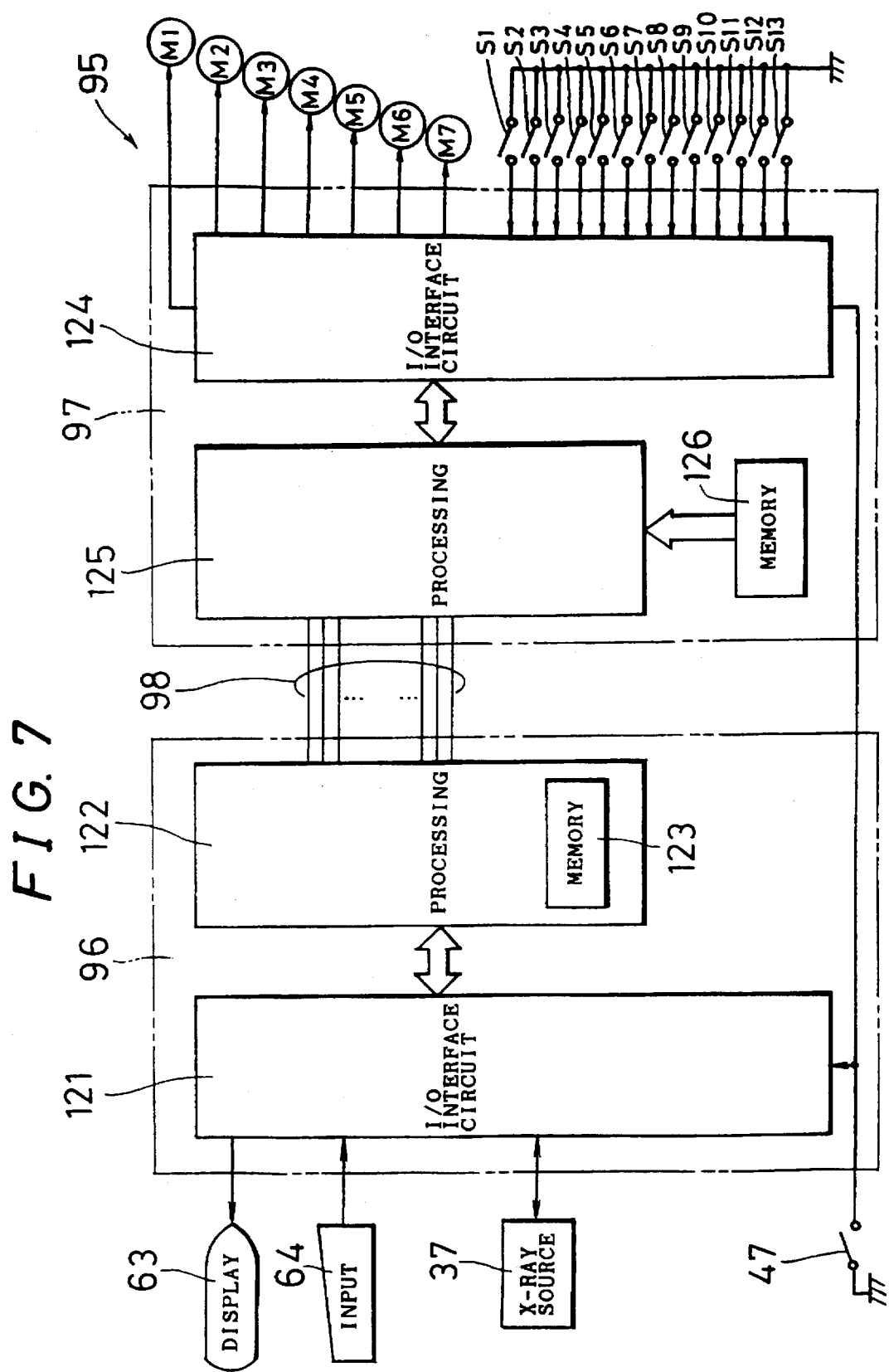

FIG. 16

| | |
|---|---|
| LOAD FILM CASSETTE 21 | b1 |
| MAKE SURE CHIN REST 17 IS AT LOWEST POSITION | b2 |
| MAKE SURE READY LAMP (GREEN) 45 IS LIT | b3 |
| CHANGE SLIT PLATE 22 TO NARROW GAP SLIT 91 | b4 |
| FIX PATIENT FRAME 3 | b5 |
| MATCH ARROW 134 OF ASCENDING/DESCENDING MAIN BODY 2 WITH VALUE 0 OF SCALE 135 OF PATIENT FRAME 3 | b6 |
| PATIENT IS SEATED ON CHAIR 6 | b7 |
| MOVE ASCENDING/DESCENDING MAIN BODY 2 TO ADJUST HEIGHT OF CHIN REST 17 TO JAW OF PATIENT | b8 |
| PATIENT HOLDS MOUTHPIECE IN HIS MOUTH | b9 |
| PATIENT IS INTRODUCED INTO RADIOGRAPHIC POSITION | b10 |
| RAISE CHIN REST 17 TO PUT JAW ON | b11 |
| MATCH MEDIAN LINE BEAM 34 | b12 |
| FIX PATIENT WITH JAW BONE PLATE | b13 |
| ADJUST EYE-EAR PLATE TO HORIZONTAL BEAM 33 | b14 |
| FIX PATIENT FRAME 3 | b15 |
| MOVE ASCENDING/DESCENDING MAIN BODY 2 TO ADJUST IRRADIATION BEAM TO NOSE WINGS | b16 |
| ADJUST POSITION SENSOR BEAM TO MOUTHPIECE CENTER, AND PRESS EDGE-TO-EDGE OCCLUSION KEYS 82-85 | b17 |
| MAKE SURE AGAIN READY LAMP (GREEN) 45 IS LIT | b18 |
| PRESS IRRADIATION BUTTON 47 TO START RADIOGRAPHY | b19 |
| RETURN SWIVEL ARM 1 TO HOME POSITION | b20 |
| UNLOAD FILM CASSETTE 21 | b21 |

FIG. 19

- DEVELOP PANORAMIC FILM — c1
- READ ON FILM — c2
- LOAD FILM CASSETTE 21 — c3
- MAKE SURE CHIN REST 17 IS AT LOWEST POSITION — c4
- MAKE SURE READY LAMP (GREEN) 45 IS LIT — c5
- CHANGE SLIT PLATE 22 TO BROAD SLIT 91 — c6
- MATCH ARROW 134 OF ASCENDING/DESCENDING MAIN BODY 2 WITH VALUE 0 OF SCALE 135 OF PATIENT FRAME 3 — c7
- REMOVE JAW BONE PLATE, AND REPLACE WITH EAR RODS 29, 30 — c8
- PATIENT IS SEATED ON CHAIR 6 — c9
- MOVE ASCENDING/DESCENDING MAIN BODY 2 TO ADJUST HEIGHT OF EAR RODS 29, 30 TO THE EAR HOLES OF PATIENT — c10
- PATIENT HOLDS MOUTHPIECE IN HIS MOUTH — c11
- PATIENT IS INTRODUCED INTO RADIOGRAPHIC POSITION — c12
- RAISE CHIN REST 17 TO PUT JAW ON — c13
- MATCH MEDIAN LINE BEAM 34 — c14
- FIX PATIENT BY INSERTING EAR RODS 29, 30 INTO EAR HOLES — c15
- ADJUST EYE-EAR PLANE OR CAMPER'S PLANE TO HORIZONTAL BEAM 33 — c16
- FIX PATIENT FRAME 3 — c17
- MOVE ASCENDING/DESCENDING MAIN BODY 2 TO ADJUST IRRADIATION BEAM TO CENTER OF EACH POSITION — c18
- ADJUST POSITION SENSOR BEAM TO MOUTHPIECE CENTER, AND PRESS EDGE-TO-EDGE OCCLUSION KEYS 82-85 — c19
- MAKE SURE AGAIN READY LAMP (GREEN) 45 IS LIT — c20
- PRESS IRRADIATION BUTTON 47 TO START RADIOGRAPHY — c21
- RETURN SWIVEL ARM 1 TO HOME POSITION — c22
- UNLOAD FILM CASSETTE 21 — c23

FIG. 22

- DEVELOP PANORAMIC FILM — d1
- READ ON FILM — d2
- LOAD FILM CASSETTE 21 — d3
- MAKE SURE CHIN REST 17 IS AT LOWEST POSITION — d4
- MAKE SURE READY LAMP (GREEN) 45 IS LIT — d5
- CHANGE SLIT PLATE 22 TO BROAD SLIT 91 — d6
- MATCH ARROW 134 OF ASCENDING/DESCENDING MAIN BODY 2 WITH VALUE 0 OF SCALE 135 OF PATIENT FRAME 3 — d7
- PATIENT IS SEATED ON CHAIR 6 — d8
- MOVE ASCENDING/DESCENDING MAIN BODY 2 TO ADJUST HEIGHT OF CHIN REST 17 TO JAW OF PATIENT — d9
- PATIENT HOLDS MOUTHPIECE IN HIS MOUTH — d10
- PATIENT IS INTRODUCED INTO RADIOGRAPHIC POSITION — d11
- RAISE CHIN REST 17 TO PUT JAW ON — d12
- MATCH MEDIAN LINE BEAM 34 — d13
- FIX PATIENT WITH JAW BONE PLATE — d14
- ADJUST EYE-EAR PLANE TO HORIZONTAL BEAM 33 — d15
- FIX PATIENT FRAME 3 — d16
- MOVE ASCENDING/DESCENDING MAIN BODY 2 TO ADJUST IRRADIATION BEAM TO CENTER OF EACH POSITION — d17
- ADJUST POSITION SENSOR BEAM TO MOUTHPIECE CENTER, AND PRESS EDGE-TO-EDGE OCCLUSION KEYS 82-85 — d18
- MAKE SURE AGAIN READY LAMP (GREEN) 45 IS LIT — d19
- PRESS IRRADIATION BUTTON 47 TO START RADIOGRAPHY — d20
- RETURN SWIVEL ARM 1 TO HOME POSITION — d21
- UNLOAD FILM CASSETTE 21 — d22

FIG. 28

| | |
|---|---|
| LOAD FILM CASSETTE 21 | e1 |
| MAKE SURE CHIN REST 17 IS AT LOWEST POSITION | e2 |
| MAKE SURE READY LAMP (GREEN) 45 IS LIT | e3 |
| CHANGE SLIT PLATE 22 TO BROAD SLIT 91 | e4 |
| MATCH ARROW 134 OF ASCENDING/DESCENDING MAIN BODY 2 WITH VALUE 0 OF SCALE 135 OF PATIENT FRAME 3 | e5 |
| REMOVE JAW BONE PLATE, AND REPLACE WITH EAR RODS 29, 30 | e6 |
| REMOVE CHIN REST 17, AND REPLACE WITH SUBNASAL POINT REST | e7 |
| PATIENT IS SEATED ON CHAIR 6 | e8 |
| MOVE ASCENDING/DESCENDING MAIN BODY 2 TO ADJUST HEIGHT OF EAR RODS 29, 30 TO EAR HOLES OF PATIENT | e9 |
| PATIENT IS INTRODUCED INTO RADIOGRAPHIC POSITION | e10 |
| ADJUST SUBNASAL POINT REST TO SUBNASAL POINT OF PATIENT | e11 |
| PATIENT OCCLUDES SPONTANEOUSLY | e12 |
| MATCH MEDIAN LINE BEAM 34 | e13 |
| FIX PATIENT BY INSERTING EAR RODS 29, 30 INTO EAR HOLES | e14 |
| ADJUST EYE-EAR PLANE TO HORIZONTAL BEAM 33 | e15 |
| FIX PATIENT FRAME 3 | e16 |
| MOVE ASCENDING/DESCENDING MAIN BODY 2 TO ADJUST IRRADIATION BEAM TO HIGHEST POSITION OF IRRADIATION FIELD | e17 |
| MAKE SURE AGAIN READY LAMP (GREEN) 45 IS LIT | e18 |
| PRESS IRRADIATION BUTTON 47 TO START RADIOGRAPHY | e19 |
| RETURN SWIVEL ARM 1 TO HOME POSITION | e20 |
| UNLOAD FILM CASSETTE 21 | e21 |

FIG. 32

| | |
|---|---|
| LOAD FILM CASSETTE 21 | f1 |
| MAKE SURE CHIN REST 17 IS AT LOWEST POSITION | f2 |
| MAKE SURE READY LAMP (GREEN) 45 IS LIT | f3 |
| CHANGE SLIT PLATE 22 TO NARROW GAP SLIT 90 | f4 |
| MATCH ARROW 134 OF ASCENDING/DESCENDING MAIN BODY 2 WITH VALUE 0 OF SCALE 135 OF PATIENT FRAME 3 | f5 |
| PATIENT IS SEATED ON CHAIR 6 | f6 |
| MOVE ASCENDING/DESCENDING MAIN BODY 2 TO ADJUST HEIGHT OF CHIN REST 17 TO JAW OF PATIENT | f7 |
| PATIENT HOLDS MOUTHPIECE IN HIS MOUTH | f8 |
| PATIENT IS INTRODUCED INTO RADIOGRAPHIC POSITION | f9 |
| RAISE CHIN REST 17 TO PUT JAW ON | f10 |
| MATCH MEDIAN LINE BEAM 34 | f11 |
| FIX PATIENT WITH JAW BONE PLATE | f12 |
| ADJUST EYE-EAR PLANE TO HORIZONTAL BEAM 33 | f13 |
| FIX PATIENT FRAME 3 | f14 |
| MOVE ASCENDING/DESCENDING MAIN BODY 2 TO ADJUST IRRADIATION BEAM TO NOSE WINGS | f15 |
| MATCH POSITION SENSOR BEAM TO CENTER OF MOUTHPIECE, AND PRESS EDGE-TO-EDGE OCCLUSION KEYS 82-85 | f16 |
| MAKE SURE AGAIN READY LAMP (GREEN) 45 IS LIT | f17 |
| PRESS IRRADIATION BUTTON 47 TO START RADIOGRAPHY | f18 |
| RETURN SWIVEL ARM 1 TO HOME POSITION | f19 |
| UNLOAD FILM CASSETTE 21 | f20 |

FIG. 35

| | |
|---|---|
| LOAD FILM CASSETTE 21 | g1 |
| MAKE SURE CHIN REST 17 IS AT LOWEST POSITION | g2 |
| MAKE SURE READY LAMP (GREEN) 45 IS LIT | g3 |
| CHANGE SLIT PLATE 22 TO NARROW GAP SLIT 90 | g4 |
| MATCH ARROW 134 OF ASCENDING/DESCENDING MAIN BODY 2 WITH VALUE 0 OF SCALE 135 OF PATIENT FRAME 3 | g5 |
| REMOVE JAW BONE PLATE, AND REPLACE WITH EAR RODS 29, 30 | g6 |
| REMOVE CHIN REST 17, AND REPLACE WITH SUBNASAL POINT REST | g7 |
| PATIENT IS SEATED ON CHAIR 6 | g8 |
| MOVE ASCENDING/DESCENDING MAIN BODY 2 TO ADJUST HEIGHT OF EAR RODS 29, 30 TO EAR HOLES OF PATIENT | g9 |
| PATIENT IS INTRODUCED INTO RADIOGRAPHIC POSITION | g10 |
| ADJUST SUBNASAL POINT REST TO SUBNASAL POINT OF PATIENT | g11 |
| PATIENT OCCLUDES SPONTANEOUSLY | g12 |
| MATCH MEDIAN LINE BEAM 34 | g13 |
| FIX PATIENT BY INSERTING EAR RODS 29, 30 INTO EAR HOLES | g14 |
| ADJUST EYE-EAR PLANE TO HORIZONTAL BEAM 33 | g15 |
| FIX PATIENT FRAME 3 | g16 |
| MOVE ASCENDING/DESCENDING MAIN BODY 2 TO ADJUST IRRADIATION BEAM TO HIGHEST POSITION OF IRRADIATION FIELD | g17 |
| PATIENT CLOSES MOUTH | g18 |
| MAKE SURE AGAIN READY LAMP (GREEN) 45 IS LIT | g19 |
| PRESS IRRADIATION BUTTON 47 TO START RADIOGRAPHY | g20 |
| PATIENT OPENS MOUTH | g21 |
| MAKE SURE AGAIN READY LAMP (GREEN) 45 IS LIT | g22 |
| PRESS IRRADIATION BUTTON 47 TO START RADIOGRAPHY | g23 |
| RETURN SWIVEL ARM 1 TO HOME POSITION | g24 |
| UNLOAD FILM CASSETTE 21 | g25 |

FIG. 37

| | |
|---|---|
| LOAD FILM CASSETTE 21 | h1 |
| MAKE SURE CHIN REST 17 IS AT LOWEST POSITION | h2 |
| MAKE SURE READY LAMP (GREEN) 45 (GREEN) 45 IS LIT | h3 |
| CHANGE SLIT PLATE 22 TO NARROW GAP SLIT 90 | h4 |
| MATCH ARROW 134 OF ASCENDING/DESCENDING MAIN BODY 2 WITH VALUE 0 OF SCALE 135 OF PATIENT FRAME 3 | h5 |
| REMOVE JAW BONE PLATE, AND REPLACE WITH EAR RODS 29, 30 | h6 |
| REMOVE CHIN REST 17, AND REPLACE WITH SUBNASAL POINT REST | h7 |
| PATIENT IS SEATED ON CHAIR 6 | h8 |
| MOVE ASCENDING/DESCENDING MAIN BODY 2 TO ADJUST HEIGHT OF EAR RODS 29, 30 TO EAR HOLES OF PATIENT | h9 |
| PATIENT IS INTRODUCED INTO RADIOGRAPHIC POSITION | h10 |
| ADJUST SUBNASAL POINT REST TO SUBNASAL POINT OF PATIENT | h11 |
| PATIENT OCCLUDES SPONTANEOUSLY | h12 |
| MATCH MEDIAN LINE BEAM 34 | h13 |
| FIX PATIENT BY INSERTING EAR RODS 29, 30 INTO EAR HOLES | h14 |
| ADJUST EYE-EAR PLANE TO HORIZONTAL BEAM 33 | h15 |
| FIX PATIENT FRAME 3 | h16 |
| MOVE ASCENDING/DESCENDING MAIN BODY 2 TO ADJUST IRRADIATION BEAM TO HIGHEST POSITION OF IRRADIATION FIELD | h17 |
| MAKE SURE AGAIN READY LAMP (GREEN) 45 IS LIT | h18 |
| PRESS IRRADIATION BUTTON 47 TO START RADIOGRAPHY | h19 |
| RETURN SWIVEL ARM 1 TO HOME POSITION | h20 |
| UNLOAD FILM CASSETTE 21 | h21 |

FIG. 40

| LOAD FILM CASSETTE 21 | i1 |
| MAKE SURE CHIN REST 17 IS AT LOWEST POSITION | i2 |
| MAKE SURE READY LAMP (GREEN) 45 IS LIT | i3 |
| CHANGE SLIT PLATE 22 TO NARROW GAP SLIT 90 | i4 |
| FIX PATIENT FRAME 3 | i5 |
| MATCH ARROW 134 OF ASCENDING/DESCENDING MAIN BODY 2 WITH VALUE 0 OF SCALE 135 OF PATIENT FRAME 3 | i6 |
| PATIENT IS SEATED ON CHAIR 6 | i7 |
| MOVE ASCENDING/DESCENDING MAIN BODY 2 TO ADJUST HEIGHT OF CHIN REST 17 TO JAW OF PATIENT | i8 |
| PATIENT IS INTRODUCED INTO RADIOGRAPHIC POSITION | i9 |
| RAISE CHIN REST 17 TO PUT JAW ON | i10 |
| MATCH MEDIAN LINE BEAM 34 | i11 |
| FIX PATIENT WITH JAW BONE PLATE | i12 |
| ADJUST EYE-EAR PLANE TO HORIZONTAL BEAM 33 | i13 |
| MAKE SURE IRRADIATION FIELD BEAM IS AT LOWER LIP LOWER EDGE | i14 |
| MAKE SURE AGAIN READY LAMP (GREEN) 45 IS LIT | i15 |
| PRESS IRRADIATION BUTTON 47 TO START RADIOGRAPHY | i16 |
| RETURN SWIVEL ARM 1 TO HOME POSITION | i17 |
| UNLOAD FILM CASSETTE 21 | i18 |

FIG. 45

- LOAD FILM CASSETTE 21 — j1
- MAKE SURE CHIN REST 17 IS AT LOWEST POSITION — j2
- MAKE SURE READY LAMP (GREEN) 45 IS LIT — j3
- CHANGE SLIT PLATE 22 TO BROAD SLIT 91 — j4
- MATCH ARROW 134 OF ASCENDING/DESCENDING MAIN BODY 2 WITH VALUE 0 OF SCALE 135 OF PATIENT FRAME 3 — j5
- REMOVE JAW BONE PLATE, AND REPLACE WITH EAR RODS 29, 30 — j6
- PATIENT IS SEATED ON CHAIR 6 — j7
- MOVE ASCENDING/DESCENDING MAIN BODY 2 TO ADJUST HEIGHT OF EAR RODS 29, 30 TO EAR HOLES OF PATIENT — j8
- PATIENT IS INTRODUCED INTO RADIOGRAPHIC POSITION — j9
- RAISE CHIN REST TO PUT JAW ON — j10
- PATIENT OCCLUDES SPONTANEOUSLY — j11
- MATCH MEDIAN LINE BEAM 34 — j12
- FIX PATIENT BY INSERTING EAR RODS 29, 30 INTO EAR HOLES — j13
- ADJUST EYE-EAR PLANE TO HORIZONTAL BEAM 33 — j14
- FIX PATIENT FRAME 3 — j15
- MOVE ASCENDING/DESCENDING MAIN BODY 2 TO ADJUST IRRADIATION BEAM TO HIGHEST POSITION OF IRRADIATION FIELD — j16
- MAKE SURE AGAIN READY LAMP (GREEN) 45 IS LIT — j17
- PRESS IRRADIATION BUTTON 47 TO START RADIOGRAPHY — j18
- RETURN SWIVEL ARM 1 TO HOME POSITION — j19
- UNLOAD FILM CASSETTE 21 — j20

RADIOGRAPHIC APPARATUS AND SUPPORTING DEVICE AND METHOD FOR THE SAME

BACKGROUND OF THE INVENTION

1. Field of the Invention

The present invention relates to a radiographic apparatus used in medical treatment and examination in the fields of dentistry, otorhinolaryngology and the like, and capable of radiographing the dentition, jaw bones, facial bones and others of patients, and to its supporting device and method.

2. Description of the Related Art

FIG. 50 is a side view showing the constitution of a conventional radiographic apparatus 100. FIG. 51 is a perspective view showing the constitution of other conventional radiographic apparatus 120. The radiographic apparatuses are similarly constituted except that the installation positions of an operation panel 119 are different, and therefore the same members are denoted by the same reference numerals.

The radiographic apparatuses 100, 120 are roughly composed of a swivel arm 101, an ascending/descending main body 102, a patient frame 103, a post 104, and a base 105.

The swivel arm 101 is formed approximately in an inverted U-shape, one end 101a of which is provided with an X-ray source, and a slit plate, and the other end 101b of which is provided with X-ray detecting means realized by including a film cassette, a slit plate, and a displacement driving mechanism for the film cassette.

The area in the middle 101c of the swivel arm 101 is suspended from a holding frame 108 through a swivel mechanism 107, and the holding frame 108 is extended from the ascending/descending main body 102. Swivel means for moving the swivel arm 101 along the dental arch is incorporated in the swivel mechanism 107. Therefore, the swivel mechanism 107 can be moved depending on the contour of the dental arch of a patient, so that panoramic radiograph and the like may be realized.

The ascending/descending main body 102 is constituted so as to be movable in the vertical direction along the post 104 standing up from the base 105. The post 104 is provided with guide rails 106 and others, via which the patient frame 103 is integratedly mounted to the ascending/descending main body 102 so as to be free to move up and down. Positioning of the patient frame 103 integrated with the ascending/descending main body 102 can be conducted by manipulating a lock handle 109, that is, by that brake means provided in the patient frame 103 or ascending/descending main body 102 acts on the post 104. A grip 118 is provided in the lower side of the patient frame 103, and by holding the grip 118, the position of the patient 112 may be fixed during radiographing, and as well the shoulders of the patient 112 are lowered, so that the movement of the swivel arm 101 is not disturbed.

A head holding device 114 for positioning and holding the head 113 of the patient 112 comprises a frontal holder 115 to be abutted against the forehead of the head 113 of the patient 112, a pair of temporal holders 116 to be abutted against both temporals of the head 113 of the patient 112, and a chin rest supporting member 117 having a chin rest 117a on which the lower jaw of the patient 112 is placed.

The frontal and temporal holders 115, 116 are installed downward from the middle portion 101c of the swivel arm 101. One temporal holder 116 holds the head 113 of the patient 112 together with the other temporal holder 116. The pair of temporal holders 116 are mounted in the middle portion 101c of the swivel arm 101 so that the distance therebetween may be adjustable.

The chin rest 117a is fixed on the patient frame 103 by the chin rest support member 117. The lower jaw of the patient 112 is placed on the chin rest 117a. The chin rest support member 117 is composed so as to be expandable from the patient frame 103 toward the patient 112.

The input operation of radiographic conditions of such radiographic apparatuses 100, 120 is effected through an operation panel 119. In the radiographic apparatus 100, the operation panel 119 is arranged at one side of the ascending/descending main body 102. In the other radiographic apparatus 120, the operation panel 119 is arranged at one end 101a of the swivel arm 101. The operation panel 119 is provided with a plurality of operation keys necessary for the input operation of the radiographic conditions.

The radiologist who manipulates the radiographic apparatuses 100, 120 positions the patient 112 to place in the optimum state at the specified radiographic position so as to obtain radiographs of the desired site. At this time, the radiologist, closely and obliquely before the patient 112, projects patient positioning light beams 123, 124 from patient positioning beam generators 121, 122 to the face of the patient 112, and positions the head 113 of the patient 112 with reference to the beams 123, 124.

In the radiographic apparatuses 100, 120, the operation panel 119 is arranged at one side of the ascending/descending main body 102 or at one end 101a of the swivel arm 101. That is, it is provided at a relatively remote position from the patient 112. Therefore, when the radiologist conducts the input operation of the radiographic conditions while positioning the patient 112, the radiologist has to observe a different direction from that of the patient 112, and as well has to enter the conditions one or two steps apart. Accordingly the operability is inferior.

In the conventional dental multi-function, multi-section tomographic apparatuses including the aforementioned radiographic apparatuses 100, 120, when the radiographic conditions are inputted, the following methods are employed in order to select a desired radiographic program from numerous radiographic programs. That is, (1) the radiographic programs are assigned with program numbers, and the radiologist searches a desired radiographic program with reference to the manual, code tables or the like, and enters the selected program number through input means such as numeric key pads to set the desired radiographic program, or (2) by using display means realized by a liquid crystal display device or the like incorporated in the radiographic apparatus and input means realized by a touch panel or the like, while sequentially observing the screen built up in hierarchical structure, the radiologist sequentially answers the questions shown on the screen to set all conditions for the desired radiographic program.

These methods have their own problems: in the case of (1), since the radiologist enters the radiographic program with reference to the manual, code tables or the like, it takes a long time to search the desired radiographic program, and the probability of operational error in inputting is relatively high, or in order to know the available modes in the radiographic apparatus, it is required to read through the manual or instruction book, which is time expendible. In the case of (2), because of the hierarchical structure of the radiographic program, if the radiologist makes an operational error in inputting, the data must be entered again from the beginning, and it is very inconvenient. Moreover, since the screen is updated every time when the data is entered while observing the screen, the previous input state cannot be reviewed any longer, and it is also very inconvenient.

SUMMARY OF THE INVENTION

It is hence a primary object of the invention to provide a radiographic apparatus capable of entering radiographic conditions with an excellent operability, and supporting device and method of the same.

To achieve the object, the invention provides a radiographic apparatus comprising:

a base, a post standing up on the base, an ascending/descending main body provided on the post so as to be free to move up and down, a swivel arm in which an X-ray source and detecting means for detecting X-rays radiated from the X-ray source are arranged so as to confront each Other, swivel and driving means for swiveling and driving the swivel arm alone a desired track, the swivel and driving means being interposed between the ascending/descending main body and the swivel arm, holding means for positioning and holding the head of a patient at a desired radiographic position between the X-ray source and the detecting means, a patient frame arranged in the ascending/descending main body, to which the holding means is attached, and an operation panel for setting radiographic conditions, arranged in the patient frame.

The radiographic apparatus of the invention is characterized in that the operation panel is disposed as being concentrated in the upper part of the patient frame.

The radiographic apparatus of the invention is characterized in that the operation panel comprises input means for entering input information for determining the radiographic conditions, and display means for displaying the information for aiding the input operation by the input means.

The radiographic apparatus of the invention is characterized in that the input means comprises selection means for selecting any one of a plurality of predetermined radiographic modes, means for selecting setting conditions of the radiographic mode selected by the radiographic mode selection means, and means for setting parameters of the setting conditions selected by the setting condition selection means, and the display means possesses a region for displaying the radiographic mode selected by the radiographic mode selection means, a region for displaying the setting conditions corresponding to the radiographic mode displayed in the radiographic mode display region, and a region for displaying parameters corresponding to the setting conditions displayed in the setting condition display means.

The radiographic apparatus of the invention is characterized in that the input means comprises a nonvolatile memory for storing the radiographic mode, setting conditions and parameters set by the radiograph mode selection means, setting condition selection means, and parameter setting means, respectively.

Further, the radiographic apparatus of the invention is characterized in that the display means possesses a region for schematically displaying the information related to radiography, including the radiographic position, projection angle, and tomographic mode, in figures and characters.

The invention further provides a support device for a radiographic apparatus, comprising:

selection means for selecting any one of a plurality of predetermined radiographic modes, selection means for selecting setting conditions of the radiographic mode selected by the radiographic mode selection means, setting means for setting parameters of the setting conditions selected by the setting condition selection means, and display means for displaying the radiographic mode selected by the radiographic mode selection means, setting conditions corresponding to the radiographic mode, and parameters corresponding to the setting conditions.

The support device for the radiographic apparatus of the invention comprises a nonvolatile memory for storing the radiographic mode, setting conditions and parameters set by the radiographic mode selection means, setting condition selection means, and parameter setting means, respectively.

The support device for the radiographic apparatus of the invention is characterized in that the display means possesses a region for schematically displaying the information related to radiography, including the radiographic position, projection angle, and tomograph mode, in figures and characters.

Further the support device for the radiographic apparatus of the invention is characterized in that the display means displays a plurality of tomographic position display lines showing the tomographic positions of the radiographic site, and that each tomographic position display line moves the radiographic site in response to the parameter set by the parameter setting means, and also varies the interval between the tomographic position display lines.

Further the support device for the radiographic apparatus of the invention is characterized in that the radiograph mode selection means is capable of selecting one radiographic mode out of a plurality of predetermined radiographic modes including at least panoramic radiography, jaw bone/dentition cross sectional tomography, dentition parallel tomography, maxillary sinus tomography, frontal direction temporomandibular joint tomography, temporomandibular temporal tomography, temporomandibular joint distance measuring purpose radiography, temporomandibular joint head angle measuring purpose radiography, maxillary sinus scanogram filming, temporomandibular joint scanogram filming, linear scanning radiography, and cephaloradiography.

The invention moreover provides a support method for a radiographic apparatus which possesses a swivel arm comprising an X-ray source and an X-ray detector disposed to confront the X-ray source, for positioning and holding the head of a patient at a predetermined radiographic position between the X-ray source and the X-ray detector, setting radiographic conditions via an operation panel, emitting X-rays from the X-ray source while driving the swivel arm along a predetermined track, and detecting the X-ray by the X-ray detector, the method comprising:

a first step of selecting any one of the plurality of predetermined radiographic modes, a second step of displaying the radiographic mode selected at the first step and a plurality of setting conditions relating to the radiograph mode, a third step of selecting the plurality of setting conditions displayed at the second step, a fourth step of setting the parameters of the setting conditions selected at the third step, and a fifth step of repeating the third and fourth steps until all parameters of the plurality of setting conditions are set.

The support method for the radiographic apparatus of the invention is characterized in that after finishing an arbitrary step of the first to the fifth step, the setting data up to the arbitrary step is stored.

Further the support method for the radiographic apparatus of the invention is characterized in that the second step is to display the information relating to the radiographic mode selected at the first step schematically in figures and characters, as well as to display the radiographic mode selected at the first step and a plurality of setting conditions relating to the radiographic mode.

According to the invention, the patient is positioned and held at a predetermined radiographic position between the X-ray source and detecting means for detecting the X-ray emitted from the X-ray source being disposed to confront each other, by holding means of the patient frame. The patient frame is attached so as to be free to move up and down, for example, to the ascending/descending main body which supports the swivel arm comprising the X-ray source and detecting means, and by moving the patient frame up or down, the patient can be held and fixed at the height depending on the height of the patient. Or, by moving the ascending/descending main body up or down, the swivel arm may be located depending on the height of the radiographic site.

When positioning and fixing the patient, the radiologist positions the patient, at the closest position to the patient beside the patient frame, while emitting beams to the patient, so as to be disposed in the optimum state at a desired radiographic position. The operation panel for input operation of radiographic conditions is disposed in the patient frame at a relatively close position to the patient, preferably in its upper part, so that the radiologist can enter the radiographic conditions with excellent operability, while positioning the patient as stated above.

Preferably, the operation panel has display means, and a picture for supporting the input operation of the radiographic conditions is displayed in the display means. For example, a picture showing a dental arch and a tomographic position is displayed, and the radiologist can specify the tooth to be radiographed with reference to the picture and area code. The swivel means moves and drives the swivel arm on the basis of the radiographic conditions entered from the operation panel. Therefore, the radiologist can enter the radiographic conditions while observing the displayed picture, and the input operation of the radiographic conditions is easier as compared with the case having no picture display.

According to the invention, moreover, the input means possesses radiograph mode selection means, setting condition selection means, and parameter setting means, and the display means has a radiograph mode display region, a setting condition display region, and a parameter display region. When any one of the plurality of predetermined radiographic modes is selected by the radiograph mode selection means, the selected radiograph mode is held in the radiographic mode display region, while the setting conditions corresponding to the selected radiographic mode are displayed in the setting condition display region. Thus, while observing the setting conditions displayed in the setting condition display region by the display means, the radiologist can set the parameters corresponding to the setting conditions by use of the parameter setting means. The parameters are displayed in the parameter display region corresponding to the setting conditions. In this way, when setting a plurality of radiographic conditions, the radiographic conditions can be divided into the radiographic mode, setting conditions and parameters, and hence the radiographic mode, setting conditions and parameters can be selected or set individually, and therefore in the event of an input error, it can be recognized by viewing the display immediately after setting displayed in each display region of the display means, and can be corrected easily.

Also according to the invention, the radiographic mode, setting conditions, and parameters by respectively by the radiographic mode selection means, setting condition selection means, and parameter setting means are stored in a nonvolatile memory. Thus, the radiographic modes, setting conditions, and parameters frequently used in routine activities can be stored regardless of presence or absence of radiography by the radiographic apparatus, and when performing the same radiography again, it is not necessary to repeat the same setting operation as in the previous time, and the waste of time spent for setting operation is saved, and the medical consultation time can be shortened.

Also according to the invention, the display means has a region for displaying the radiographic related information including the radiographic site, projection angle and tomographic mode, schematically in figures and characters. With such display region, the radiographic related information can be intuitively recognized visually, so that the setting operation of radiographic conditions is smooth and easy.

Also according to the invention, the radiographic apparatus comprises radiographic mode selection means, setting condition selection means, parameter setting means, and display means. The radiologist, first, selects any one of the plurality of predetermined radiographic modes by the radiographic mode selection means, and the selected radiographic mode is displayed by the display means, and the setting conditions corresponding to the radiographic mode are displayed. While reviewing the setting conditions, the radiologist selects the setting conditions by the setting condition selection means, and the parameters corresponding to the selected setting conditions are set by the parameter setting means. Thus selected radiographic mode, setting conditions and parameters are displayed by the display means. If the radiologist makes a mistake in input operation, the misoperation can be easily corrected by every means, and the time required for correcting input error due to misoperation can be shortened, and the input operation of the radiographic conditions of the radiographic apparatus can be supported.

Also according to the invention, the support device comprises a nonvolatile memory for storing the radiographic mode, setting conditions and parameters selected by the radiographic mode selection means, setting condition selection means, and parameter setting means. By comprising such nonvolatile memory, the radiographic modes, setting conditions and parameters which are used very often can be stored, so that the input operation of the radiographic conditions upon start of radiographic operation can be omitted or simplified.

Also according to the invention, the support device comprises display means for displaying the radiographic related information schematically by using figures and characters. By schematic display of the radiographic related information by using graphs and characters, the radiographic related information can be visually recognized, and input errors can be decreased.

Also according to the invention, the support device displays a plurality of tomographic position display lines for displaying the tomographic positions at the radiographic site. These tomographic position display lines can be moved to a desired radiographic site by the parameter setting means, and by varying the interval of the tomographic position display lines, a tomograph remote from one section of notice by a desired distance can be obtained.

Also according to the invention, the radiographic mode selection means of the support device includes panoramic radiography, jaw bone and dentition cross sectional tomography, dentition parallel tomography, maxillary sinus tomography, frontal direction temporomandibular joint tomography, temporomandibular temporal tomography, temporomandibular joint distance measuring purpose radiography, temporomandibular joint head angle measuring purpose radiography, maxillary sinus scanogram filming, temporomandibular joint scanogram filming, linear scan radiography, and cephaloradiography, as the plurality of predetermined radiographic modes. Hence the flexibility of radiographic mode selection is high, and a desired radiographic mode can be selected from a wide range of radiographic modes.

Also according to the invention, in setting the radiographic conditions in radiography, any one of the plurality of predetermined radiographic modes is selected at the first step, the selected radiographic mode and its setting conditions are displayed at the second step, the plurality of setting conditions displayed at the second step are displayed at the third step, the parameters of the setting conditions selected at the third step are set at the fourth step, and the selection of setting conditions at the third step and setting the setting condition parameters at the fourth step are repeated until all parameters of the plurality of setting conditions are completely set at the fifth step, so that all radiographic conditions can be set. In this way, the radiographic conditions are entered by dividing into the radiographic mode, setting conditions and parameters, and if an input error occurs, it can be corrected arbitrarily at each step, thereby avoiding the inconvenience of entering all the radiographic conditions from the beginning again as mentioned in relation to the prior art. What is more, it is constituted so as to select any one of the plurality of radiographic modes, select the setting conditions corresponding to the selected radiographic mode, and set the parameters corresponding to the select setting conditions, and therefore the radiologist can set the radiographic conditions easily and sequentially while observing the screen, without having to refer to the manual or code table during input operation.

Also according to the invention, after completion of any arbitrary step from the first to the fifth step, the set data up to the arbitrary step can be stored, and thereby by storing the set data up to the arbitrary step of high frequency of use, repetition of setting job of radiographic conditions can be avoided.

Also according to the invention, by selection a radiographic mode, the radiographic mode and setting conditions are displayed, and also the information relating to the selected radiographic mode is schematically displayed in figures and characters, so that the radiologist can visually recognize the information about the selected radiographic mode, thereby decreasing input errors.

BRIEF DESCRIPTION OF THE DRAWINGS

Other and further objects, features, and advantages of the invention will be more explicit from the following detailed description taken with reference to the drawings wherein:

FIG. 7 is a block diagram showing a schematic constitution of control means 95 provided in the radiographic apparatus 40;

FIG. 16 is a flow chart for explaining the operation procedure of maxillary sinus panoramic radiography;

FIG. 19 is a flow chart for explaining the operation procedure of jaw bone and dentition cross sectional linear tomography;

FIG. 22 is a flow chart for explaining the operation procedure of jaw bone and dentition parallel plane linear tomography;

FIG. 28 is a flow chart for explaining the operation procedure of temporomandibular joint frontal direction linear tomography;

FIG. 32 is a flow chart for explaining the operation procedure of maxillary sinus scanogram radiography;

FIG. 35 is a flow chart for explaining the operation procedure of temporomandibular joint scanogram radiography;

FIG. 37 is a flow chart for explaining the operation procedure when the projection direction is set in the frontal side in temporomandibular joint scanogram radiography;

FIG. 40 is a flow chart for explaining the operation procedure when the projection direction is set in the lateral direction in skull linear scanning radiography;

FIG. 45 is a flow chart for explaining the operation procedure of temporomandibular joint distance measuring purpose linear tomography;

DETAILED DESCRIPTION OF THE PREFERRED EMBODIMENTS

Figure 1:
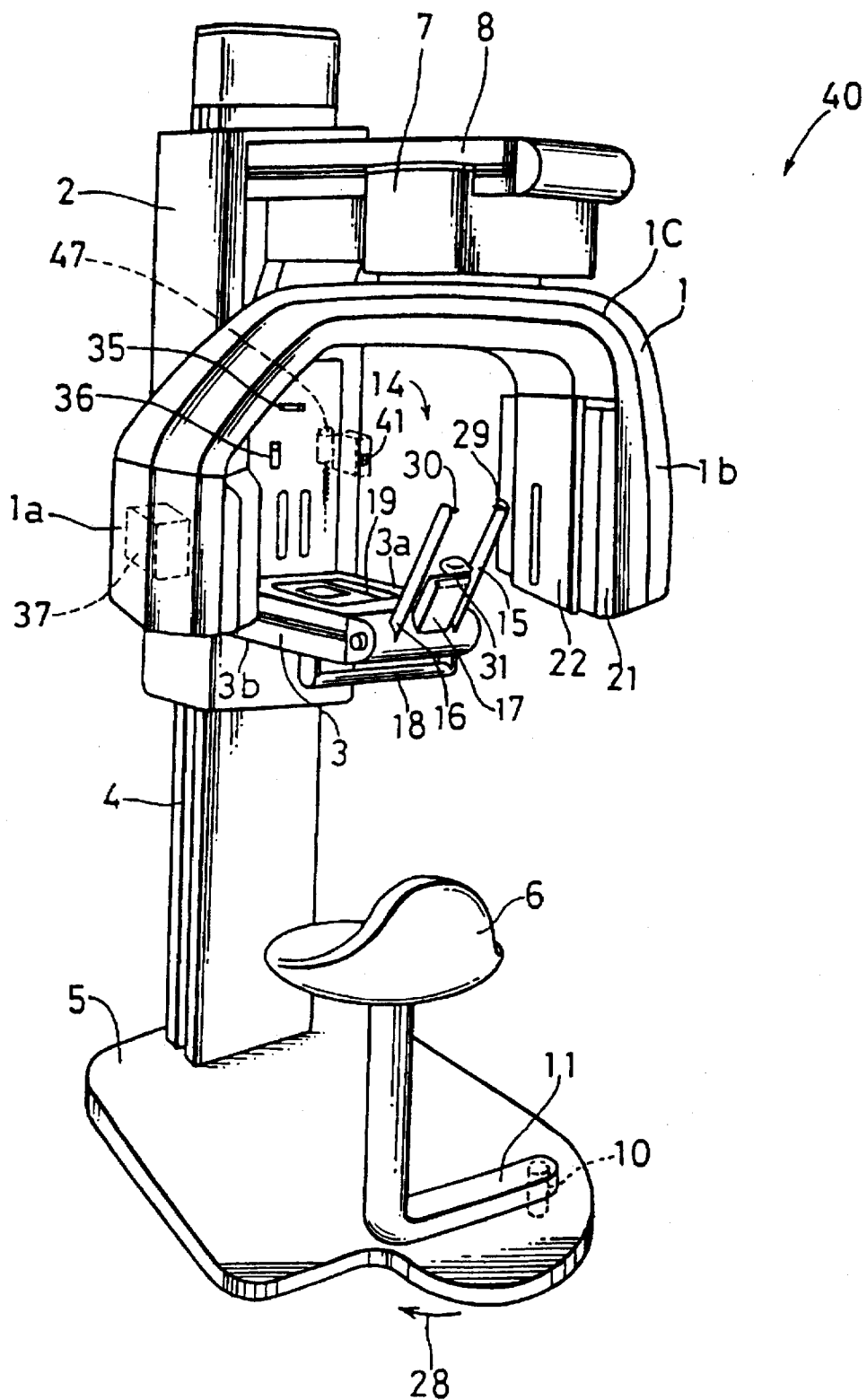
FIG. 1 is a perspective view showing a radiographic apparatus 40 in an embodiment of the invention.

Now referring to the drawings, preferred embodiments of the invention are described below.

Figure 2:
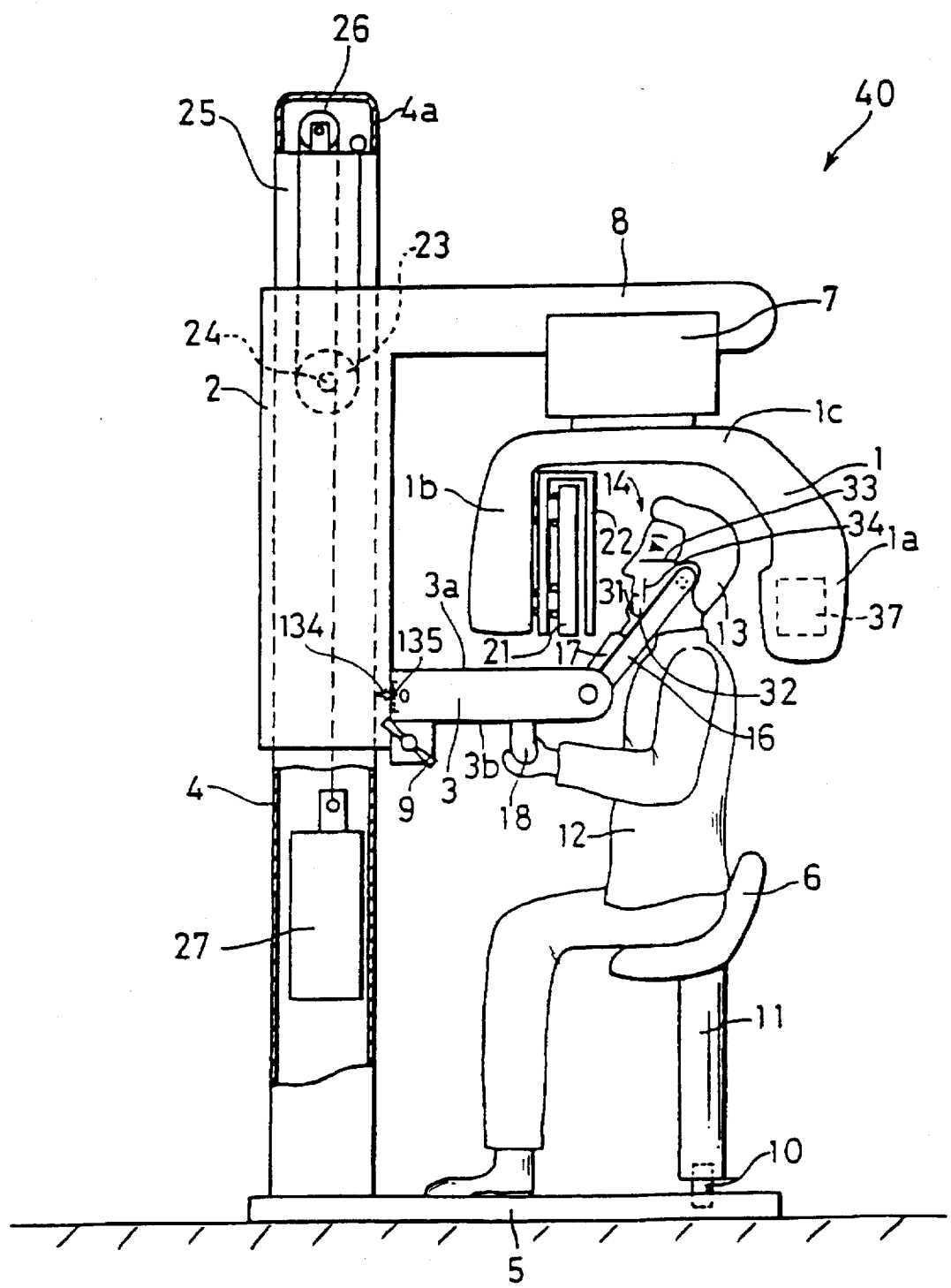
FIG. 2 is a partially cut-away side view showing the state of use of the radiographic apparatus 40.

FIG. 1 is a perspective view showing a radiographic apparatus 40 in an embodiment of the invention, and FIG. 2 is a partially cut-away side view for explaining the state of use of the radiographic apparatus 40. The radiographic apparatus 40 roughly comprises a swivel arm 1, an ascending/descending main body 2, a patient frame 3, a post 4, a base 5, and a chair 6.

The swivel arm 1 is formed nearly in U-shape, and an X-ray source 37, a slit plate and others are provided in one end 1a, and a film cassette 21 and a slit plate 22 are incorporated in other end 1b, together with X-ray detecting means realized by displacement driving mechanism of the film cassette 21, a charge coupling device, etc.

The area in the middle 1c of the swivel arm 1 is supported by a holding frame 8 through a swivel mechanism 7, and the holding frame 8 is extended from the ascending/descending main body 2. In the swivel mechanism 7, swivel means for moving the swivel arm 1 and XY table are incorporated together with others. Therefore, the swivel arm 1 can be moved and driven along the contour of the dental arch of the patient, so that panoramic radiography is possible, while plane tomography is also possible on an arbitrary section of the teeth and skull.

The ascending/descending main body 2 is movable in the vertical direction on the post 4, and a moving pulley 23 is provided inside. The moving pulley 23 is rotatably mounted on the ascending/descending main body 2, and is rotated and driven by a motor and a power transmission mechanism (not shown). A wire 25 of which one end is fixed on the top 4a of the post 4 is applied on the moving pulley 23, and the other end of this wire 25 is coupled to a balance weight 27, through a fixed pulley 26 provided in the top 4a, by way of the moving pulley 23. The balance weight is guided to be free to move up and down in the post 4. Therefore, as mentioned above, when the moving pulley 23 is rotated and driven, the ascending/descending main body 2 is moved in the vertical direction.

The ascending/descending main body 2 is provided with guide rails and others (not shown), and through the guide rails the patient frame 3 is provided so as to be free to move in the vertical direction independently of the ascending/descending main body 2. By manipulating a lock handle 9, brake means provided in the patient frame 3 acts on the post 4, so that the patient frame 3 can be positioned.

On the upper side 3a of the patient frame 3, an operation panel 19 having display means for displaying the support screen for input operation is provided. Furthermore, in the lower side 3b of the patient frame 3, a grip 18 is provided, and by holding this grip 18, the position of the patient 12 can be stabilized during radiographing, and at the same time the shoulders of the patient 12 are lowered, so that the movement of the swivel arm 1 is not disturbed.

The post 4 stands up from the base 5, and an oscillating member 11 is attached oscillatably to the base 5 by means of a rotary shaft 10. The chair 6 is attached to the oscillating member 11, and in time of radiography the patient 12 is placed in a specified radiographic position in the arrow 28 direction by oscillation of the oscillating member 11, so that the patient 12 may be smoothly introduced, without any feeling of fear or threat, to the swivel arm 1 positioned near the head 13.

Head holding means 14 for positioning and holding the head 13 of the patient 12 roughly comprises a pair of right and left temporal holding members 15, 16 corresponding to the both temporals of the patient 12, and a chin rest 17. The pair of temporal holding members 15, 16 and the chin rest 17 are fitted to the free end of the patient frame 3.

The base ends of the temporal holding members 15, 16 are movable so as to come closer to each other and depart from each other, and ear rods 29, 30 are provided at their free ends. The temporal holding members 15, 16 and ear rods 29, 30 are made of a material having high X-ray transmissivity and rigidity, such as an acrylic resin, a fiber reinforced plastic using carbon fibers and polycarbonate.

The chin rest 17 is placed between the temporal holding members 15, 16, and the jaw 32 of the patient 12 is placed on the platform 31 of the chin rest 17. The chin rest 17 is structured to be expandable in a direction parallel to the temporal holding members 15, 16. Patient positioning light beam generators 35, 36 project eye-ear horizontal beam 33 or median beam 34 to the face of the patient 12, to be used as a reference for positioning the patient 12.

Figure 3:
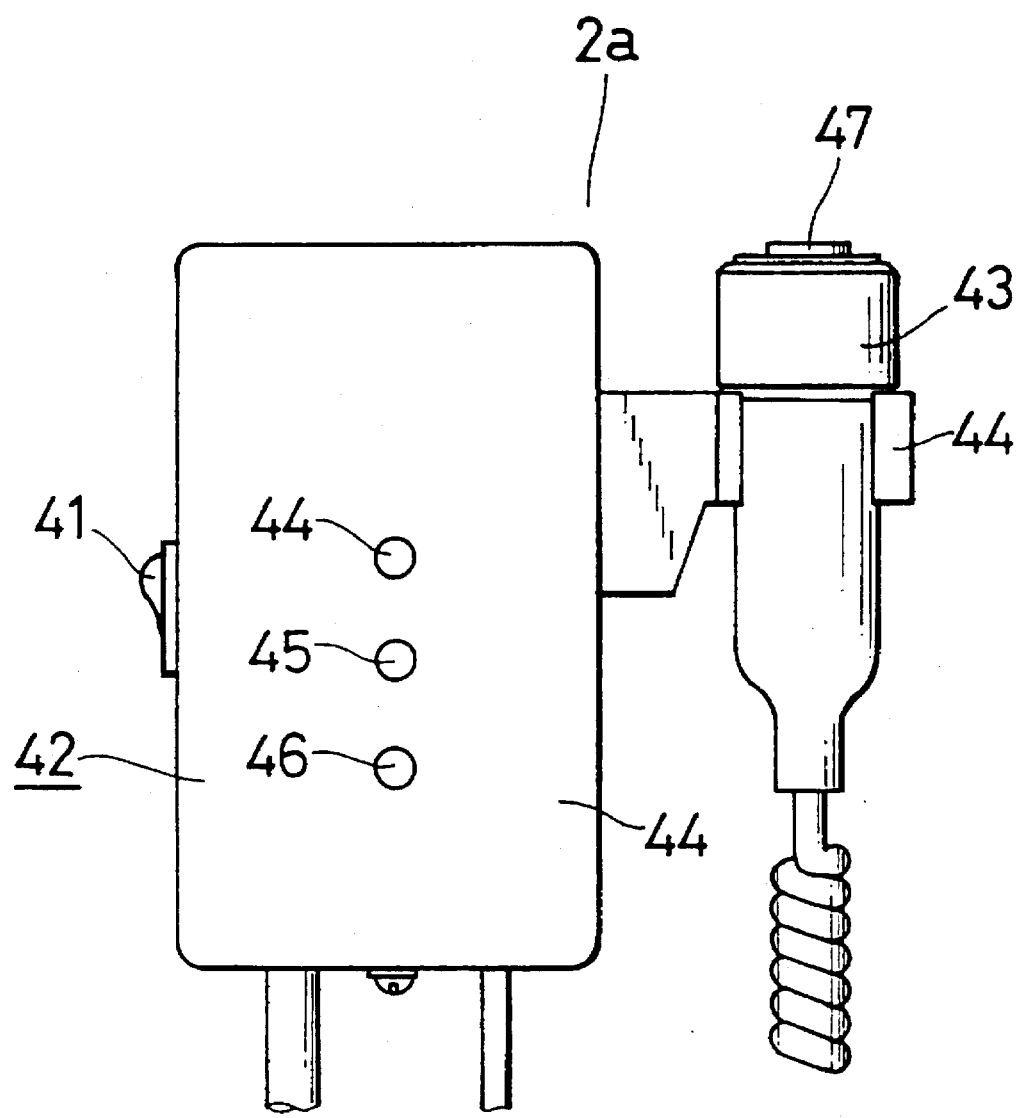
FIG. 3 is a diagram showing a switch box 42 comprising a main power switch 41, and an X-ray irradiation switch 43.

FIG. 3 is a front view showing a switch box 42 having a main power switch 41 and an X-ray irradiation switch 43. The switch box 42 and the X-ray irradiation switch 43 are provided at one side 2a of the ascending/descending main body 2 (see FIG. 1), and the main power switch 41 is provided at one side of the switch box 42. At the other side of the switch box 42, a holder 44 for detachably holding the X-ray irradiation switch 43 is fixed, and an exposure lamp 44, a ready lamp 45, and a main lamp 46 are provided from top to bottom in this order on a front wall 55 of the switch box 42. The X-ray irradiation switch 43 is a so-called deadman switch, and when an irradiation button 47 provided in the upper part is being kept depressed, the swivel arm 1 moves in the irradiation direction corresponding to the radiographic position, and after preheating the X-ray tube for 2.5 seconds, the swivel arm 1 and film cassette 21 move in parallel to start X-ray irradiation. During X-ray irradiation, the exposure lamp 44 lights, for example, in red, and the buzzer sounds. When the irradiation button 47 is released, X-ray irradiation is stopped at the same time in any case. The main lamp 46 lights, for example, in green when the main power switch 41 is turned on to tell that the power is turned on. The ready lamp 45 lights, for example, in yellow when the power is turned on by the main power switch 41, telling that it is ready to emit X-ray by pressing the irradiation button 47.

Figure 4:
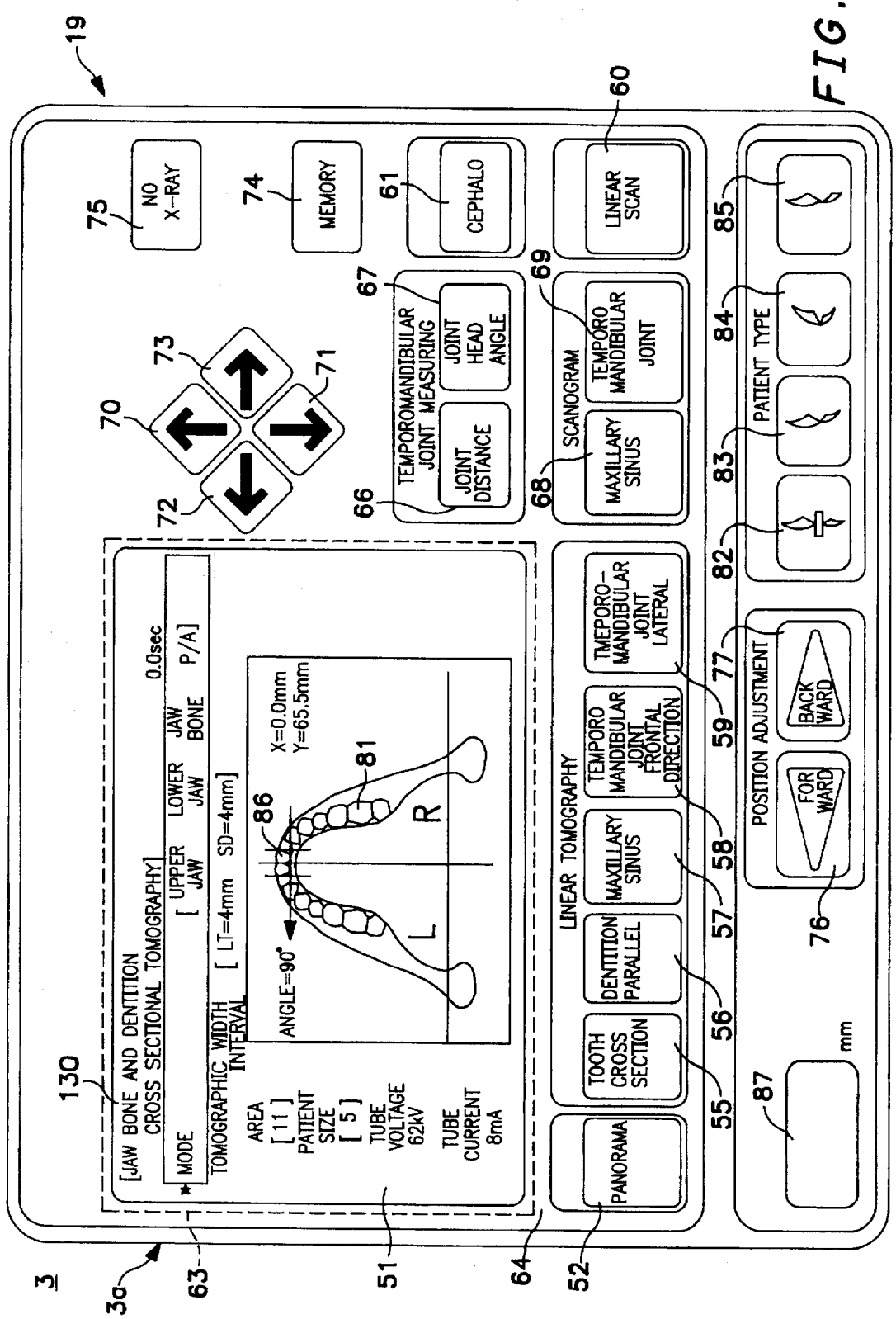
FIG. 4 is a plan view showing an operation panel 19 of the radiographic apparatus 40.

FIG. 4 is a plan view showing the operation panel 19. The operation panel 19 comprises display means 63 realized, for example, by a liquid crystal display element, and input means 64 laminated on the display means 63. The input means 64 is constituted by laminating an orthogonal lattice-form transparent electrode in a spaced state on mutually confronting surfaces of two transparent elastic synthetic resin sheets having an electric insulation property, and may be easily available as a commercial sheet switch. Such input means 64 composes a plurality of switching elements by the transparent electrode, which are selectively pressed by the radiologist. Beneath the input means 64, a transparent display unit 51 disposing the display means is formed. The input means 64 comprises "panorama" key 52, "tooth cross section" key 55, "dentition parallel" key 56, "maxillary sinus" key 57, "temporomandibular joint frontal direction" key 58, "temporomandibular joint lateral" key 59, "linear scan" key 60, "cephalo" key 61, "joint distance" key 66, "joint head angle" key, "maxillary sinus" key 68, "temporo-mandibular joint" key 69, up cursor key 70, down cursor key 71, left cursor key 72, right cursor key 73, memory key 74, and No X-ray key 75.

By the "panorama" key 52, "tooth cross section" key 55, "dentition parallel" key 56, "maxillary sinus" key 57, "temporomandibular joint frontal direction" key "temporomandibular joint lateral" key 59, "linear scan" key 60, "cephalo" key 61, "joint distance" key 66, "joint head angle" key, "maxillary sinus" key 68, "temporomandibular joint" key 69, the radiographic mode selecting means is constituted. By the up cursor key 70 and down cursor key 71, the setting condition selection means is constituted. By the left cursor key 72 and right cursor key 73, the parameter input means is constituted.

The input means 64 further comprises, beside the various keys listed above, "forward" key 76 and a "backward" key 77 for moving the swivel arm 1 from a predetermined reference position forward and backward in the lateral direction in FIG. 2, and a plurality of edge-to-edge occlusion keys 82, 83, 84, 85 for individually setting the tube voltage and tube current of the X-ray tube depending on the occlusion of the patient. The operation panel also comprises a distance display unit 87, left side of the "forward" key 76 and below the "panorama" key 52, for displaying the distance from the predetermined reference plane to the anterior teeth of the patient measured by a distance sensor (not shown).

Panoramic radiography is achieved by moving the swivel arm 1 by means of the swivel means or X-Y table as mentioned above. As a result, a curvature tomograph, for example, in the imaging region including the dentition arranged along the mandible is obtained. The supporting image for such panoramic radiography is displayed by pressing the "panorama" key 52 of the operation panel 19.

The display screen 51 in FIG. 4 shows an example of the image displayed at the time of input of the plane tomographic condition. The plane tomography is executed by the linear track system, and tomographic images, for example, on a plurality of planes vertical to the dental arch direction 86 of the dentition 81 shown in the drawing are obtained continuously. Such display image is displayed by pressing the "dentition cross section" key 55 of the plurality of plane tomographic keys 55–54 of the operation panel 19.

Similarly, tomographic images on a plurality of planes parallel to the dental arch direction 86 may be also obtained continuously. Such display image is displayed by pressing the "dentition parallel" key 56 out of the plurality of plane tomographic keys 55–59 of the operation panel 19.

It is also possible to obtain continuously tomographic images on a plurality of planes parallel to the frontal surface in the region including the maxillary sinus. Such display image is displayed by pressing the "maxillary sinus" key 57 of the plurality of plane tomographic keys 55–59 of the operation panel 19.

Furthermore, in the region including the temporomandibular joint, tomographic images from each direction can be obtained continuously. Such display image is displayed by pressing the "temporomandibular joint frontal direction" key 58 or "temporomandibular lateral" key 59 of the plural plane tomographic keys 55–59 of the operation panel 19. From the "linear scan" key shown in FIG. 4, scanning of the section to be tomographed in the plane tomography is instructed.

From the "cephalo" key 61, cephaloradiography is instructed. The cephaloradiography is a technique for radiographing by keeping always a specific condition in the configuration of the X-ray source and the subject, by fitting head fixing means called cephalostat (not shown), for fixing the head 13 of the patient 12 of a subject to the radiographic apparatus 40.

Figure 5A:
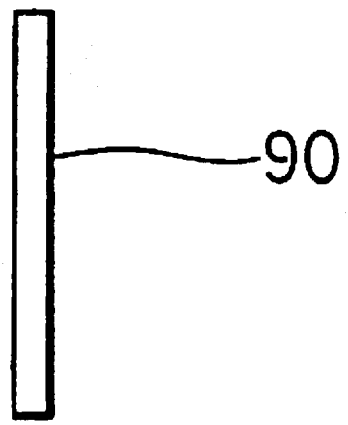
FIGS. 5A, 5B are views showing the shape of a slit of a slit plate 22, FIG. 5A showing a narrow gap slip 90 and FIG. 5B showing a wide slit 91.
Figure 5B:
Figure 6A:
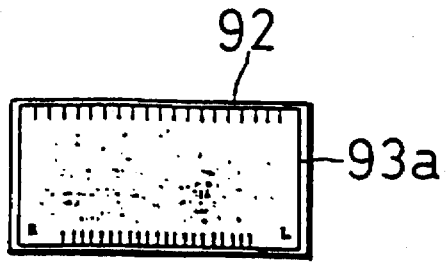
FIGS. 6A–6G are front views showing X-ray images 93a–93g of an X-ray film 92, respectively.

FIG. 5 is a diagram showing the shape of a narrow gap slit 90 and a wide slit 91 of the slit plate 22 provided in the film cassette 21. In the drawing, FIG. 5A shows the narrow gap slip 90, and FIG. 5B relates to the wide slit 91. By selecting these slits 90, 91, as shown in FIG. 6A–FIG. 6 G, X-ray images are formed in the image regions indicated by reference numerals 93a–93g in an X-ray film 92 loaded in the film cassette 21.

FIG. 7 is a block diagram showing a schematic electrical construction of control means 95 of the radiographic apparatus 40 of the embodiment. The control means 95 comprises an input and output control unit 96 for mainly controlling the display means 63, input means 64, and X-ray source 37, and a drive system control unit 97 for controlling the mechanical action of plural motors M1–M7 and others provided in the radiographic apparatus 40. The two units 96, 97 are electrically connected by means of a communication line 98, so that data communication can be conducted mutually. The input and output control unit 96 possesses a first input and output interface circuit 121 and a first signal processing circuit 122, and the first signal processing circuit 122 has a nonvolatile memory 123 realized by EEPROM.

The drive system control unit 97 comprises a second input and output interface circuit 124, a second signal processing circuit 125, and a drive control data memory 126 realized by ROM. An input signal from the input means 64 is provided to the first input and output interface circuit 121, and this signal is processed in the first signal processing circuit 122, and is transferred to the second signal processing circuit 125 through the communication line 98. In the second signal processing circuit 125, approval or rejection of radiography is judged in response to the detection signal from the plural state detection sensors S1–S13 through the second input and output interface circuit 124, and the result is transferred again to the first signal processing circuit 122 through the communication line 98. Such data transmission or reception between the first and second signal processing circuits 122, 125 is done by interruption handling.

Figure 8:
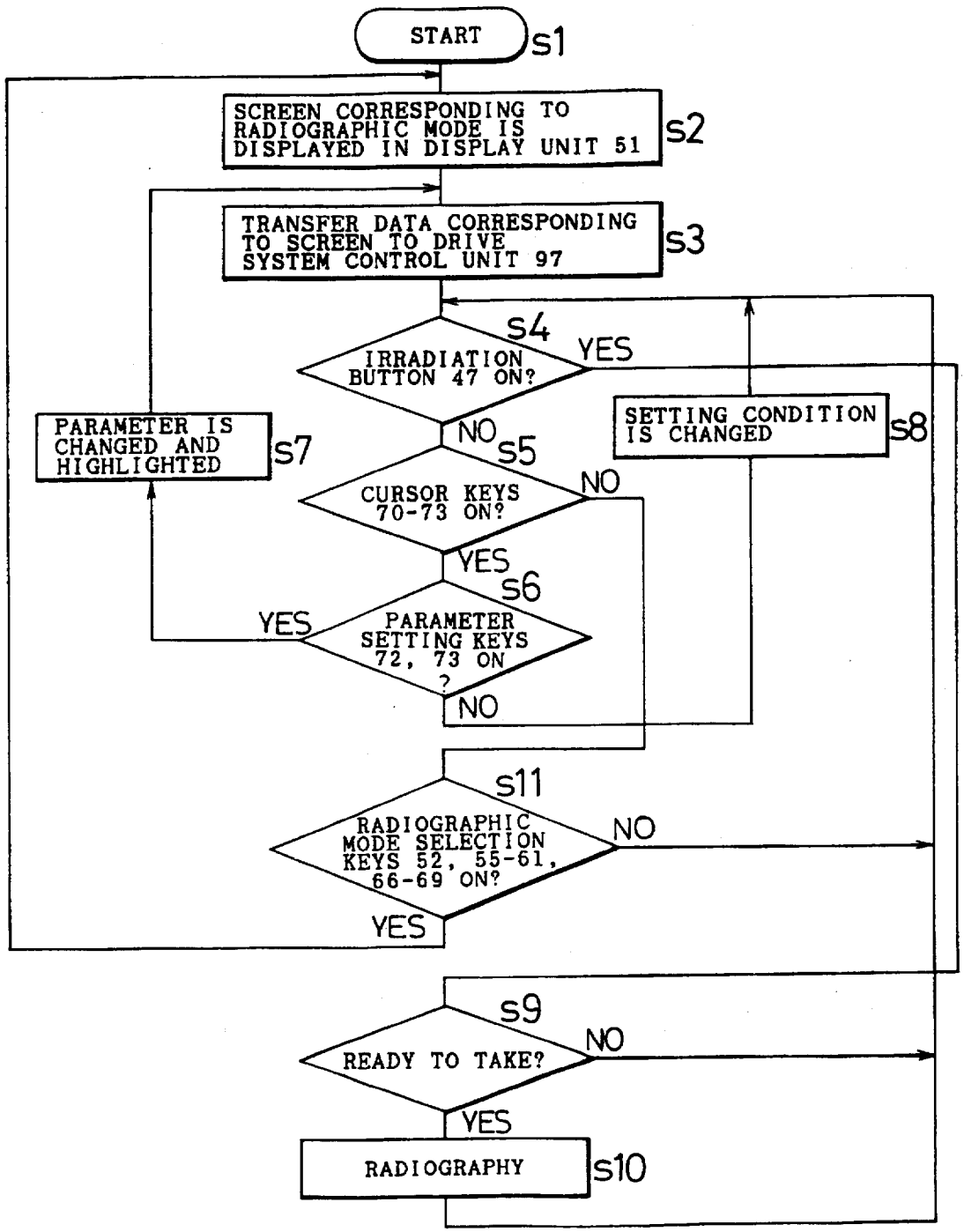
FIG. 8 is a flow chart for explaining the operation of the control means 95.

FIG. 8 is a flow chart for explaining the operation of the control means 95. Radiographic operation is stated at step s1, and when the main power switch 41 is turned on, a predetermined condition setting screen appears in the display unit 51 at step s2. As the predetermined condition setting screen is selected the screen for panoramic radiography in this embodiment. The radiographic condition data relating to panoramic radiography is stored in the nonvolatile memory 123. At step s3, the first signal processing circuit 122 transfers the radiographic condition data displayed in the display unit 51 to the second signal processing circuit 125. The second signal processing circuit 125 compares the detection signal from the plural state detection sensors S1–S13 with the data received from the first signal processing circuit 122, and judges approval or rejection of radiography, and transfers the result to the first signal processing circuit 122. In this state, the exposure lamp 44 and ready lamp 45 in the switch box 42 are put out, and only the main lamp 46 is lighted. When the X-ray irradiation switch 43 is in OFF state, the operation goes to step s5, where it is judged whether the data displayed in the display unit 51 has been changed or not by the up cursor key 70, down cursor key 71, left cursor key 72 or right cursor key 73. When the setting condition is changed by the up cursor key 70 or down cursor key 71, the operation skips to step s6. When the parameter has been changed by the left cursor key 72 or the right cursor key 73, the operation goes to step s7, where the parameter is changed and the display state is highlighted, and thereby returns to step s3.

At step s4, when the irradiation button 47 of the X-ray irradiation switch 43 is pressed, the operation goes to step s9, where approval or rejection of radiography in the drive system control unit 97 is judged. When radiography is approved, the ready lamp 45 lights up, the operation goes to next step s10, where the exposure lamp 44 lights and X-rays are emitted from the X-ray source 37. At this time, by pressing the irradiation button 47, the swivel arm 1 rotates, and X-rays are emitted from the X-ray source 37. When the swivel arm 1 reaches the final position, rotation of the swivel arm 1 and X-ray emission are stopped automatically, and even when any abnormality occurs or the irradiation button 47 has been kept depressed, it is designed to stop X-ray emission in about 20 seconds.

Unless the X-ray irradiation switch 43 is turned on, the operation goes to step s5, where when the setting condition is not changed, the operation skips to step s11. At step s11, it is judged whether radiographic mode has been changed, that is, whether any one of the plural keys 52, 55–61, 66–69 for composing the radiographic mode selection means has been pressed or not. Going to step s4 when the radiographic mode is not changed, or to step s2 when changed, the steps s3–s11 are repeated.

The radiographic apparatus 40 of the embodiment can select various radiographic modes explained below as plural radiographic modes, that is, panoramic radiography, jaw bone and dentition cross sectional tomography, dentition parallel tomography, maxillary sinus tomography, temporomandibular joint frontal tomography, temporomandibular temporal tomography, temporomandibular joint distance measuring radiography, temporomandibular joint head angle measuring radiography, maxillary sinus scanogram filming, temporomandibular joint scanogram filming, linear scan radiography, and cephaloradiography, and the individual radiographic modes are described below while referring to Tables 1–5.

First, the panoramic radiography will be described.

TABLE 1

Figure 9:
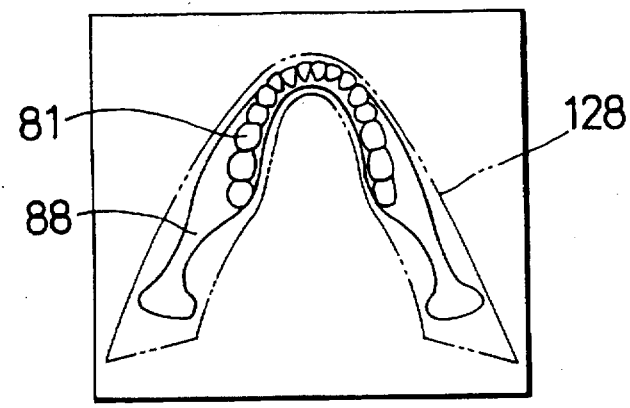
FIG. 9 is a diagram showing an imaging region by dentition standard panoramic radiography.

| RADIOGRAPH TYPE | KEY SELECTION | RADIOGRAPHIC CONDITION SETTING ON OPERATION PANEL | | PATIENT POSITIONING | | |
|---|---|---|---|---|---|---|
| | | MODE SELECTION | EXPOSURE | REFERENCE PLANE POSITIONING | PATIENT REST METHOD | |
| PANORAMA FIG. 9 FIG. | "PANORAMA" KEY 52 | DENTITION STANDARD (STANDARD PANORAMA) 1.3 TIMES DENTITION | AUTO | EYE-EAR PLANE (IN PANORAMIC RADIOGRAPHY FOR AREA SELECTION CAMPER'S PLANE MAY BE USED AS REFERENCE DEPENDING | JAW BONE PLANE (IN PANORAMIC RADIOGRAPHY FOR AREA SELECTION, EAR ROD PLATE MAY BE USED DEPENDING ON SITE) | CHIN REST |

TABLE 1-continued

Figure 14A:
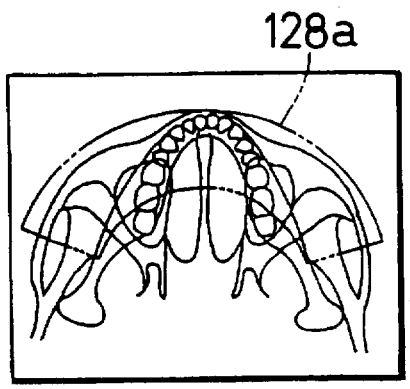
FIGS. 14A, 14B are diagrams showing imaging regions 128a, 128b, respectively, by maxillary sinus panoramic radiography.
Figure 14B:
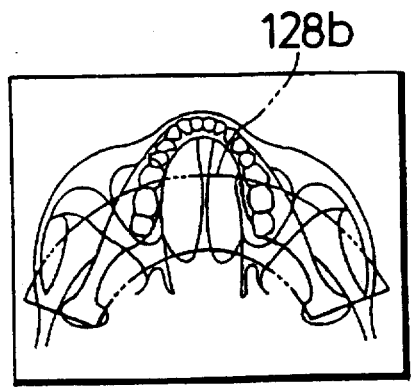

| 12 | STANDARD (STANDARD PANORAMA) 1.7 TIMES | ON SITE) | | | |
| FIG. 14 | MAXILLARY SINUS STANDARD (MAZILLARY SINUS PANORAMA) 1.5 TIMES | | | | |

Figure 12:
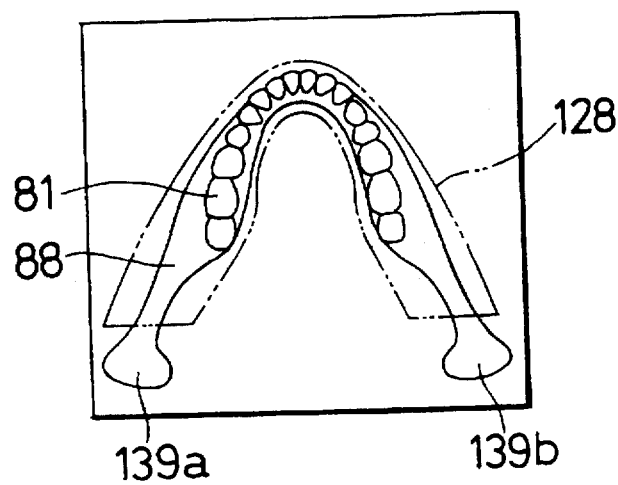
FIG. 12 is a diagram showing an imaging region by dentition magnified panoramic radiography.

| | | | PATIENT POSITIONING | | X-RAY FILM |
| | RADIOGRAPH TYPE | IRRADIATION FIELD BEAM | TOMO- GRAPHIC BEAM | SECOND SLIT SELECTION | (SENSI- TIZED PAPER) SELECTION |
| --- | --- | --- | --- | --- | --- |
| | PANORAMA FIG. 9 | LOWER LIP LOWER | AUTO FOCUS | FIG. 5A | FIG. 6A |
| | FIG. 12 | EDGE | | | FIG. 6A |
| | FIG. 14 | NOSE WINGS | | | FIG. 6A |

As seen from Table 1, the panoramic radiography is available in three types, that is, dentition standard panoramic radiography with the image magnified 1.3 times, dentition magnified panoramic radiography magnified 1.7 times, and maxillary sinus panoramic radiography magnified 1.5 times.

Figure 10:
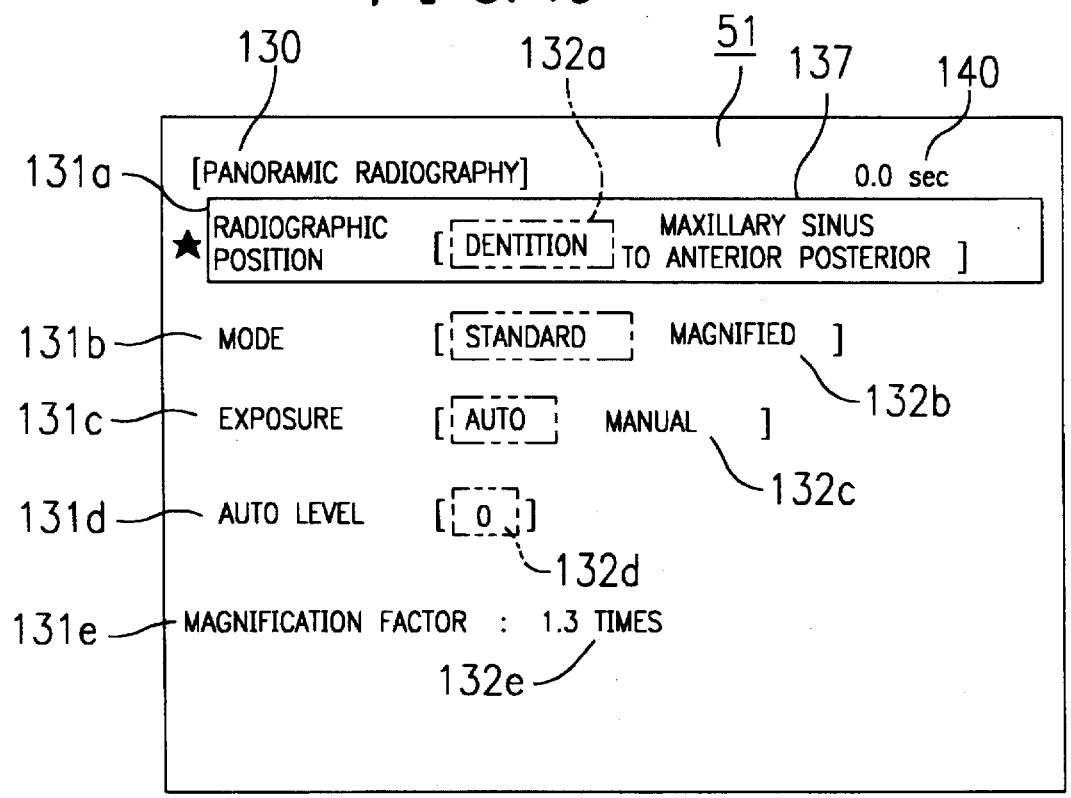
FIG. 10 is a diagram showing display data of a display unit 51 of dentition standard panoramic radiography.
Figure 11A:
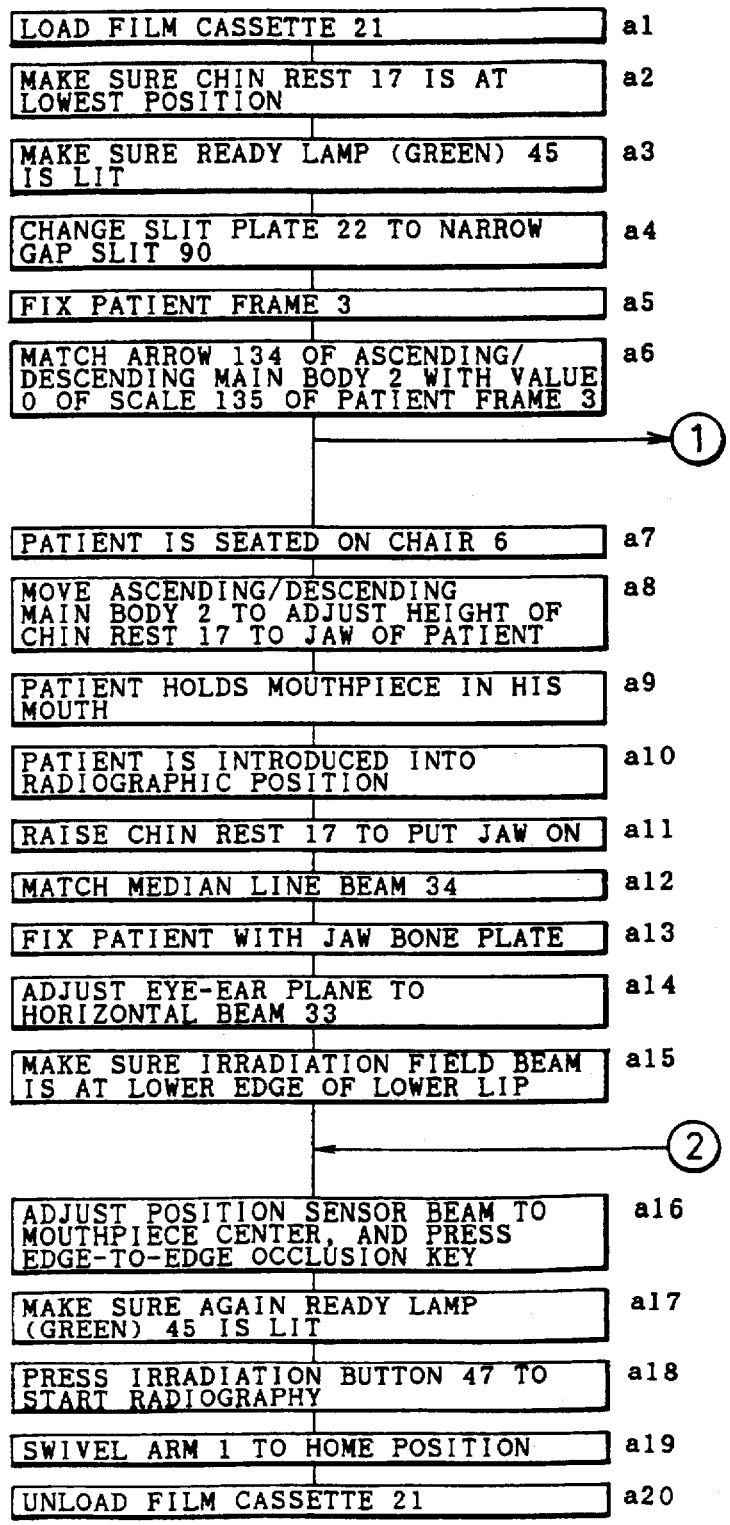
FIGS. 11A, 11B are a flow chart for explaining the operation procedures of dentition standard panoramic radiography.
Figure 11B:
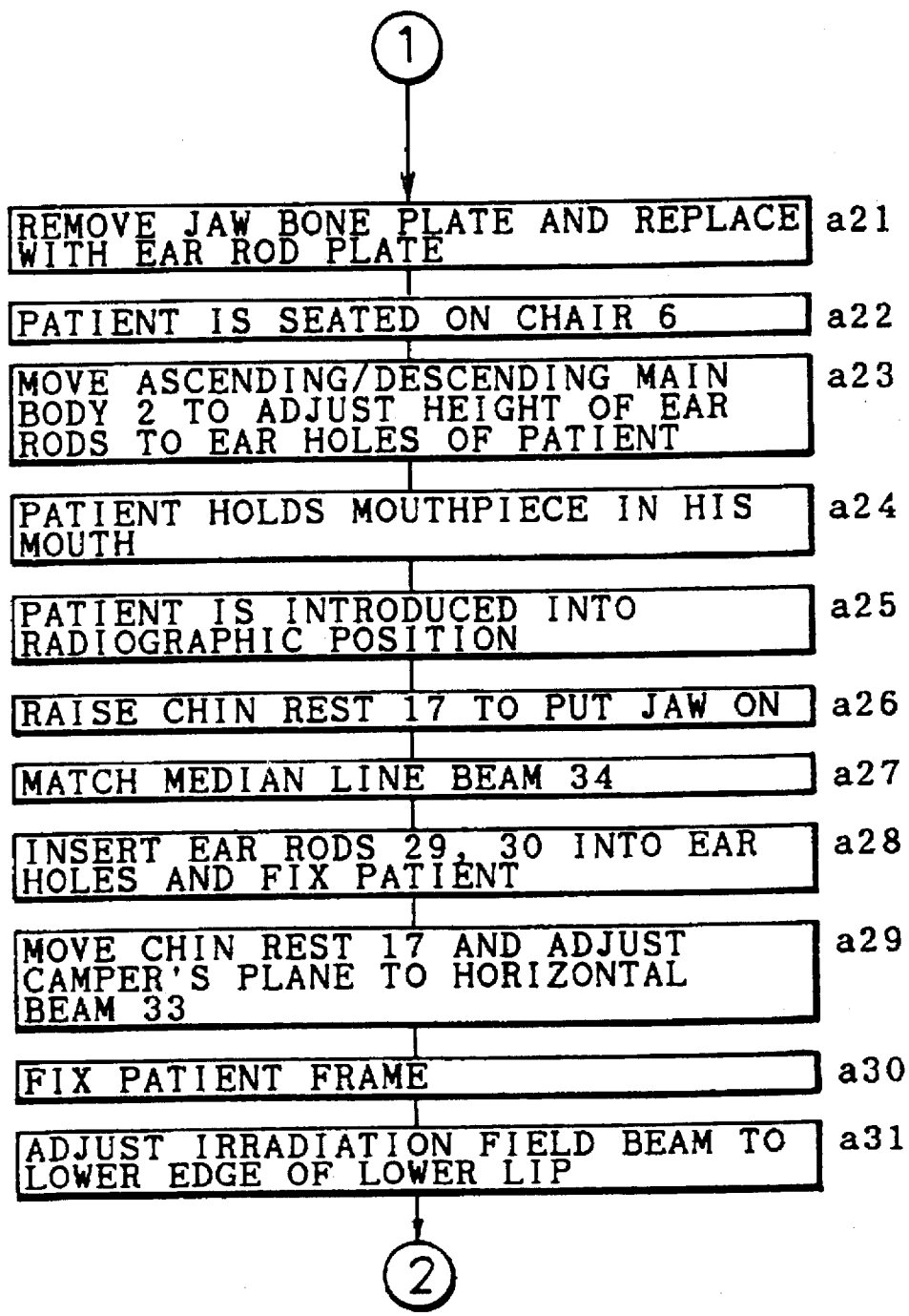

FIG. 9 is a diagram showing the imaging region by dentition standard panoramic radiography, FIG. 10 is a diagram showing display data shown in the display unit 51 by the display means 63 in dentition standard panoramic radiography, and FIG. 11 is a flow chart for explaining the procedure of dentition standard panoramic radiography. In dentition standard panoramic radiography, the image magnification factor is set at 1.3 times, and an overall jaw image in the region including the dentition 81 and jaw bone 88 enclosed by virtual line 128 in FIG. 9 is obtained. The operation procedure of dentition standard panoramic radiography is described below.

First, when the main power switch 4 is turned on, the radiographic mode is automatically set to panoramic radiographic mode, and the main lamp 46 of the switch box 42 lights up. In the radiographic mode display region 130 of the display unit 51, "panoramic radiography" is displayed, beneath the radiographic mode display region 130, there are plural setting condition display regions 131a–131e (subscripts a, b, c, . . . are omitted when described collectively) for displaying the setting conditions of "radiographic position," "mode," "exposure," "auto level," and "magnification factor," and at the right side of the setting condition display regions 131a–131e, there are parameter display regions 132a–132e (subscripts a, b, c, . . . are omitted when described collectively) for displaying parameters corresponding to the setting conditions, "dentition, maxillary sinus to anterior, posterior," "standard, magnified," "auto manual," "0," and "1.3 times."

Such display state shown in FIG. 10 is similarly displayed when the "panorama" key 52 is pressed in other radiographic mode. When the "panorama" key 52 is not pressed, the display data corresponding to the previous radiographic mode is shown. This display data has been stored in the nonvolatile memory 123 in the control means 95 by pressing the "memory" key 74.

Referring to FIG. 11, the operation procedure will be described. First, at step a1, the film cassette 21 is loaded in the other end 1b of the swivel arm 1. This film cassette 21 contains an X-ray film 92 with scales as shown in FIG. 6A. At step a2, the radiologist confirms that the chin rest 17 is at the lowest position, and makes sure the ready lamp 45 is lighted at step s3. At step a4, changing over the slit plate 22 manually, the narrow gap slit shown in FIG. 5A is set. At step a5, the patient frame 3 is fixed by the lock handle 9, and at step a6, the arrow 134 (see FIG. 2) of the ascending/descending main body 2 and the zero value of graduations 135 of the patient frame 3 are matched, and the lock handle 9 is manipulated to the panorama lock side. The operation procedure for positioning the patient differs between the cases of radiographing on the eye-ear plane by using the temporal holding members 15, 16 and radiographing on the Camper's plane by using the ear rods 29, 30.

That is, in the case of eye-ear plane radiography by using temporal holding members 15, 16, the operation goes to step a7, where the patient 12 is seated on the chair 6, and the ascending/descending main body 2 is moved at step a8 to adjust the height of the chin rest 17 to the jaw of the patient 12. At step a9, the patient 12 bites a mouthpiece, and the patient 12 is introduced into the radiographic position at step a10, and the chin rest 17 is raised at step a11 to put the jaw on, and the median line of the patient's head is positioned at step a12 by means of a radian line beam 34 while paying attention to the inclination of the patient's head, and the patient's head is fixed at step a13 by using a jaw plate (not shown).

At step a14, the eye-ear plane of the patient 12 is adjusted to the eye-ear horizontal beam 33, and it is confirmed at step a15 that the irradiation field beam is at the lower lip lower edge, and the beam of the distance measuring sensor is adjusted to the center of the mouthpiece at step a16, and one of the edge-to-edge occlusion keys 82–85 suited to the patient 12 is selected and pressed.

At step 17, it is confirmed again that the ready lamp 45 is lighted, and the irradiation button 47 is pressed at step a18 to start radiographing. After radiographing, at step a19, the swivel arm 1 is returned to the initial position, and the film cassette 21 is removed at step a20, thereby terminating the dentition standard panoramic radiography.

In the case of Camper's plane radiography by using the ear rods 29, 30, the operation goes to steps a6–a21. The jaw bone plate used in the preceding step a13 is removed and replaced by the ear rods 29, 30.

At steps a22–a27, the same operations as those at step a7–a12 are effected, and the ear rods 29, 30 are inserted into the ear holes at step a28 to fix the patient 12. At step a29, sliding the chin rest 17, the Camper's plane is adjusted to the eye-ear horizontal beam 33, and the patient frame 3 is fixed by the lock handle 9 at step a30. Going to step a31, the ascending/descending main body 2 is moved to match the irradiation field beam with the lower lip lower edge, and thereafter the same operations as those at steps a16–a20 are effected to terminate the dentition standard panoramic radiography.

Referring again to FIG. 10, in the dentition standard panoramic radiography, the operation has been done without moving the frame display 137 showing the setting condition selected by the down cursor key 71, and without moving the cursors 138a–138d in the parameter display region 132 by automatic setting, but when desired to change the parameters of setting conditions, while sequentially moving the frame display 138 by the down cursor key 71, the parameter corresponding to the setting condition enclosed by the frame display 137 is moved by pressing the right cursor key 73, and the radiographic site is changed from the dentition to "maxillary sinus to anterior, posterior," the mode is changed from "standard" to "magnified," the exposure from "auto" to "manual," and further the auto level from 0 to one of remaining eight stages, 4, 3, 2, 1, −1, −2, −3, −4. When an exposure mode "manual" is selected, as described in detail below, the tube voltage and tube current of the X-ray source 37 are set to values suited to the patient, and in order to correct the central concentration, or enhance the image diagnostics, the intensity of the X-ray in the middle of the X-ray film may be raised. The magnification factor is set at 1.3 times when the mode is selected in "standard," and automatically set at 1.7 times when selected in "magnified."

Figure 13:
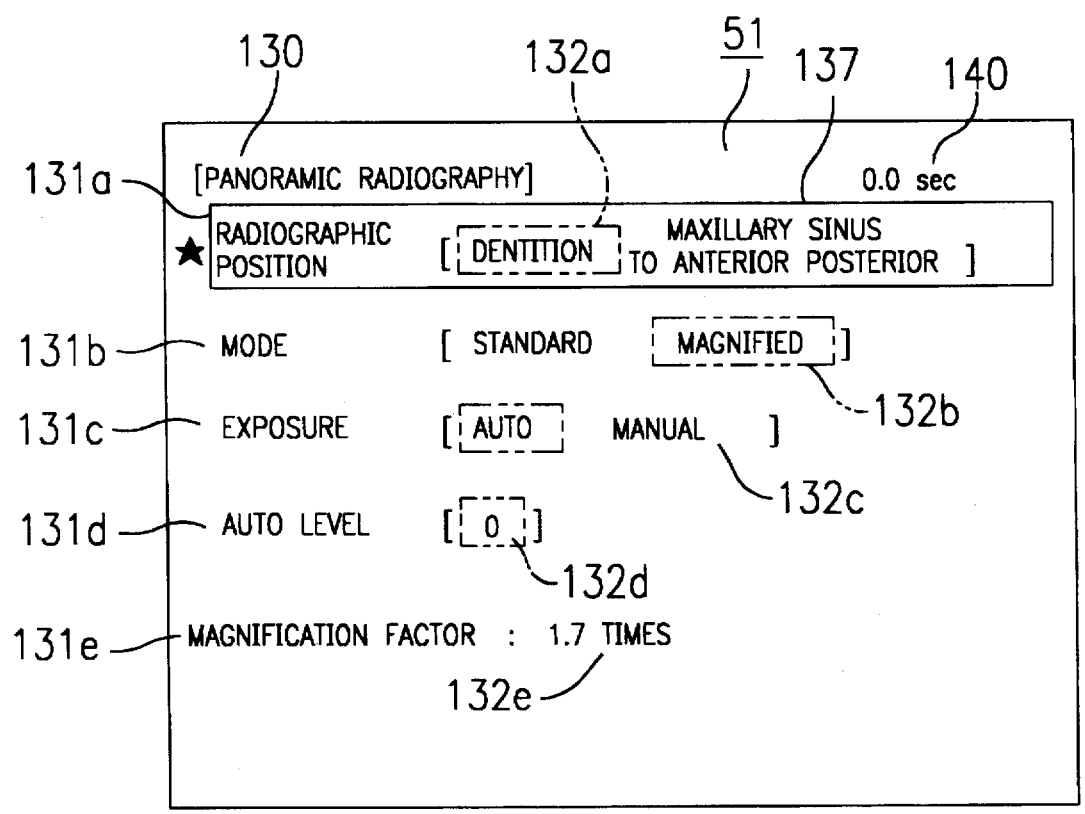
FIG. 13 is a diagram showing display data of the display unit 51 of dentition magnified panoramic radiography.

FIG. 12 is a diagram showing the imaging region by dentition magnified panoramic radiography, and FIG. 13 is a diagram showing the display state of the display unit 51. The operation procedure of dentition magnified panoramic radiography is same as that of the dentition standard panoramic radiography, and hence the description of the operation procedure is omitted, and only the manipulating procedure of the operation panel 19 is explained. In dentition magnified panoramic radiography, as shown in FIG. 12, the imaging region 128 is magnified 1.7 times, and the vicinity of the temporomandibular joints 139a, 139 is out of the imaging object, and only the dentition 81 is taken. In such dentition magnified panoramic radiography, the radiologist monitors the display unit 51 of the operation panel 19 in dentition standard panoramic radiography shown in FIG. 10, and operates the down cursor key 71 to move the setting condition from "radiographic site" to "mode," and presses the right cursor key 73 to change the parameter from "standard" to "magnified." As a result, the parameter display region 132e in the lowest stage is changed from "1.3 times" to "1.7 times." Thus, with the image magnification factor set at 1.7 times, the film cassette 21 is loaded in the operation procedure shown in FIG. 11, and the patient is positioned and the dentition magnified panoramic radiography is done.

Figure 15:
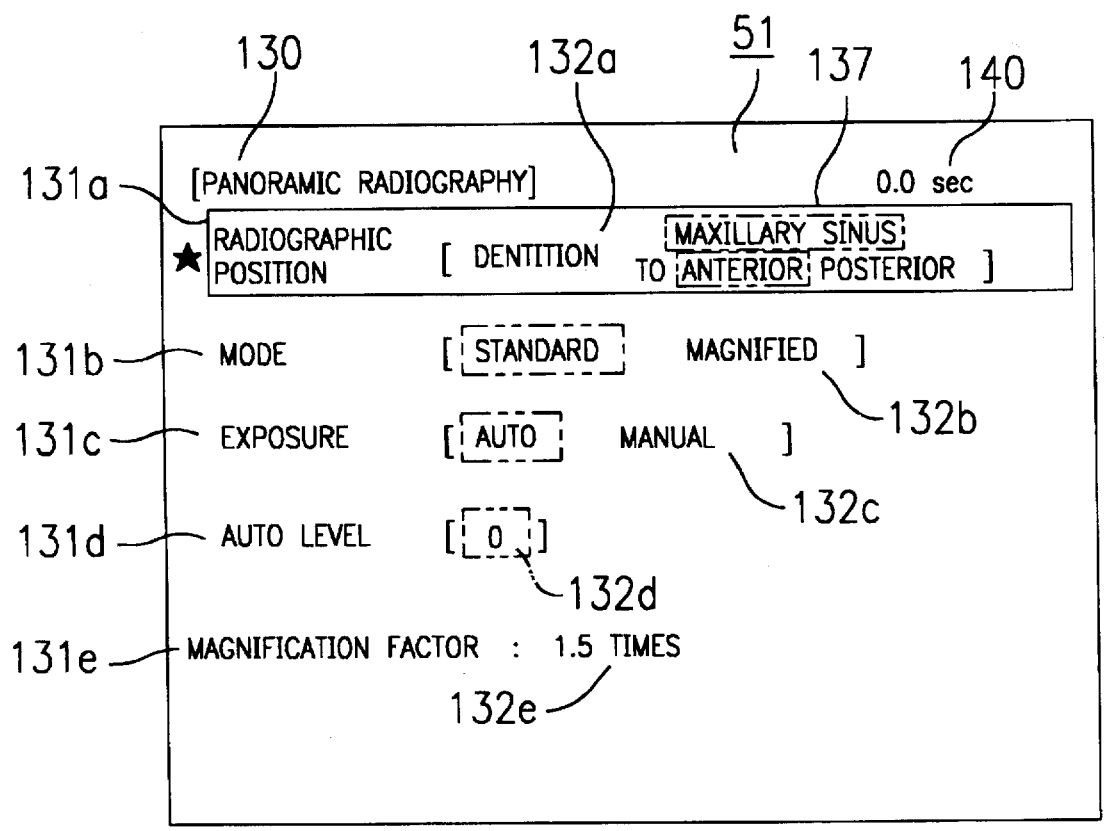
FIG. 15 is a diagram showing display data of the display unit 51 of maxillary sinus panoramic radiography.

FIG. 14 is a diagram showing the imaging regions 128a, 128b of the anterior and posterior sides of the maxillary sinus by maxillary sinus panoramic radiography, FIG. 15 is a diagram showing the display state of the display unit 51 set in the anterior side of the maxillary sinus, and FIG. 16 is a flow chart for explaining the operation procedure of maxillary sinus panoramic radiography.

The maxillary sinus panoramic radiography is available in maxillary sinus anterior panoramic radiography shown in the imaging region 128a in FIG. 4A, and maxillary sinus posterior panoramic radiography shown in the imaging region 128b in FIG. 4B, and when the main power switch 41 is pressed, "panoramic radiography" is displayed in the radiographic mode display region 130, and therefore the down cursor key 71 is pressed to move the frame display 137 to "radiographic site" and the right cursor key 73 is pressed to move the cursor 138 in the parameter display region 132a from "dentition" to "maxillary sinus," "anterior," thereby setting in the maxillary sinus anterior panoramic radiography. The parameters of the remaining setting conditions of mode, exposure and auto level remain at "standard," "auto" and "0", respectively. In this case, the magnification factor is automatically set to be 1.5 times. In the case of maxillary sinus posterior panoramic radiography, after moving the display frame 137 to "radiographic site," the right cursor key 73 is pressed to change the parameter from "anterior" to "posterior."

After thus setting the setting conditions by the operation panel 19, the operation proceeds to step b1. At step b1, the film cassette 21 is loaded into the other end 1b of the swivel arm 1, and the same as at steps a1–a6 in FIG. 11, the operations at steps b1–b6 are carried out, and after preparing for the radiography, at step b7, the patient is seated on the chair 6, and the ascending/descending main body 2 is moved at step b8 to adjust the height of the chin rest 17 to the jaw of the patient, and the patient bites a mouthpiece at step b9. At step b10, the patient is introduced into the radiographic position, and the chin rest 17 is raised to put the jaw on at step b11, and the median line beam 34 is projected to the face of the patient at step b12, and the head of the patient is fixed by the jaw bone plate at step b13. At step b14, after adjusting the eye-ear horizontal beam 33 to the eye-ear plane, the patient frame 3 is fixed by the lock handle 9 at step b15. At step b16, the ascending/descending main body 2 is moved to adjust the irradiation field beam to the nose wings, and at step b17, adjusting the beam of the distance measuring sensor to the center of the mouthpiece, any one of the edge-to-edge occlusion keys 82–85 is selected and pressed. At step b18, after making sure again that the ready lamp 45 is lighted, the irradiation button 47 is pressed to start radiographing at step b19. At this time, the X-ray exposure time is shown in the upper right corner of the screen of the display unit 51 as indicated by reference numeral 140. After thus finishing radiography, at step b20, a return switch, not shown in the drawing, provided at the side of the swivel arm 1 is pressed to return the swivel arm 1 to home position, and the film cassette 21 is unloaded at step b21 to terminate the radiographic operation.

Next, referring to Tables 2A, 2B, the linear tomography will be described.

TABLE 2A

Figure 17:
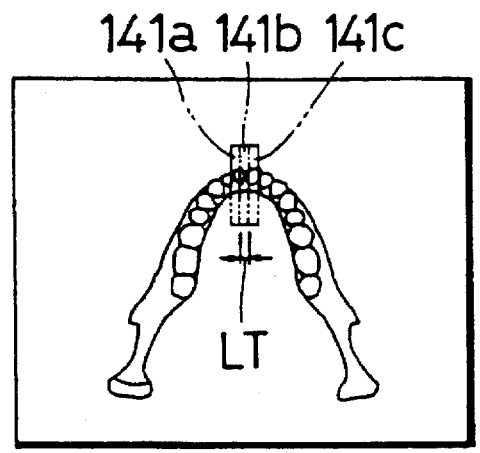
FIG. 17 is a diagram showing tomographic sections 141a–141c by jaw bone and dentition cross sectional linear tomography.
Figure 20:
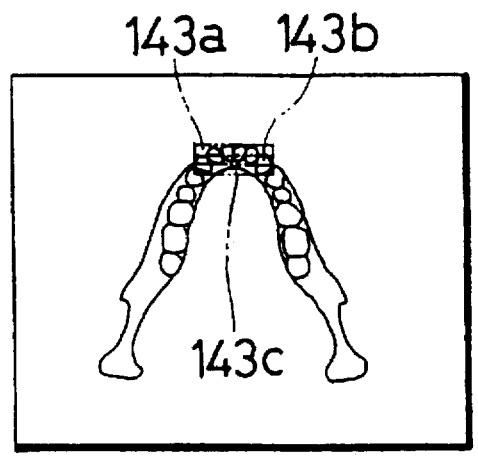
FIG. 20 is a diagram showing tomographic sections 143a–143c by jaw bone and dentition parallel plane linear tomography.
Figure 23:
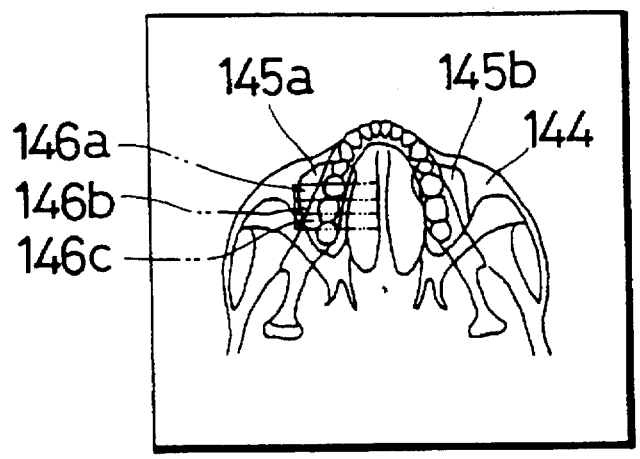
FIG. 23 is a diagram showing tomographic sections 146a–146c by maxillary sinus linear tomography.
Figure 26:
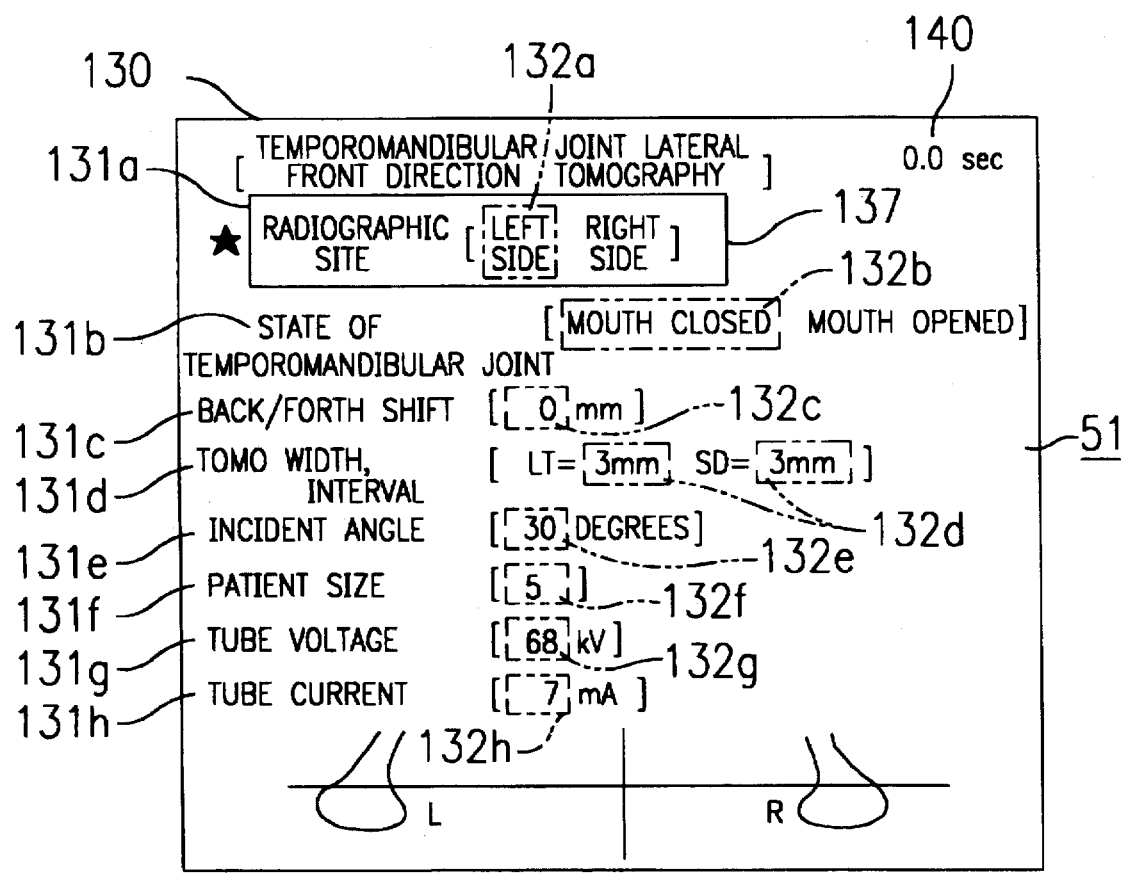
FIG. 26 is a diagram showing display data of the display unit 51 of temporomandibular joint frontal direction linear tomography.

| RADIOGRAPH TYPE | | PANORAMA FOR AREA SELECTION | KEY SELECTION | RADIOGRAPHIC CONDITION SETTING ON OPERATION PANEL | | | |
|---|---|---|---|---|---|---|---|
| | | | | MODE SELECTION | TOMO WIDTH, INTERVAL SETTING | EXPOSURE | AREA SELECTION |
| LINEAR TOMOGRAPHY | FIG. 17 | REQUIRED | "TOOTH CROSS SELECTION" KEY 55 | UPPER JAW LOWER JAW JAW BONES FOREHEAD | SELECTED FROM 3, 5, 7, 9 mm | DEPENDENT ON PATIENT SIZE | SELECT FROM SCALES 1–21 ON PANORAMIC FILM FOR AREA SELECTION |
| | FIG. 20 | REQUIRED | "DENTITION PARALLEL" KEY 56 | LINGUAL SIDE STANDARD BUCCAL SIDE | | | |
| | FIG. 23 | REQUIRED | "MAXILLARY SINUS" KEY 57 | FOREHEAD LATERAL OBLIQUE | | | |
| | FIG. 26 | NOT REQUIRED | "TEMPORO- MANDIBULAR FRONTAL DIRECTION" KEY 58 | (FRONTAL DIRECTION) LEFT MOUTH SIDE CLOSED RIGHT MOUTH SIDE CLOSED | | | SELECT INCIDENT ANGLE, DISTANCE |
| | FIG. 26 | NOT REQUIRED | "TEMPORO- MANDIBULAR LATERRAL KEY 59 | (LATERAL) LEFT MOUTH SIDE CLOSED RIGHT MOUTH SIDE CLOSED | | | |

TABLE 2B

Figure 6B:
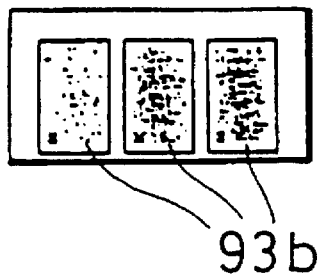

| RADIOGRAPH TYPE | | PATIENT POSITIONING | | | | | | X-RAY | |
|---|---|---|---|---|---|---|---|---|---|
| | | REFERENCE PLANE POSITION- ING | | PATIENT REST | IRRADI- ATION FIELD BEAM | TOMO- GRAPHIC BEAM | SECOND SLIT SELEC- TION | FILM (SENSITIZED PAPER) SELECTION | |
| LINEAR TOMOGRAPHY | FIG. 17 | EYE-EAR PLANE OR CAMPER'S PLANE | EAR ROD | CHIN REST | CENTOR OF EACH POSITION | AUTO FOCUS | FIG. 5B | FIG. 6B | |
| | FIG. 20 | EYE-EAR PLANE | JAW BONE PLATE | | | | | FIG. 6B | |
| | FIG. 23 | | | | NOSE WINGS | | | FIG. 6B | |
| | FIG. 26 | | EAR ROD | CHIN REST OF SUBNASAL POINT REST | HIGHEST POSITION OF IRRADIATION FIELD | APPARATUS MOVES AUTO- MATICALLY | FIG. 5B | FIG. 6B | |
| | FIG. 26 | | | | | | | FIG. 6B | |

Figure 18:
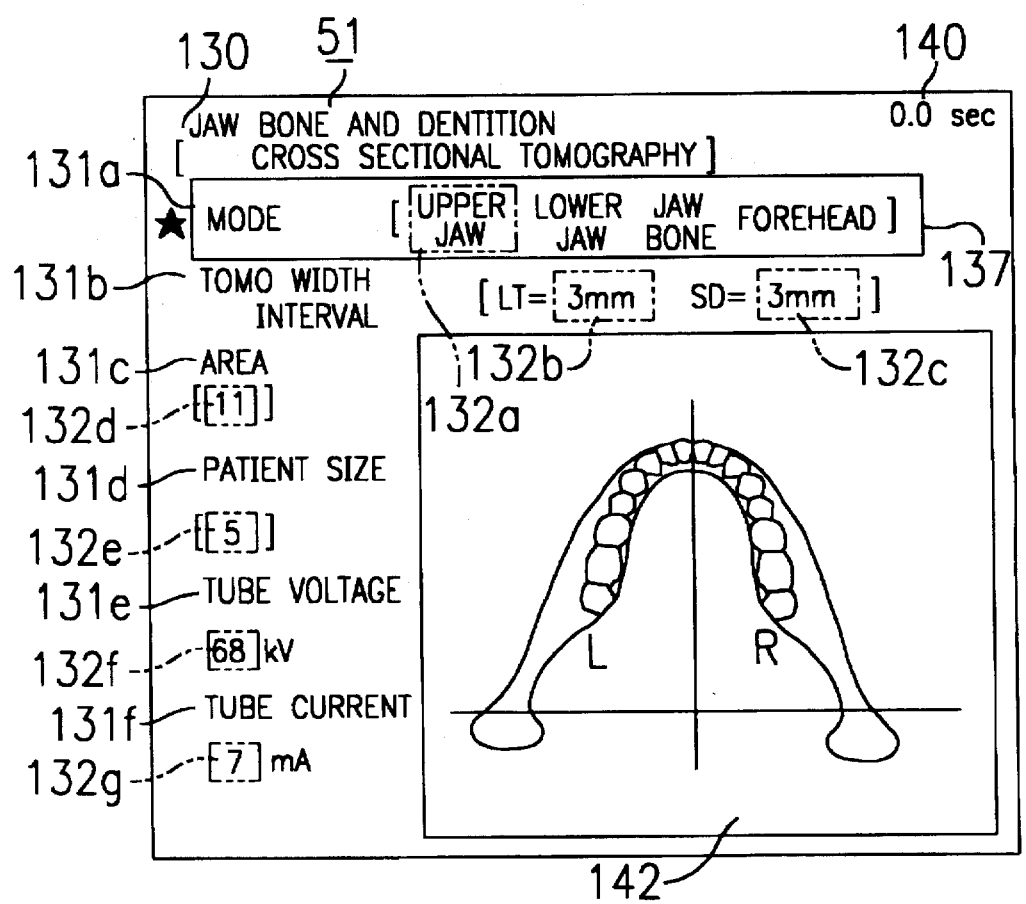
FIG. 18 is a diagram showing display data of the display unit 51 of jaw bone and dentition cross sectional linear tomography.

FIG. 17 is a diagram showing the imaging region by jaw bone and dentition cross sectional linear tomography, FIG. 18 is a diagram showing display data of the display unit 51, and FIG. 19 is a flow chart for explaining the operation procedure of jaw bone and dentition cross sectional linear tomography. In jaw bone and dentition cross sectional linear tomography, three tomographic images are obtained as indicated by virtual lines 141a–141c in FIG. 7. In this radiography, in order to select the tomographic position, the dentition standard panoramic radiography and dentition magnified panoramic radiography explained in relation to FIGS. 9–16 are required.

In order to operate the operation panel 19, first, the "tooth cross section" key 55 is pressed to display "jaw bone and dentition cross sectional tomography" in the radiographic mode display region 131 of the display unit 51, and a desired one is selected from the parameters "upper jaw," "lower jaw," "jaw bone," and "forehead" corresponding to the setting condition "mode" enclosed by the frame display 137, by using the cursor 138 with left cursor key 72 and right cursor key 73. In this embodiment, the cursor 138 indicates "upper jaw," and then the down cursor key 71 is pressed to change the frame display 137 to "tomo width, interval." The parameter LT indicates the width and the parameter SD indicates the moving interval. In the display unit 51 of the operation panel 19, there is an illustration display region 142 for schematically showing the radiographically related information including the radiographic site, projection angle and tomographic form in figures and characters. In the illustration display region 142, the tomographic plane displays 141a–141c can be moved along the dentition 81. The width LT and interval SD can be selected in four stages of 3, 5, 7 and 9 mm.

Next, pressing the down cursor key 71, the frame display 137 is moved to "area," and the radiographic position is selected. As the radiographic position, the position of the tomographic planes 141a–141c shown in FIG. 17 moving along the jaw bone and dentition can be selected, and the radiographic positions of the upper and the lower jaw can be changed in 21 stages of a range of 1 to 21 by one stage. The radiographic positions of jaw bones and a forehead can be set by moving the radiographic position in 14 stages of the ranges of 1 to 7 and 15 to 21 by one stage. Consequently, by pressing the down cursor key 71, the frame display 137 is moved to the "patient size." As the patient size, the size suited to the patient can be set in 10 stages of a range of 0 to 9 by one stage. By further pressing the down cursor key 71, the frame display 137 moves to "tube voltage," and the value of its parameter display region 132f can be set by 2 kV increment or decrement in a range of 60 to 80 kV. By pressing the down cursor key 71 furthermore, the frame display 137 moves to "tube current," and the value can be set in its parameter display region 132g by increasing or decreasing by 1 mA in six stages of a range of 5 to 10 mA.

After setting the radiographic conditions by the operation panel 19 in this manner, preparation for radiography is started. In this jaw bone and dentition cross sectional linear tomography, to select the imaging region, the panoramic radiography explained in relation to FIGS. 9–16 is conducted in advance. The operation procedure is described below.

At step c1, the panoramic film is developed, and the film is read and the imaging region is selected at step c2. At step c3, the film cassette 21 is loaded in the other end 1b of the swivel arm 1. This film cassette 21 contains a low sensitivity X-ray film for tomography 92 shown in FIG. 6 B. At step c4, it is confirmed that the chin rest 17 is at the lowest position, and at step c5, it is confirmed that the ready lamp 45 is lighted. At step c6, the slit plate 22 is changed from the narrow gap slit 90 shown in FIG. 5A to the wide slit 91, and it is confirmed at step c7 that the arrow 134 of the ascending/descending main body 2 coincides with the value 0 of the graduation 135 of the patient frame 3, and the jaw bone plate is removed at step c8, and is replaced with the ear rods 29, 30.

In positioning the patient, at step c9, the patient is seated on the chair 6, and the height is adjusted at step c10 so that the ear rods 29, 30 may coincide with the ear holes of the patient, and the patient bites a mouthpiece at step c11, and the patient is introduced into the radiographic position at step c12. At step c13, the chin rest 17 is raised to put the jaw on, and the face of the patient is fitted to the median line beam 34 at step c14, and the ear rods 29, 30 are inserted into the ear holes at step 15, and the patient is fixed. At step c16, the eye-ear level or Camper's plane is adjusted to the eye-ear horizontal beam 33, and the patient frame 3 is fixed with the lock handle 9 at step c17, and the irradiation field beam is adjusted to the center of each position to be taken at step c18, and the position sensor beam is fitted to the center of the mouthpiece at step c19, and one of the edge-to-edge occlusion keys 82–85 suited to the patient is pressed. At step c20, making sure again that the ready lamp 45 is lighted, the irradiation button 47 is pressed at step c21, thereby starting radiography. When radiography is over, at step c22, the swivel arm 1 is returned to home position, and the film cassette 21 is unloaded at step c23 to terminate the radiographic operation.

Figure 21:
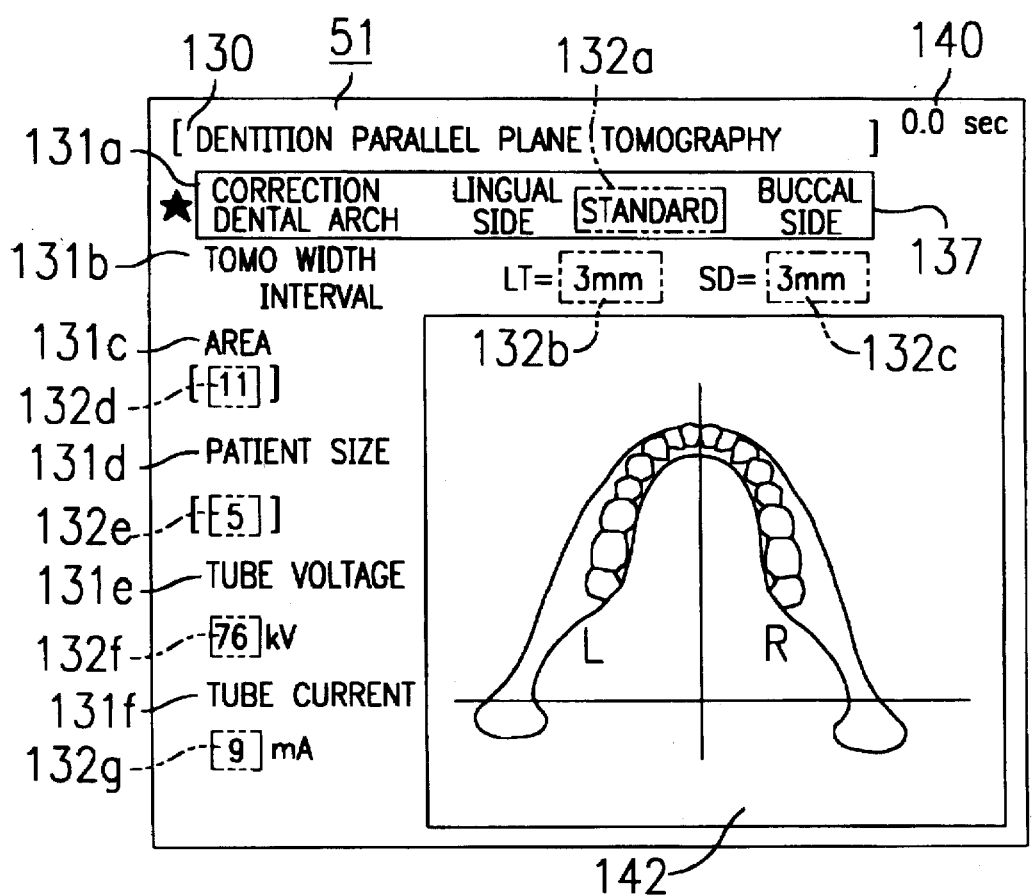
FIG. 21 is a diagram showing display data of the display unit 51 of jaw bone and dentition parallel plane linear tomography.

FIG. 20 is a diagram showing imaging regions by jaw bone and dentition parallel plane linear tomography, FIG. 21 is a diagram showing display data of the display unit 51 of jaw bone and dentition parallel plane linear tomography, and FIG. 22 is a flow chart for explaining the operation procedure of jaw bone and dentition parallel plane linear tomography. In the jaw bone and dentition parallel plane linear tomography of the embodiment, as shown in FIG. 20, tomographs of three sections 143a, 143b, 143c parallel to the jaw bone and dentition are taken.

When the "dentition parallel" key 56 is pressed, the display unit 51 shows as shown in FIG. 21. That is, in the radiographic mode display region 131, "dentition parallel plane tomography" is displayed, the frame display 137 shows "correction dental arch," and the radiographic position is selected at lingual side, standard or buccal side by operating the left cursor key 72 or right cursor key 73. By pressing the down cursor key 71, the frame display 137 is changed to the "tomo width, interval," and the tomographic width LT and the interval SD are set in the same manner as in the jaw bone and dentition cross sectional linear tomography. Similarly, thereafter, parameters of setting conditions of area, patient size, tube voltage, and tube current are set, and the radiographic condition setting by the operation panel 19 is complete.

In the subsequent process of preparation for radiography, first, in order to select the imaging region, the panoramic radiography as mentioned above is conducted. At step d1, the panoramic film is developed, and the imaging region is selected in the film at step d2. At step d3, the film cassette 21 is loaded into the other end 1b of the swivel arm 1. At this time, the X-ray film for tomography 92 shown in FIG. 6B is contained in the film cassette 21. At step d4, it is checked that the chin rest 17 is at the lowest position, and at step d5 it is confirmed that the ready lamp 45 is lighted, at step d6 the slit of the slit plate 22 is changed to the wide slit 91, and at step d7 it is confirmed that the arrow 134 of the ascending/descending main body 2 is matched with value 0 of the graduation 134 of the patient frame 3.

Next the operation of positioning the patient is conducted. At step d8, the patient is seated on the chair 6, the height of the chin rest 17 is adjusted to the jaw of the patient at step d9, and the patient bites a mouthpiece at step d10, and at step d11 the patient is introduced into the radiographic position. The operation advances to step d12 in this state, where the chin rest 17 is raised to put the jaw on, and adjusting to the median line beam 34 is conducted at step d13. The patient is fixed by the jaw bone plate at step d14, and the eye-ear plane is adjusted to the eye-ear horizontal beam 33 at step d15. The patient frame 3 is fixed by the lock handle 9 at step d16, and the irradiation field beam is adjusted to the center of each position to be taken at step d17. After the position sensor beam is fitted to the center of the mouthpiece at step d18, one of the edge-to-edge occlusion keys 82–85 suited to the patient is pressed, and it is confirmed again at step d19 that the ready lamp 45 is lighted, thereafter at step d20 the irradiation button 47 being pressed to start radiographing. After the completion of radiographing, the operation goes to step d21, where the swivel arm 1 returns to home position. The film cassette 21 is unloaded at step d22, thereby finishing the radiographic operation.

Figure 24:
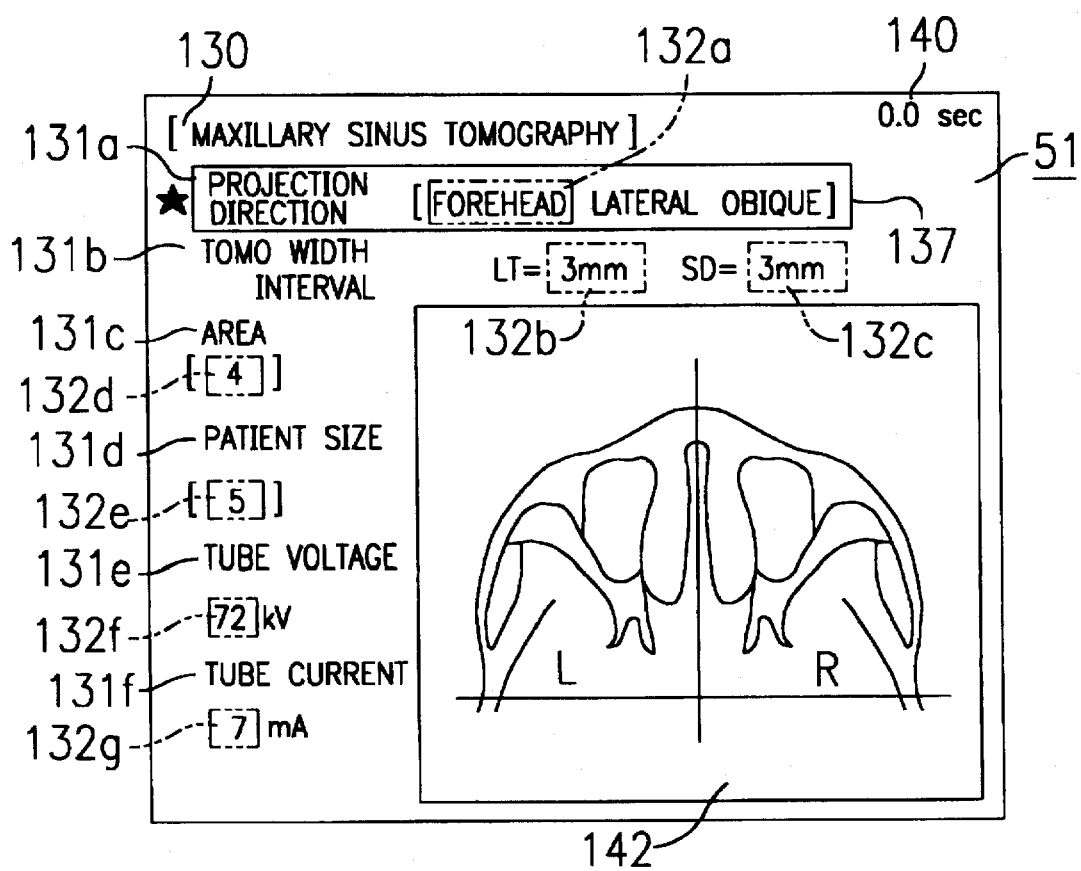
FIG. 24 is a diagram showing display data of the display unit 51 of maxillary sinus linear tomography.

FIG. 23 is a diagram showing the imaging regions by maxillary sinus linear tomography, and FIG. 24 is a diagram showing display data of the display unit 51 of maxillary sinus linear tomography. The operation procedure of the maxillary sinus linear tomography is same as that of the jaw bone and dentition parallel plane linear tomography, and hence the explanation about the operation procedure is omitted by citing the flow chart in FIG. 22. In the maxillary sinus linear tomography, as shown in FIG. 23, to take the plane tomographic images in the vicinity of the maxillary sinus 145a, 145b of the maxilla 144, three sections 146a, 146b, 146c are taken the same as in the jaw bone and dentition cross sectional linear tomography and jaw bone and dentition parallel plane linear tomography. The operating procedure of the operation panel 19 will be described below.

First, when the "maxillary sinus" key 57 is pressed, the "maxillary sinus tomography" is displayed in the radiographic mode display region 130 of the display unit 51, and the frame display 137 indicates the setting condition of "projection direction." In this state, the forehead, lateral, or oblique is selected by the left cursor key 72 and right cursor key 73, and the down cursor key 71 is pressed. As a result, the frame display 137 is moved to the display region 131b of setting conditions of "tomo width, interval," and the parameters are set. As the parameters, the tomographic width LT and interval SD are set, which can be respectively selected in four stages of 3, 5, 7, and 9 mm by the left cursor key 72 and right cursor key 73. When the down cursor key 71 is pressed again, the frame display 137 moves to the setting condition display region 131c displaying the "area," and same as above the three sections 146a–146c are moved and set in eight stages 4–7, 15–18. Such move of the sections 146a–146c can be effected by using the left cursor key 72 and right cursor key 73.

Then the down cursor key 71 is pressed, and the frame display 137 moves sequentially to each setting condition display region, and the parameters of patient size, tube voltage and tube current are set. In this case, the tube voltage is automatically set at 72 kV when the patient size is set at 5, and the tube current is automatically set at 7 mA when the patient size is set at 5. These parameters of patient size, tube voltage and tube current can be selected by the left cursor key 72 and right cursor key 73.

Figure 25:
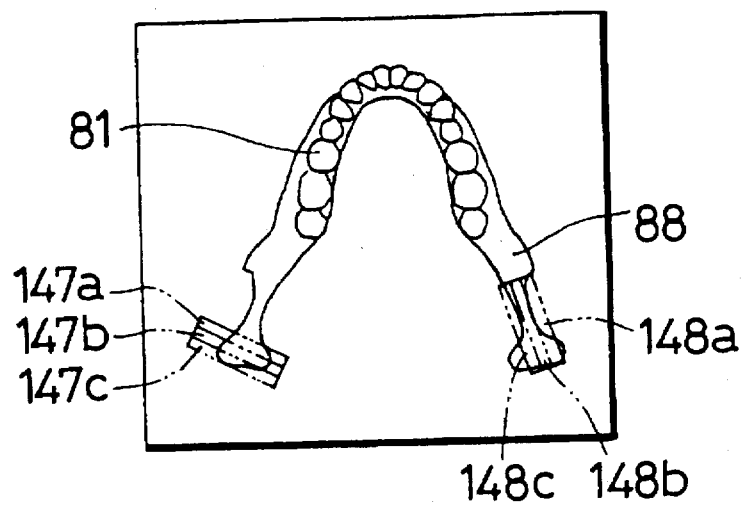
FIG. 25 is a diagram showing tomographic sections 147a–147c, 148a–148c by temporomandibular joint frontal direction linear tomography.
Figure 27:
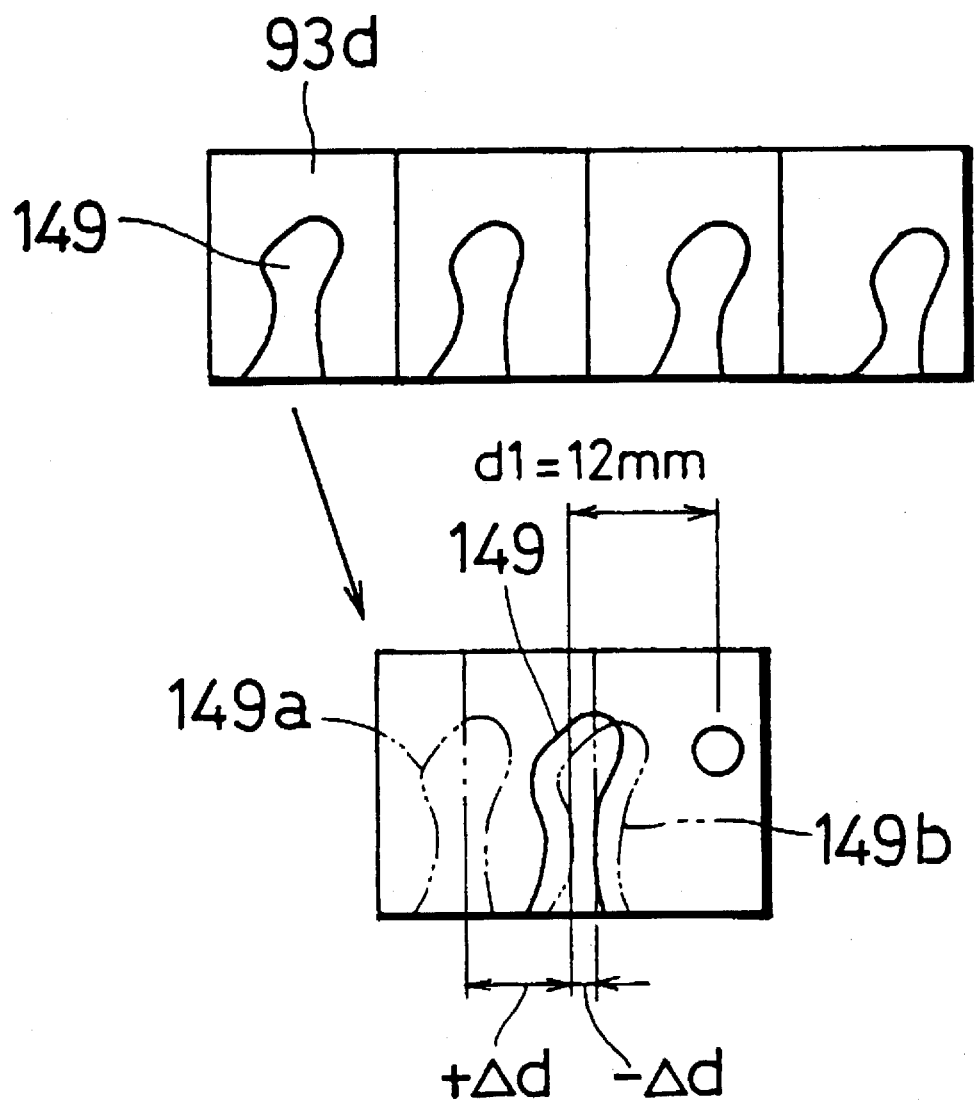
FIG. 27 is a diagram showing the state of the temporomandibular joint head deviated back and forth from the center of ear rods 29, 30.

FIG. 25 is a diagram showing the imaging regions by temporomandibular joint frontal direction linear tomography, FIG. 26 is a diagram showing display data of the display unit 51 of temporomandibular joint frontal direction linear tomography, FIG. 27 is a diagram showing the state of the temporomandibular joint head deviated back and forth from the center of ear rods 29, 30, and FIG. 28 is a flow chart for explaining the operation procedure of temporomandibular joint frontal direction linear tomography.

In the temporomandibular joint frontal direction linear tomography, as shown in FIG. 25, three sections each 147a–147c, 148a–148c are taken. The operation procedure of the operation panel 19 is described below. First, the "temporomandibular joint frontal direction" key 58 is pressed, and "temporomandibular joint front direction tomography" is displayed in the radiographic mode display region 130 of the display unit 51, and the frame display 137 shows "radiographic site." After setting the radiographic site to "left side" or "right side" by manipulating the left cursor key 72 and right cursor key 73, the down cursor key 71 is pressed to move the frame display 137 to the next setting condition "state of temporomandibular joint," and the parameter is selected at "mouth closed" or "mouth opened" by manipulating the left cursor key 72 and right cursor key 73. The down cursor key 71 is further pressed to move the frame display 137 to the next setting condition "back/forth shift", and back and forth shifts are set by operating the left cursor key 72 and the right cursor key 73.

When setting of back and forth shifts is thus over, the down cursor key 71 is pressed, and the frame display 137 is moved to the next setting condition "tomo width, interval," and the tomographic width LT and interval SD are set in the parameter display region 132d by using the left cursor key 72 and right cursor key 73. Furthermore, pressing the down cursor key 71, the frame display 137 is moved to the next setting condition "incident angle," and the incident angle is set in the parameter display region 132e. The incident angle can be selected in eight stages of 0, 5, 10, 15, 20, 5, 30, and 35 (degrees), and is determined according to the X-ray image 93d of the X-ray film 92 taken by the temporomandibular joint head angle measuring radiography. Similarly, thereafter, the remaining setting conditions of patient size, tube voltage and tube current are set by using the down cursor key 71, left cursor key 72, and right cursor key 73.

Referring now to FIG. 23, the operation procedure will be explained below. First at step e1, the film cassette 21 is loaded into the other end 1b of the swivel arm 1. The film cassette 21 contains an X-ray film 92 shown in FIG. 6B. At step e2, it is checked that the chin rest 17 is at the lowest position, and it is confirmed at step e3 that the ready lamp 45 is lighted. At step e4, the slit plate 22 is changed to a wide slit 91 shown in FIG. 5B, and the arrow 134 of the ascending/descending main body 2 is checked to be matched with value 0 of the graduation 135 of the patient frame 3 at step e5, the jaw bone plate is removed at step e6 to replace with the ear rods 29, 30, and the chin rest 17 is removed at step e7 to replace with a subnasal point rest prepared separately.

When the preparation for radiography is thus completed, the patient is positioned. At step e8, the patient is seated on the chair 6, and the height of the ear rods 29, 30 is adjusted to the ear holes of the patient at step e9, and the patient is introduced into the radiographic position at step e10. At step e11, the subnasal point rest is adjusted to the subnasal point of the patient, and the patient occludes spontaneously at step e12, the median line beam is adjusted at step e13, and the ear rods 29, 30 are inserted into the ear holes at step e14 to fix the patient.

Furthermore, at step e15, the eye-ear plane is adjusted to the eye-ear horizontal beam 33, and the patient frame is fixed by the lock handle 9 at step e16, the irradiation field beam is adjusted to the highest position of the irradiation field at step e17, and it is confirmed again at step e18 that the ready lamp 45 is lighted. If lighted, the operation goes to step e19, where the irradiation button 47 is pressed to start radiographing. When the radiographing is thus finished, the operation goes to step e20, where the swivel arm 1 is returned to home position. The film cassette 21 is removed at step e21, and thereby the radiographic operation is terminated.

Figure 29:
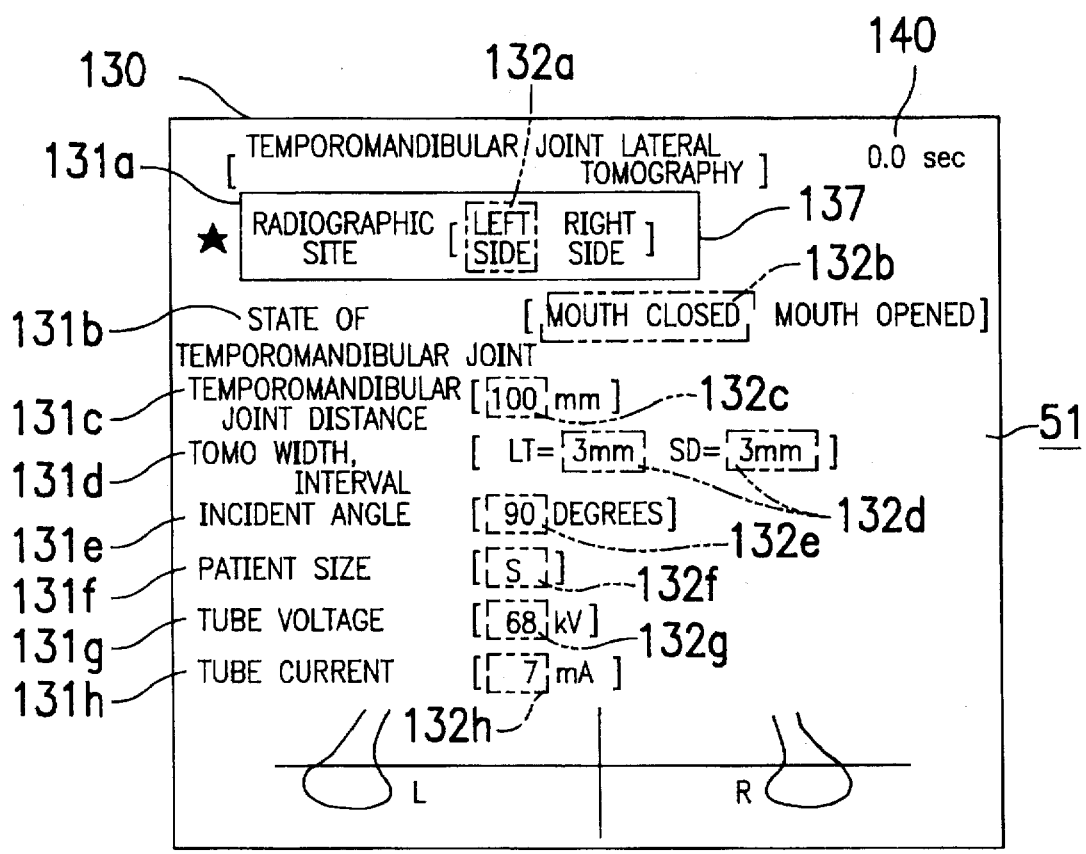
FIG. 29 is a diagram showing display data of the display unit 51 of temporomandibular joint temporal linear tomography.

FIG. 29 is a diagram showing display data of the display unit 51 of temporomandibular joint lateral linear tomography. The temporomandibular joint lateral linear tomography takes the same imaging region as the temporomandibular joint frontal direction linear tomography, and the imaging region is same as in FIG. 25, and the operation procedure is same as in FIG. 28. The operation procedure of the operation panel 19 is described below. First "temporomandibular joint lateral" key 59 is pressed, and the display unit 51 shows, as shown in FIG. 29, "temporomandibular joint lateral tomography" in the radiographic mode display region 130, and the frame display 137 is displayed in the "radiographic direction" of the uppermost setting condition display region 131a, In the parameter display region 132a, the radiographic direction is indicated by "left side" or "right side," and either can be selected by the left cursor key 72 or right cursor key 73, and the down cursor key 71 is pressed to move the frame display 137 to the next setting condition "state of temporomandibular joint." Herein, the "mouth closed" and "mouth opened" showing the state of the temporomandibular joint are displayed in the parameter display region 132b, and either can be selected by the left cursor key 72 or right cursor key 73. By pressing the down cursor key 71 again, the frame display 137 is moved to the next setting condition "temporomandibular joint distance," and the temporomandibular joint distance is set in the parameter display region 132c. The temporomandibular joint distance is determined by the temporomandibular joint distance measuring radiography mentioned later depending on the patient, out of five stages of 84 mm, 92 mm, 100 mm, 108 mm, and 116 mm.

The down cursor key 71 is further pressed to move the frame display 137 to the next setting condition "tomo width, interval," and the parameters, the tomographic width LT and interval SD, are selected by the left cursor key 72 and right cursor key 73. In succession, the down cursor key 71 is pressed to move the frame display 137 to the next setting condition "incident angle," and the incident angle is set in the parameter display region 132e. The incident angle is determined by the above temporomandibular joint head angle measuring radiography, out of eight stages of 55, 60, 65, 70, 75, 80, 90, 100.

By pressing the down cursor key 71 to lower the frame display 137, and the parameters corresponding to the setting conditions of patient size, tube voltage and tube current are set same as above, and the setting procedure by the operation panel 19 is over.

Figure 30A:
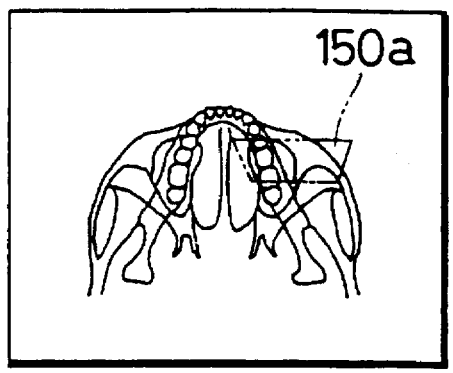
FIGS. 30A, 30B are diagrams showing imaging regions 150a, 150b, respectively, by maxillary sinus scanogram radiography.
Figure 30B:
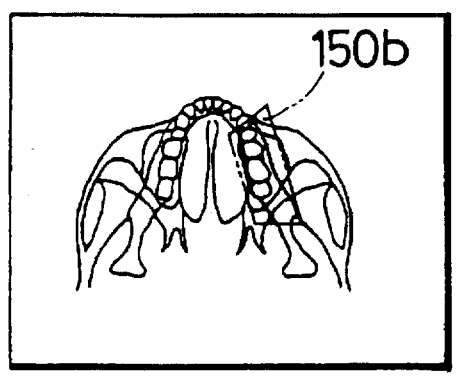
Figure 31:
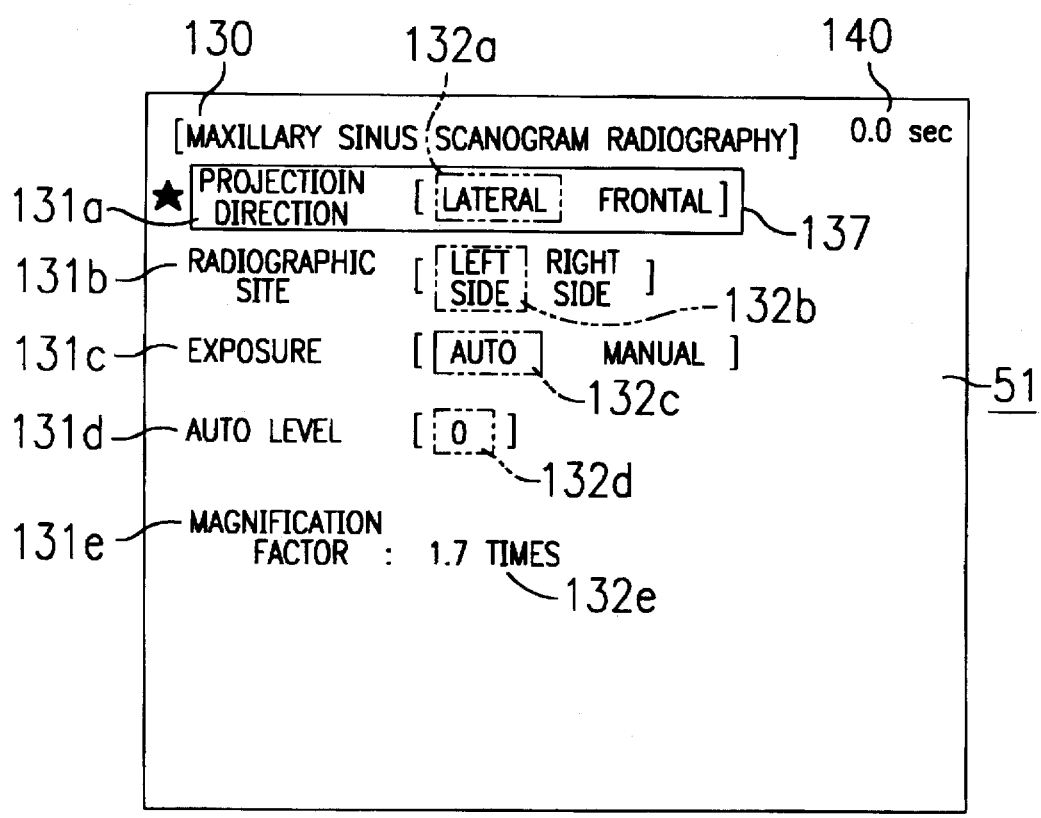
FIG. 31 is a diagram showing display data of the display unit 51 of maxillary sinus scanogram radiography.

The scanogram radiography is described below. The scanogram radiography is available in maxillary sinus scanogram radiography and temporomandibular joint scanogram radiography as shown in Table 3.

lary sinus scanogram radiography. The maxillary sinus scanogram radiography is available in two imaging directions, that is, lateral imaging region 150a shown in FIG. 30A, and frontal imaging region 150b shown in FIG. 30B. The operation procedure of the operation panel 19 is described. First, by pressing the "maxillary sinus" key 68, "maxillary sinus scanogram radiography" is displayed in the radiographic mode display region 130 as shown in FIG. 31 in the display unit 51, and the frame display 137 is displayed in the setting condition "projection direction." As the parameter of the imaging direction, either "lateral" or "frontal" is selected by the left cursor key 72 or right cursor key 73. By pressing the down cursor key 71, the frame display 137 is moved to the next setting condition "radiographic site," and the parameter is selected at "left side" or "right side" by the left cursor key 72 or right cursor key 73. By further pressing the down cursor key 71, the frame display 137 is moved to the lower setting condition display region 131, and is displayed in the setting condition "exposure," and the parameter is set in "auto" or "manual" by the left cursor key 72 or right cursor key 73. By pressing the down cursor key 71 once again, the frame display 137 moves to the lower setting condition "auto level," and the parameter is selected and set among nine stages at one-step increments from 4 to −4. At this time, the magnification factor is automatically set at 1.7 times. Meanwhile, when "manual" is selected in the setting condition "exposure," the setting conditions of tube voltage and tube current are displayed.

Figure 6C:
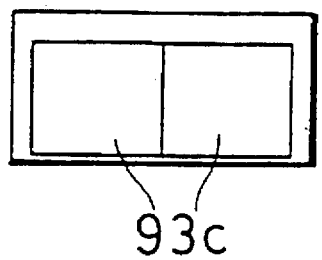

The operation procedure is described below. At step f1, the film cassette 21 is loaded into the other end 1b of the swivel arm 1. This film cassette 21 contains an X-ray film 92 as shown in FIG. 6C. At step f2, it is checked that the chin rest 17 is at the lowest position, and it is confirmed at step f3 that the ready lamp 45 is lighted. At step f4, the slit plate

TABLE 3

Figure 33:
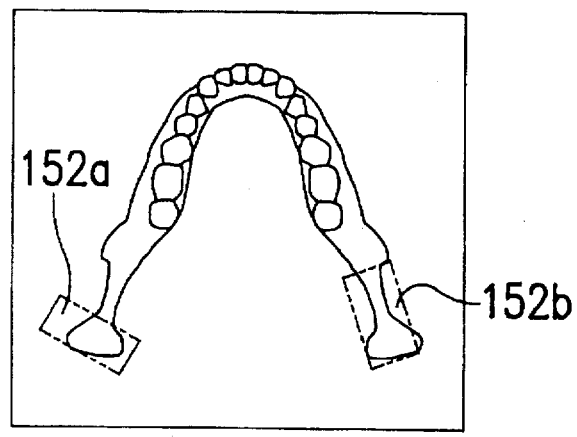
FIG. 33 is a diagram showing imaging regions 152a, 152b by temporomandibular joint scanogram radiography.

| RADIOGRAPH TYPE | | PANORAMA FOR AREA SELECTION | KEY SELECTION | RADIOGRAPHIC CONDITION SETTING ON OPERATION PANEL | | POSITIONING | |
|---|---|---|---|---|---|---|---|
| | | | | MODE SELECTION | EXPOSURE | REFERENCE PLANE POSITIONING | PATIENT REST |
| SCANOGRAM RADIOGRAPHY | FIG. 30 | NOT REQUIRED | "MAZILARY SINUS" KEY 57 | LATERAL FRONTAL | AUTO | EYE-EAR PLANE | JAW BONE PLATE CHIN REST |
| | FIG. 33 | NOT REQUIRED | "TEMPOROMANDIBULAR JOINT" KEYS 58, 59 | LATERAL FRONTAL | | | EAR ROD CHIN REST OR SUB-NASAL POINT REST |

Figure 6D:
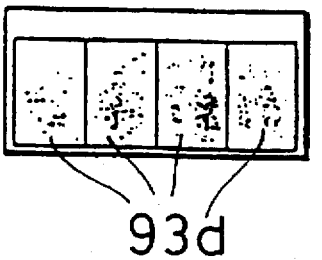
Figure 6E:
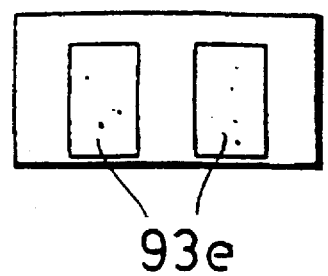

| RADIOGRAPHY TYPE | | PATIENT POSITIONING | | | X-RAY FILM |
|---|---|---|---|---|---|
| | | IRRADIATION FIELD BEAM | TOMOGRAPHIC BEAM | SECOND SLIT SELECTION | (SENSITIZED PAPER) SELECTION |
| SCANOGRAM RADIOGRAPHY | FIG. 30 | NOSE WINGS | AUTO FOCUS | FIG. 5A | FIG. 6C |
| | FIG. 33 | HIGHEST POSITION ON IRRADIATION FIELD | APPARATUS MOVES AUTOMATICALLY | | FIG. 6D FIG. 6E |

FIG. 30 is a diagram showing imaging regions 150a, 150b by maxillary sinus scanogram radiography, FIG. 31 is a diagram showing display data of the display unit 51 of maxillary sinus scanogram radiography, and FIG. 32 is a flow chart for explaining the operation procedure of maxil- 22 is changed to the narrow gap slit 90 shown in FIG. 5A, and it is checked at step f5 that the arrow 134 of the ascending/descending main body 2 is matched with value 0 of the graduation 135 of the patient frame 3, thereby finishing the preparation for radiography.

At step f6, the patients is seated on the chair 6, and the height of the chin rest 17 is adjusted to the jaw of the patient at step f7, and the patient bites a mouthpiece at step f8, and the patient is introduced into the radiographic position at step f9. At step f10, the chin rest 17 is raised to put the jaw on, and the median line beam 34 is adjusted to the median line of the patient at step f11, the patient is fixed by the jaw bone plate at step f12, and the eye-ear plane of the patient is adjusted to the eye-ear horizontal beam 33 at step f13. Afterwards, at step f14, the patient frame 3 is fixed by the lock handle 9, and the ascending/descending main body 2 is moved at step f15 to adjust the irradiation field beam to the nose wings, and the position sensor beam is adjusted to the center of the mouthpiece at step f16, and one of the edge-to-edge occlusion keys 82–85 corresponding to the patient is selected and pressed. At step f17, it is confirmed again that the ready lamp 45 is lighted, the irradiation button 47 is pressed at step f18, thereby starting the scanogram radiography of the maxillary sinus according to the radiographic condition set by the operation panel 19.

When radiography is over, at step f19, the swivel arm 1 is returned to home position, and the film cassette 21 is unloaded at step f20, thereby finishing the radiographic operation.

Figure 34:
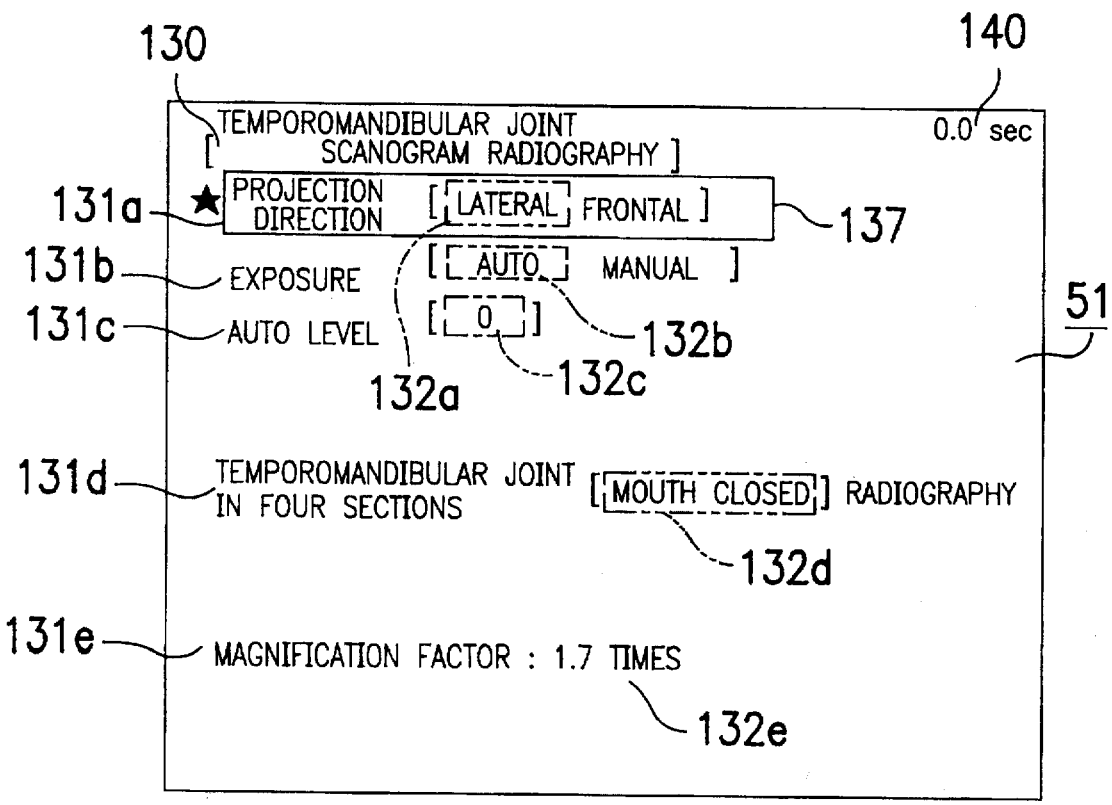
FIG. 34 is a diagram showing display data of the display unit 51 of temporomandibular joint scanogram radiography.

FIG. 33 is a diagram showing imaging regions 151a, 151b by temporomandibular joint scanogram radiography, FIG. 34 is a diagram showing display data of the display unit 51 of temporomandibular joint scanogram radiography, and FIG. 35 is a flow chart for explaining the operation procedure of temporomandibular joint scanogram radiography. In the temporomandibular joint scanogram radiography, the temporomandibular joint is taken in one film by four divisions, that is, right and left positions with the mouth opened, and right and left positions with the mouth closed. The operation procedure of the operation panel 19 is described below. First, when the "temporomandibular joint" key is pressed, the "temporomandibular joint scanogram radiography" is displayed in the radiographic mode display region 130 as shown in FIG. 34 in the display unit 51, and the display frame 137 is displayed in the setting condition "projection direction." The parameter of the projection direction is either "lateral" or "frontal," which is selected by pressing the left cursor key 72 or right cursor key 73, and then the down cursor key 71 is pressed to move the frame display 137 to the next setting condition "exposure." Herein, either "auto" or "manual" is selected as the parameter, and the down cursor key 71 is pressed successively to move the frame display 137 to the next setting condition "auto level," and the parameter is set and selected from 4 to −4 same as in the manner above. When the down cursor key 71 is further pressed, the frame display 137 is changed to the next setting condition "temporomandibular joint in four sections." Herein, when radiography in the closed mouth position is over, it is automatically changed over to the open mouth radiography, and the "mouth open" is displayed in the parameter display region 132d. In such temporomandibular joint scanogram radiography, the magnification factor is preset at 1.7 times.

Referring to FIG. 35, the operation procedure is described. At step g1, the film cassette 21 is loaded into the other end 1b of the swivel arm 1. This film cassette 21 contains an X-ray film 92 shown in FIG. 6D because the projection direction is selected at the lateral side. When the projection direction is selected at the frontal side, an X-ray film 92 shown in FIG. 6E is contained. At step g2, it is checked that the chin rest 17 is at the lowest position, and it is confirmed at step g3 that the ready lamp 45 is lighted. At step g4, the slit plate 22 is changed to the narrow gap slit 90 shown in FIG. 5A, and it is checked at step g5 that the arrow 134 of the ascending/descending main body 2 is matched with value 0 of the graduation 135 of the patient frame 3, and the jaw bone plate is removed at step g6 to replace with the ear rods 29, 30, and the chin rest 17 is removed at step g7 to replace with the subnasal point rest.

When the preparation for radiography is thus completed, the operation goes to step g8, where the patient is seated on the chair 6, and the height of the ear rods 29, 30 is adjusted to the ear holes of the patient at step g9. The patient is brought into the radiographic position at step g10. At step g11, the subnasal point rest is adjusted to the subnasal point, and the patient occludes spontaneously at step g12. At step g13, the median line beam 34 is adjusted, and at step g14 the patient is fixed by inserting the ear rods 29, 30 into the ear holes. The eye-ear plane is adjusted by the eye-ear horizontal beam 33 at step g15, the patient frame 3 is fixed by the lock handle 9 at step g16, and the ascending/descending main body 2 is moved at step g17 to adjust the irradiation field beam to the highest position of the irradiation field.

When positioning the patient is thus over, the operation goes to step g18, where the patient closes the mouth, and it is confirmed at step g19 that the ready lamp 45 is lighted. The irradiation button 47 is pressed at step g20 to conduct the radiography according to the setting conditions of the operation panel 19.

When the temporomandibular joint radiography in closed mouth position is thus over, the operation goes to step g21, where the patient opens the mouth, and it is confirmed again at step g22 that the ready lamp 45 is lighted. The irradiation button 47 is pressed, if lighted, to radiograph the temporomandibular joint in the open mouth position. In this way, when the temporomandibular joint radiography in closed mouth position and open mouth position is over, at step g24 the swivel arm 1 is returned to home position, and the film cassette 21 is unloaded at step g25 to terminate the radiographic operation.

Figure 36:
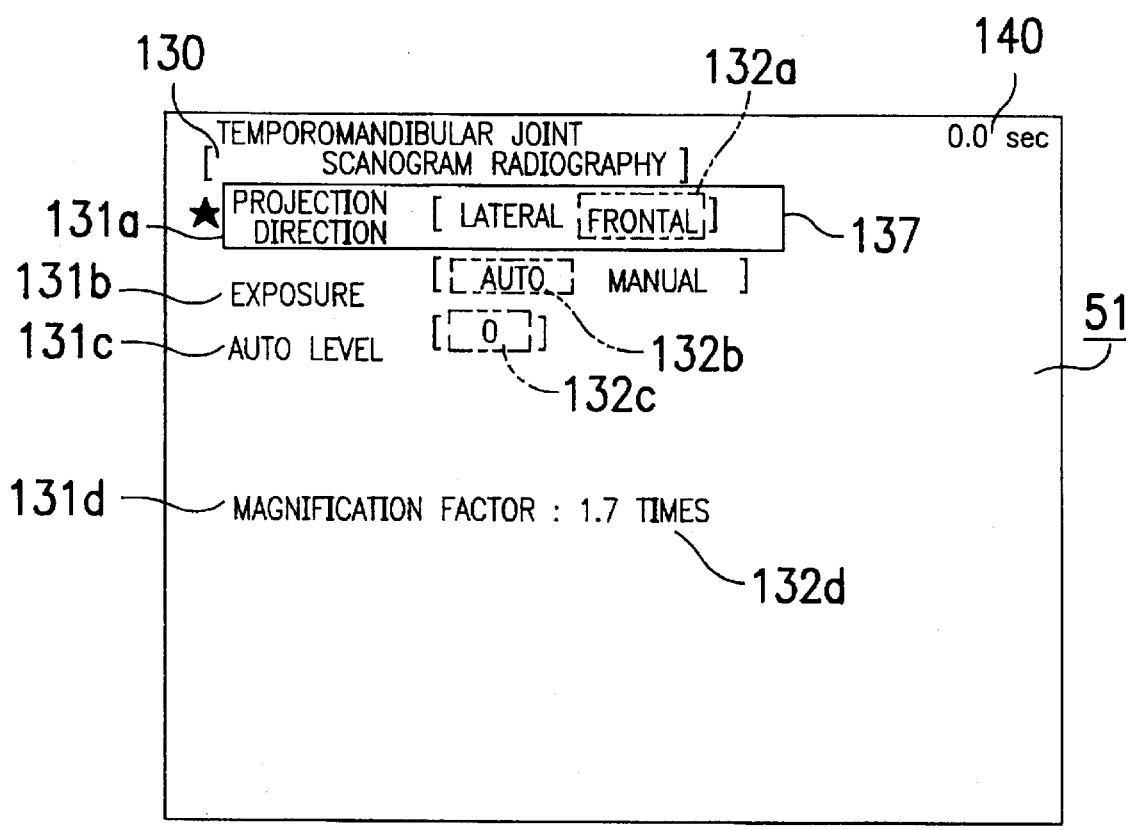
FIG. 36 is a diagram showing display data of the display unit 51 when the projection direction is set in the frontal side in temporomandibular joint scanogram radiography.

FIG. 36 is a diagram showing display data of the display unit 51 when the projection direction is set in the frontal side in temporomandibular joint scanogram radiography and FIG. 37 is a flow chart for explaining the operation procedure when the projection direction is set in the frontal side in temporomandibular joint scanogram radiography. In the temporomandibular joint scanogram radiography, when the projection direction is set at the frontal side, the right and left side of the temporomandibular joint are taken in the frontal direction in one film. The operation procedure of the operation panel 19 is described below. When the "temporomandibular joint" key 69 is pressed, the "temporomandibular joint scanogram radiography" is displayed in the radiographic mode display region 130 of the display unit 51 the same as mentioned above, and the frame display 137 is displayed in the setting condition "projection direction." Herein, by pressing the right cursor key 73, the parameter is changed from the "lateral" to the "frontal" side. Then, by pressing the down cursor key 71, the frame display 137 is moved to the next setting condition "exposure," and the parameter is selected in either "auto" or "manual." When the down cursor key 71 is further pressed, the frame display 137 moves to the next setting condition "auto level" and one level is selected from nine stages of 4 to −4 as mentioned above, and the setting operation is over. In this case, too, the magnification factor is set at 1.7 times.

The operation procedure is described below. Steps h1 to h7 are preparation for radiography same as in steps g1 to g7 in FIG. 35, and at subsequent steps h8–h17, the patient is positioned same as at steps g8 go g17 in FIG. 35, and it is confirmed at step h18 that the ready lamp 45 is lighted, and the irradiation button 47 is pressed at step h19 to start radiography of the temporomandibular joint in the frontal direction, and the swivel arm 1 is returned to home position at step h20, and the film cassette 21 is unloaded at step h21, thereby terminating the radiographic operation.

The skull liner scan radiography is described below. The skull linear scan radiography is available, as shown in Table 4, in the lateral radiography for projecting from the left side to the right side of the head of the patient, and the front radiography projecting from the posterior side to the anterior side (P/A radiography, and these lateral radiography and P/A radiography are described below.

21 is loaded in the other end 1b of the swivel arm 1. This film cassette 21 contains an X-ray film 92 shown in FIG. 6F, and it is checked at step i2 that the chin rest 17 is at the lowest position, and it is confirmed at step i3 that the ready lamp 45 is lighted, and the slit plate 22 is changed to the narrow gap slit 90 shown in FIG. 5A at step i4, the patient frame 3 is fixed by the lock handle 9 at step i5, and the arrow 134 of the ascending/descending main body 2 is matched with value 0 of the graduation 135 of the patient frame 3 at step i6, thereby setting the lock handle 9 at the panorama lock side.

When the preparation for radiography is thus over, the patient is seated on the chair 6 at step i7, and the ascending/descending main body 2 is moved at step i8 to adjust the height of the chin rest 17 to the jaw of the patient. The

TABLE 4

Figure 38:
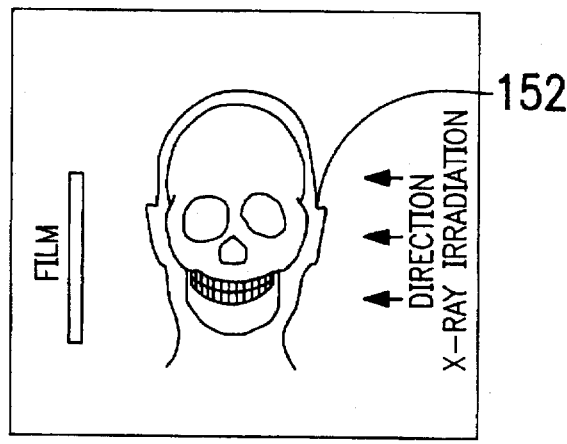
FIG. 38 is a diagram showing the imaging region 152 when the projection direction is set in the lateral direction in skull linear scanning radiography.
Figure 41:
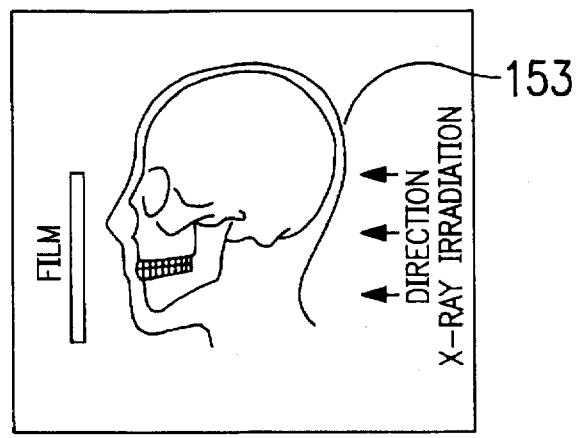
FIG. 41 is a diagram showing an imaging region 153 when the projection direction is set in the front direction in skull linear scanning radiography.

| RADIOGRAPH TYPE | PANORAMA FOR AREA SELECTION | KEY SELECTION | RADIOGRAPHIC CONDITION SET ON OPEARTION PANEL | | PATIENT POSITIONING | |
|---|---|---|---|---|---|---|
| | | | MODE SELECTION | EXPOSURE | REFERENCE PLANE POSITIONING | PATIENT REST |
| LINEAR SCAN RADIOGRAPHY | FIG. 38 FIG. 41 | NOT REQUIRED | "LINEAR SCAN" KEY 60 | LATERAL P/A | AUTO | EYE-EAR PLANE | JAW BONE PLATE | CHIN REST |

Figure 6F:
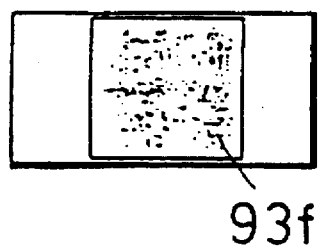
Figure 6G:
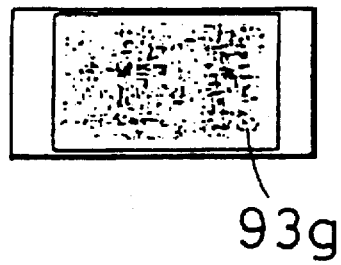

| RADIOGRAPH TYPE | PATIENT POSITIONING | | | X-RAY FILM (SENSITIZED PAPER) SELECTION |
|---|---|---|---|---|
| | IRRADIATION FIELD BEAM | TOMOGRAPHIC BEAM | SECOND SLIT SELECTION | |
| LINEAR SCAN RADIOGRAPHY FIG. 38 FIG. 41 | LOWER LIP LOWER EDGE | AUTO FOCUS | FIG. 5A | FIG. 6F FIG. 6G |

Figure 39:
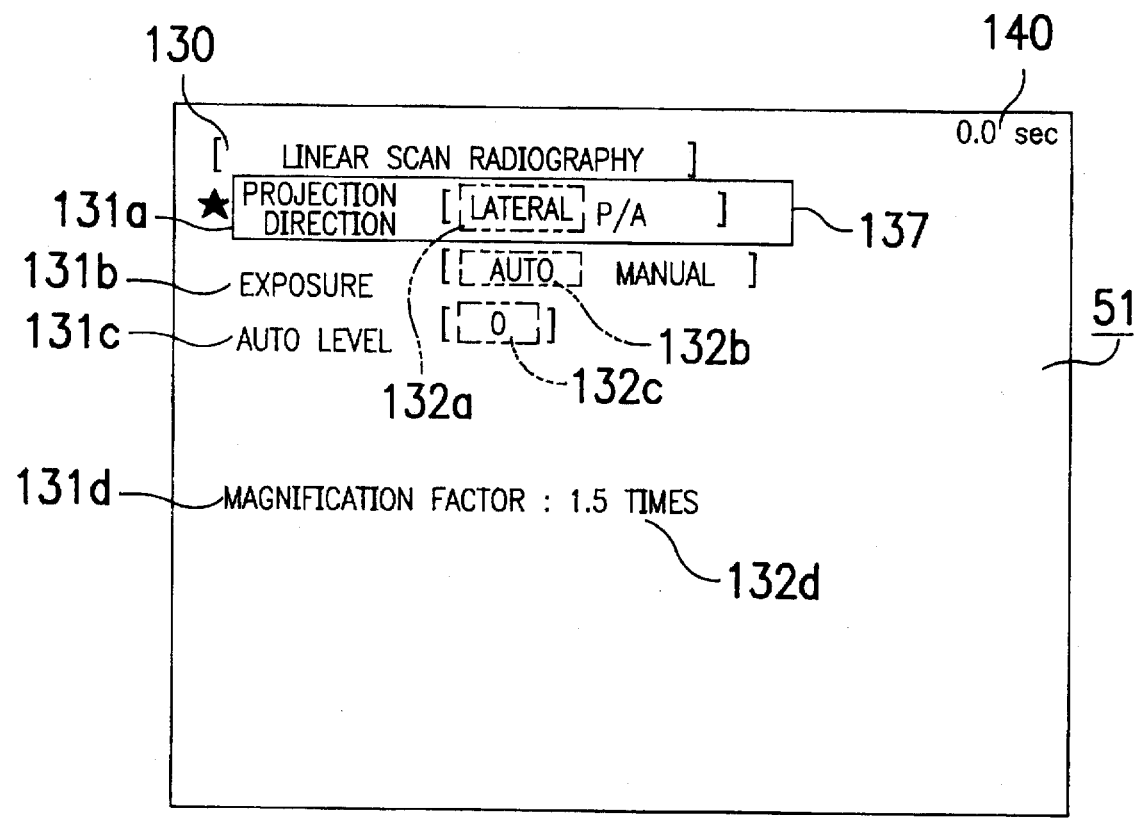
FIG. 39 is a diagram showing display data of the display unit when the projection direction is set in the lateral direction in skull linear scanning radiography.

FIG. 38 is a diagram showing the imaging region 152 when the projection direction is set in the lateral direction in skull linear scan radiography, FIG. 39 is a diagram showing display data of the display unit when the projection direction is set in the lateral direction in skull linear scan radiography, and FIG. 40 is a flow chart for explaining the operation procedure when the projection direction is set in the lateral direction in skull linear scan radiography. In the skull linear scan radiography, the projection direction is lateral, that is, it is intended to obtain the projected image from the left side to the right side of the head of the patient. The operation procedure of the operation panel 19 is described. When the "linear scan" key 60 is pressed, the "linear scan radiography" is displayed in the radiographic mode display region 130 in the display unit 51, and the frame display 137 is displayed in the setting condition "projection direction." Parameters of the projection direction are available in "lateral" and "P/A," and either can be selected by the left cursor key 72 or right cursor key 73 same as above. By pressing the down cursor key 71, the frame display 137 is moved to the next setting condition "exposure," and the parameter "auto" or "manual" is selected. In succession, the down cursor key 71 is pressed, then the frame display 137 is moved to the next setting condition "auto level," and one of nine stages from 4 to −4 is selected in the same manner as above, and the setting operation is over. In this skull linear scan radiography, the magnification factor is automatically set at 1.5 times.

The operation procedure when the projection direction is set at lateral is described below. At step i1, the film cassette patient is brought into the radiographic position at step i9, and at step i10 the chin rest 17 is raised to put the jaw on. The median line beam 34 is adjusted at step i11, the patient is fixed by the jaw bone plate at step i12, the eye-ear plane is adjusted to the eye-ear horizontal beam 33 at step i13, it is confirmed at step i14 that the irradiation field beam is at the lower limb lower edge, and at step i15 it is confirmed again that the ready lamp 45 is lighted. When lighted, at step i16 the irradiation button 47 is pressed to perform radiography. At step i17, the swivel arm 1 is returned to home position, and the film cassette 21 is unloaded to terminate the radiographic operation is over.

Figure 42:
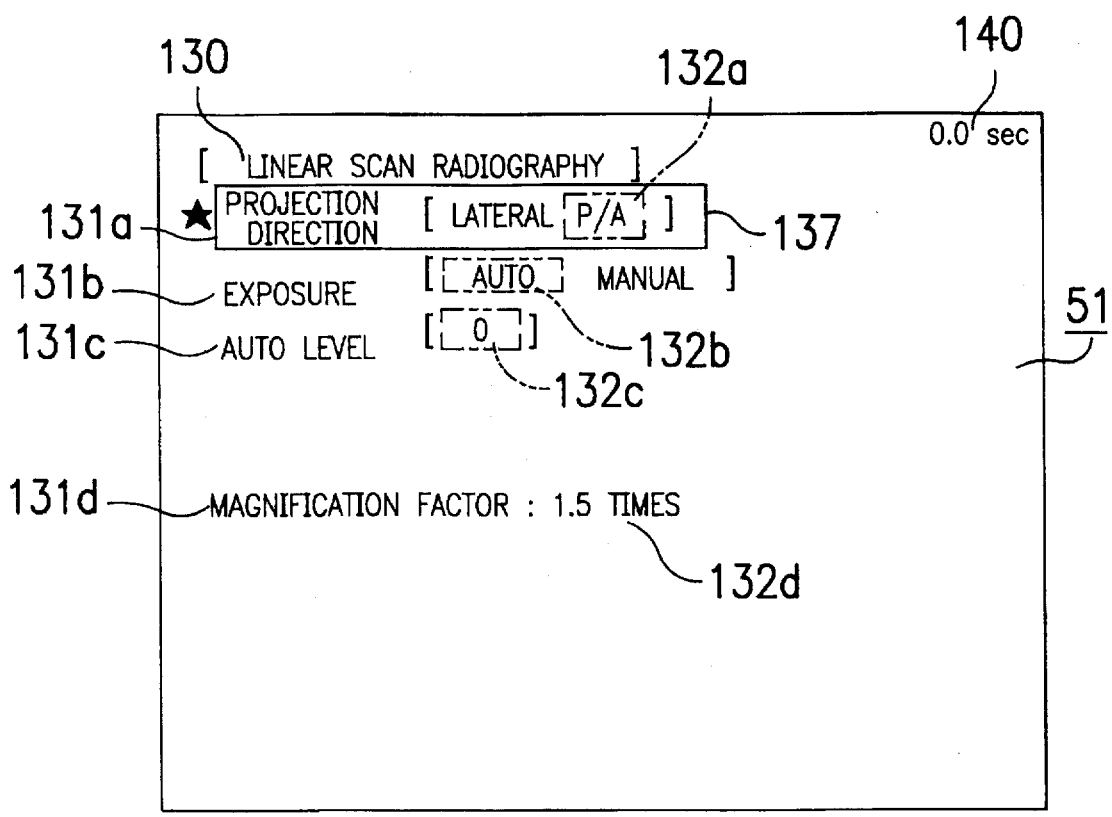
FIG. 42 is a diagram showing display data of the display unit 51 when the projection direction is set in the front direction in skull linear scanning radiography.

FIG. 41 is a diagram showing an imaging region 153 when the projection direction is set in the P/A direction in skull linear scan radiography, and FIG. 42 is a diagram showing display data of the display unit 51 when the projection direction is set in the P/A direction in skull linear scan radiography. In the projection direction P/A radiography, meanwhile, only the manipulation of the operation panel 19 is different, and the radiographic procedure is the same as the radiographic procedure shown in FIG. 40. In the skull linear scan radiography, when the projection direction is P/A, a projection image from the posterior to the anterior side of the head of the patient is obtained. The operation procedure of the operation panel 19 is described. First, by pressing the "linear scan" key 60, the "linear scan radiography" is displayed in the radiographic mode display region 130 of the display unit 51, and the frame display 137 is displayed in the setting condition "projection direction."

At this time, to change the parameter from lateral to P/A, the right cursor key 73 is pressed, and the cursor 183 is moved from "lateral" to "P/A." By pressing the down cursor key 71, the frame display 137 is moved to the next setting condition "exposure," and its parameter is selected in "auto" or "manual." By further pressing the down cursor key 71, the frame display 137 is moved to the next setting condition "auto level," and the parameter is set in one of the nine stages from 4 to −4. In this case, too, the magnification factor is set at 1.5 times.

After thus setting the radiographic conditions through the operation panel, in the same radiographic procedure as shown in the flow chat in FIG. 40, preparation for radiography and positioning of the patient are conducted, and the irradiation button 47 is pressed, thereby finishing the radiographic operation.

The temporomandibular joint distance measuring linear tomography is described below. In this radiography, as shown in Table 5, temporomandibular joint distance measuring linear tomography and temporomandibular joint head angle measuring linear tomography, which are individually described below.

stages at one-step increments in a range of 0 to 9. When the patient size is set at, for example, 5, "76 kV" is displayed in the parameter display region 132b of the next setting condition "tube voltage," and "9 mA" is displayed in the parameter display region 132c of the next setting condition "tube current." The tube voltage and tube current can be either increased or decreased by the let cursor key 72 and right cursor key 73. The next setting condition "tomo width" is preset to be 9 mm.

Referring now to FIG. 45, the operation procedure will be described. First at step j1, the film cassette 21 is loaded into the other end 1b of the swivel arm 1. This film cassette 21 contains an X-ray film 92 shown in FIG. 6E. At step j2, it is confirmed that the chin rest 17 is at the lowest position, and it is confirmed at step j3 that the ready lamp 45 is lighted. At step j4, the slit plate 22 is changed over to the broad slit 91 in FIG. 5B. At step j5, it is checked that the arrow 134 of the ascending/descending main body 2 is matched with value 0 of the graduation 135 of the patient frame 3, and the jaw bone plate is removed at step j6 and is replaced by the ear rods 29, 30.

When the preparation for radiography is thus over, at step j7 the patient is seated on the chair 6, and the ascending/

TABLE 5

Figure 43:
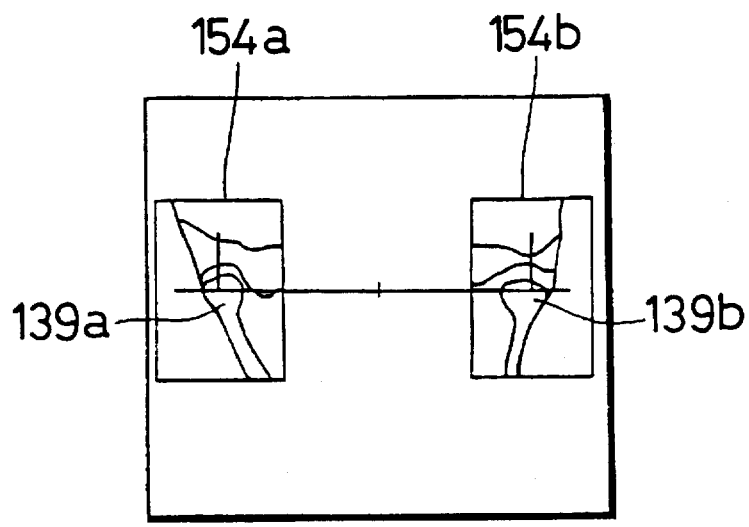
FIG. 43 is a diagram showing imaging regions 154a, 154b in temporomandibular joint distance measuring purpose linear tomography.
Figure 46:
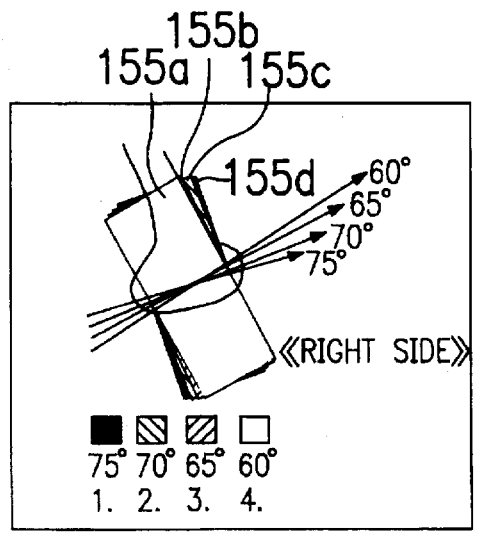
FIG. 46 is a diagram showing imaging regions 155a–155d by temporomandibular joint head angle measuring purpose linear tomography.

| RADIOGRAPH TYPE | PANORAMA FOR AREA SELECTION | KEY SELECTION | RADIOGRAPHIC CONDITION SETTING ON OPEARTION PANEL EXPOSURE | PATIENT POSITIONING REFEREMCE PLANE POSITIONING | PATIENT REST | |
|---|---|---|---|---|---|---|
| TEMPOROMANDIBULAR JOINT MEASURING PURPOSE LINEAR RADIOGRAPHY | FIG. 43<br><br>FIG. 46 | NOT REQUIRED | "JOINT DISTANCE" KEY 66<br>"JOINT ANGLE" KEY 67 | DEPENDENT ON PATIENT SIZE | EYE-EAR PLANT | EAR ROD | CHIN REST |

| RADIOGRAPH TYPE | | PATIENT POSITIONING IRRADIATION FIELD BEAM | TOMOGRAPHIC BEAM | SECOND SLIT SELECTION | X-RAY FILM (SENSITIZED PAPER) SELECTION |
|---|---|---|---|---|---|
| TEMPOROMANDIBULAR JOINT MEASURING PURPOSE LINEAR RADIOGRAPHY | FIG. 43<br>FIG. 46 | HIGHEST POSITION OF IRRADIATION FIELD | APPARATUS MOVES AUTOMATICALLY | FIG. 5B | FIG. 6E<br>FIG. 6D |

Figure 44:
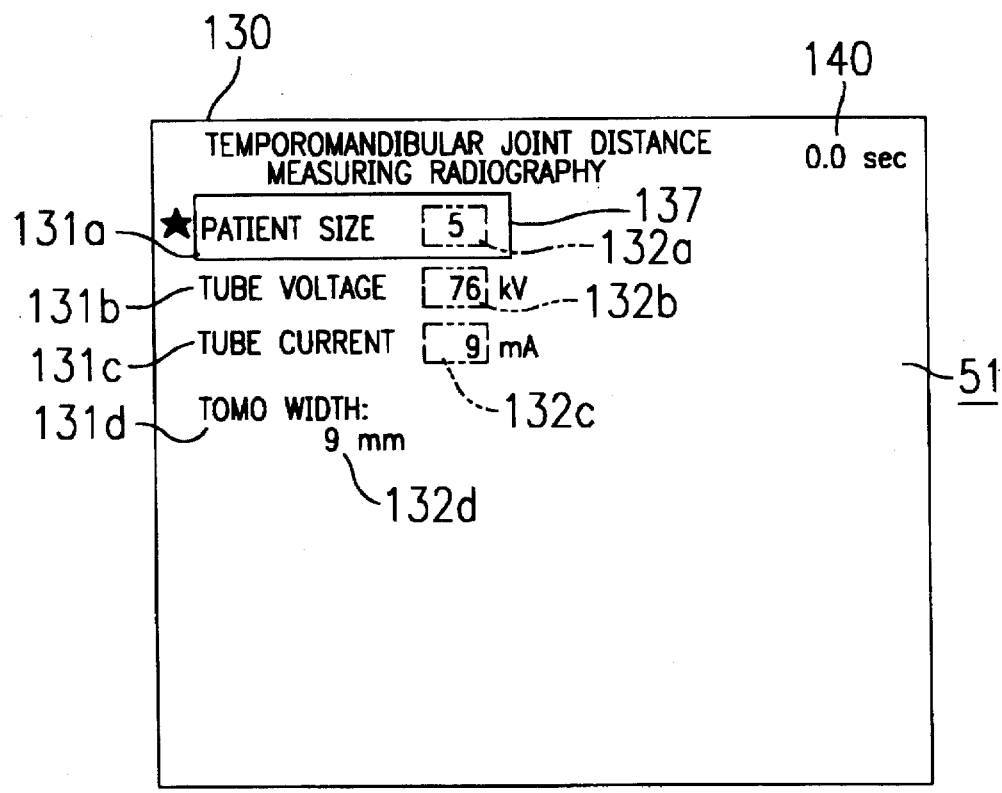
FIG. 44 is a diagram showing display data of the display unit 51 of temporomandibular joint distance measuring purpose linear tomography.

FIG. 43 is a diagram showing imaging regions 154a, 154b in temporomandibular joint distance measuring linear tomography, FIG. 44 is a diagram showing display data of the display unit 51 of temporomandibular joint distance measuring linear tomography, and FIG. 45 is a flow chart for explaining the operation procedure of temporomandibular joint distance measuring linear tomography. In this radiography, tomographs near the right and left temporomandibular joints 139a, 139b are obtained. From these images, the distance L between the both temporomandibular joints 139a, 139b is the distance between the temporomandibular joints. The operation procedure of the operation panel 19 is described. First, when the "temporomandibular joint distance" key 66 is pressed, the "temporomandibular joint distance measuring radiography" is displayed in the radiographic mode display region 130 of the display unit 51, and the frame display 131 is displayed in the setting condition "patient size." The parameter of patient size can be set by the left cursor key 72 and right cursor key 73 out of ten descending main body 2 is moved at step j8 to adjust the height of the ear rod 20, 30 to the ear holes of the patient. The patient is brought into the radiographic position at step j9. At step j10, the chin rest 17 is raised to put the jaw of the patient on, the patient occludes spontaneously at step j11, the median line beam 34 is adjusted at step j12, and the ear rods 29, 30 are inserted into the ear holes at step j13 to fix the patient. At step j14, the eye-ear plane is adjusted to the eye-ear horizontal beam 33, the patient frame 3 is fixed by the lock handle 9 at step j15, the ascending/descending main body 2 is moved at step j16 to adjust the irradiation field beam to the highest position of the irradiation field, and it is confirmed again at step j17 that the ready lamp 45 is lighted. The irradiation button 47 is pressed at step j18 to start radiography. When the radiography is over, at step j19, the swivel arm is returned to home position, and the film cassette 21 is moved at step j20 to finish the radiographic operation.

Figure 47:
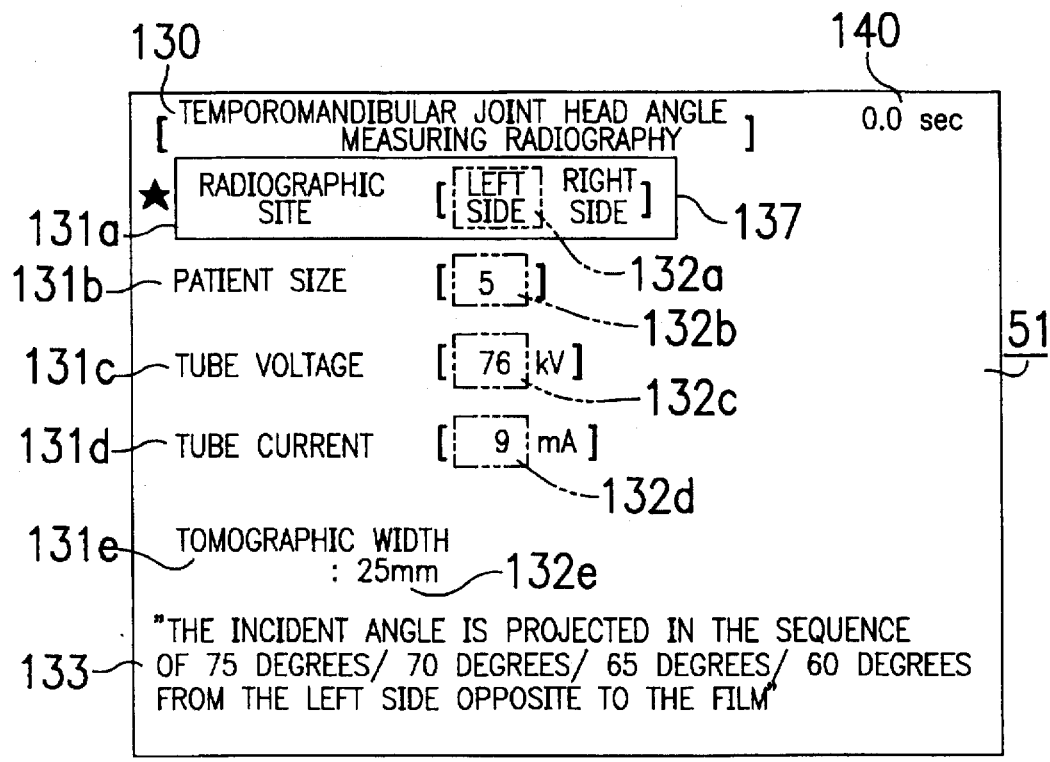
FIG. 47 is a diagram showing display data of the display unit 51 of temporomandibular joint head angle measuring purpose linear tomography.

FIG. 46 is a diagram showing imaging regions 155a to 155d by temporomandibular joint head angle measuring linear tomography, and FIG. 47 is a diagram showing display data of the display unit 51 of temporomandibular joint head angle measuring linear tomography. The radiographic procedure is same as in the temporomandibular joint distance measuring linear radiography, and hence the explanation is omitted by referring to FIG. 45. In this temporomandibular joint head angle measuring linear radiography, the predetermined angle, that is, the projection angle is set at four angles, 60 degrees, 65 degrees, 70 degrees, and 75 degrees, so that the image of the taken temporomandibular joint 139 is obtained. The operating procedure of the operation panel 19 is described below. First, by pressing the "joint head angle" key 67, the "temporomandibular joint head angle measuring radiography" is displayed in the radiographic mode display region 130 of the display unit 51, and the frame display 137 is displayed in the setting condition "radiographic site." The parameter of the setting site is selected by the left cursor key 72 and right cursor key 73, and either "left side" or "right side" is selected. By pressing the down cursor key 71, the frame display 137 is moved to the next setting condition "patient size," and the parameter is similarly selected out of ten stages of a range from 0 to 9 by one stage depending on the patient size. At this time, when the patient size is selected at 5, as mentioned above, the tube voltage is set at 76 kV and the tube current is set at 9 mA. The tube voltage and tube current can be increased or decreased by the left cursor key 72 or right cursor key 73. The tomographic width is preset at 25 mm, and in order to support the radiographic state by displaying the radiographic related information such as projection angle in the lower display region 133 of the display unit 51, the statement is displayed, "The incident angle is projected in the sequence of 75 degrees/70 degrees/65 degrees/60 degrees from the left side opposite to the film."

After thus setting the radiographic conditions on the operation panel 19, the temporomandibular joint head angle measuring linear radiography is performed in the same procedure as the flow chart in FIG. 45. The images obtained by this taking are four X-ray images 93d at 75 degrees, 70 degrees, 65 degrees, and 60 degrees on the X-ray film 92 in FIG. 6D.

Figure 48:
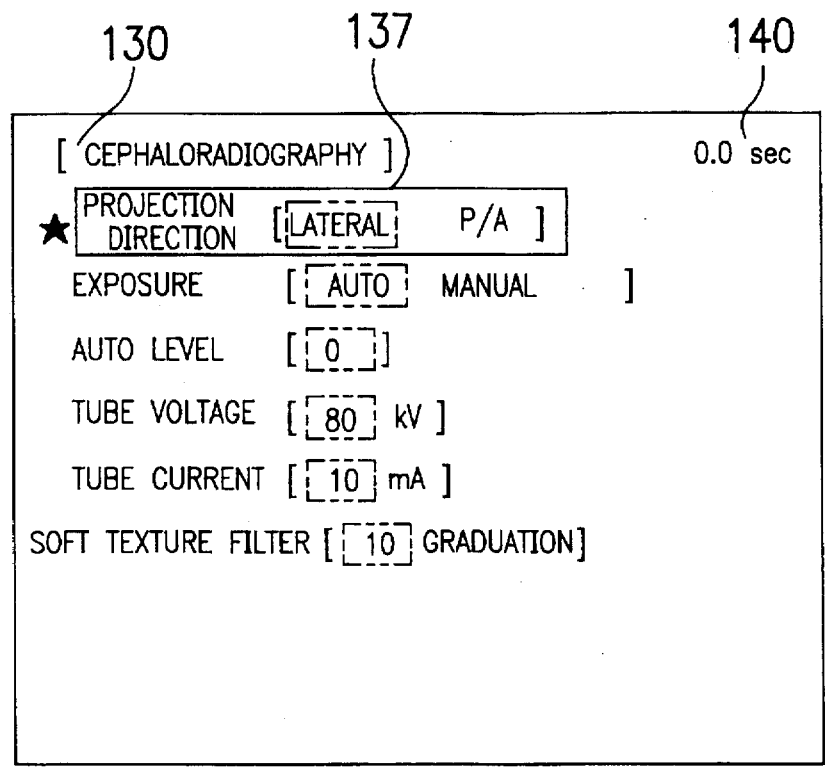
FIG. 48 is a diagram showing display data of the display unit 51 when the projection direction is set in the lateral side in cephaloradiography.

FIG. 48 is a diagram showing display data of the display unit 51 when the projection direction is set in the lateral side in cephaloradiography. In cephaloradiography, the projection direction is set at either lateral or P/A (front). In the case of lateral projection direction, the operating procedure of the operation panel is as follows. First, when the "cephalo" key 61 is pressed, the "cephaloradiography" is displayed in the radiographic mode display region 130 of the display unit 51, and the frame display 137 is displayed in the setting condition "projection direction," and the parameter of the radiographic direction is selected at "lateral" out of "lateral" and "P/A." When the down cursor key 71 is pressed, the frame display 137 is moved to the next setting condition "exposure," and the parameter is set at either "auto" or "manual." The down cursor key 71 is further pressed to move the frame display 137 to the setting condition "auto level," and when "auto" has been selected in the previous operation, the level is set out of nine stages at one-step increments in a range of 4 to −4. The remaining setting condition "tube voltage" is preset at 80 kV, and the "tube current" is preset at 10 mA. Meanwhile, the "soft texture filter" is preset at 16, and this numerical value can be set at a desired graduation suited to the patient in 23 stages at one-step increments in a range of 8 to 30. When the "manual" mode is selected in the setting condition "exposure," the exposure time is automatically displayed as "0.3" in the exposure time display region 140 in the upper right corner of the screen, and this exposure time can be set by the left cursor key 72 and right cursor key 73 in 21 stages at every 0.1 sec in a range from 0.3 to 4.0.

Figure 49:
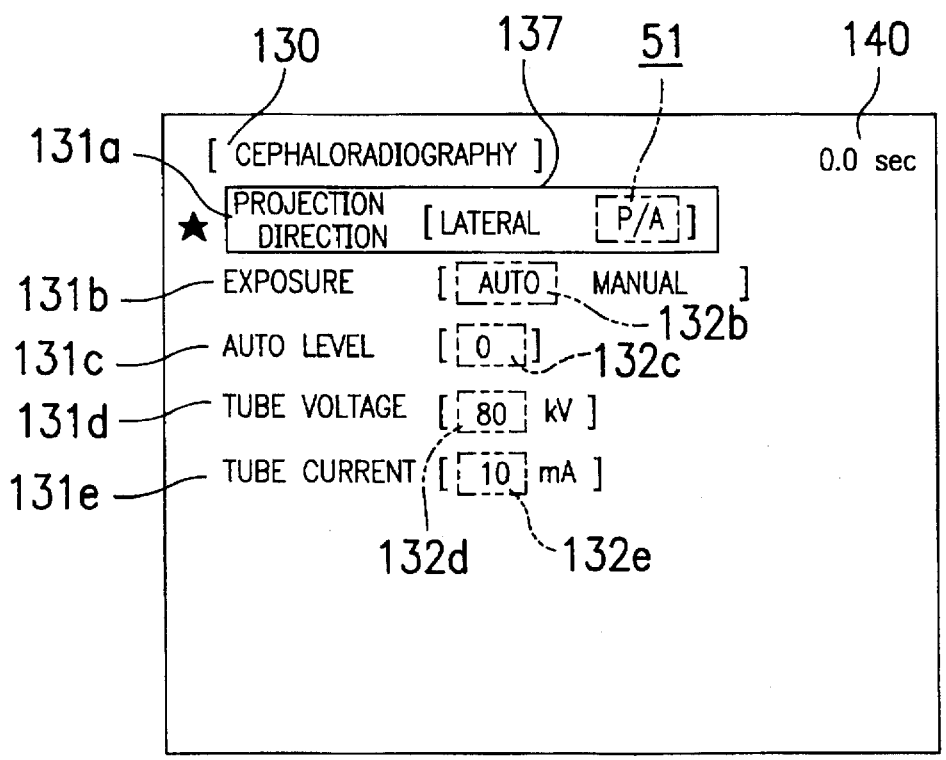
FIG. 49 is a diagram showing display data of the display unit 51 when the projection direction is set in the lateral side in cephaloradiography.
Figure 50:
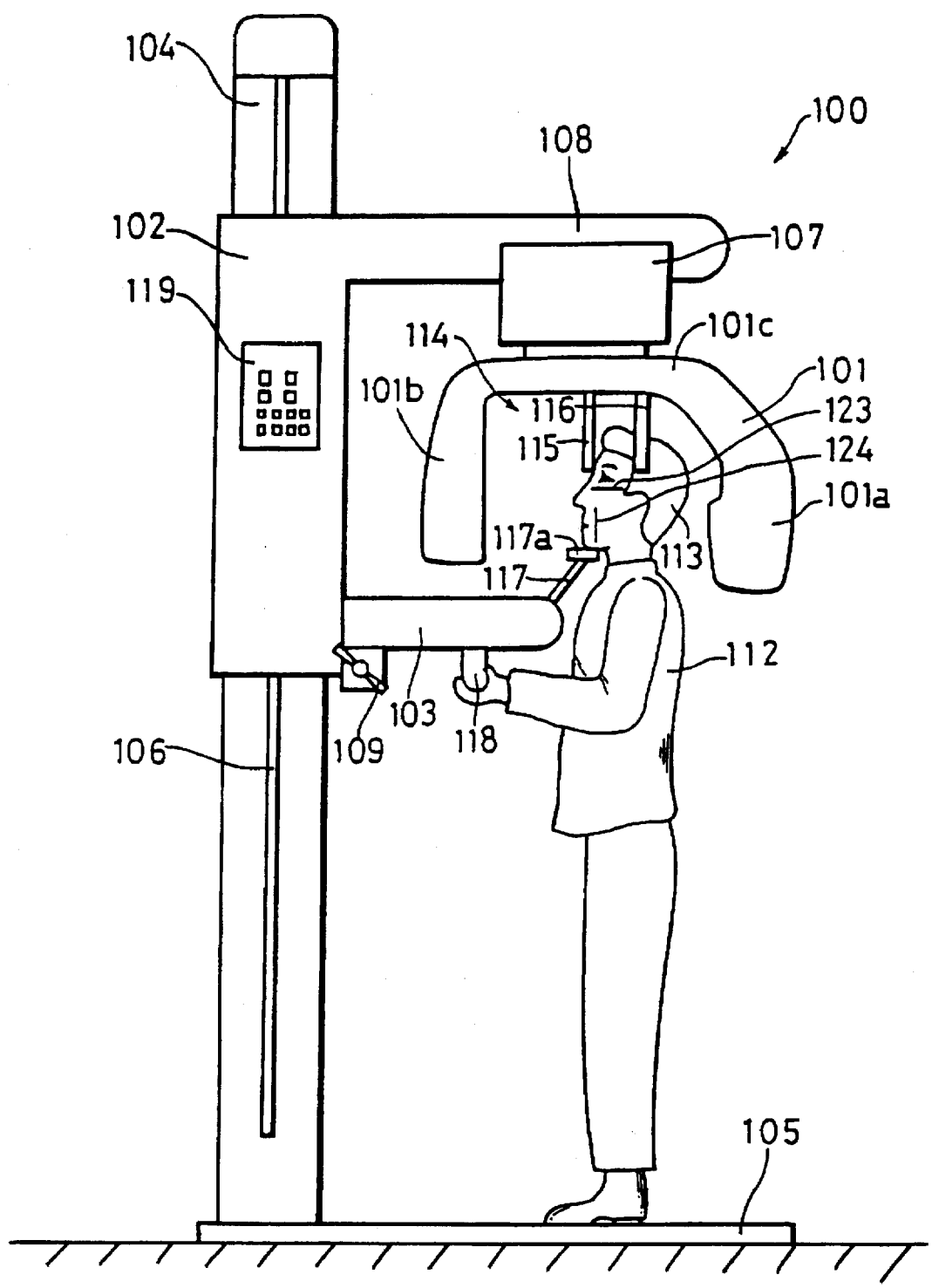
FIG. 50 is a side view showing a conventional radiographic apparatus 100.
Figure 51:
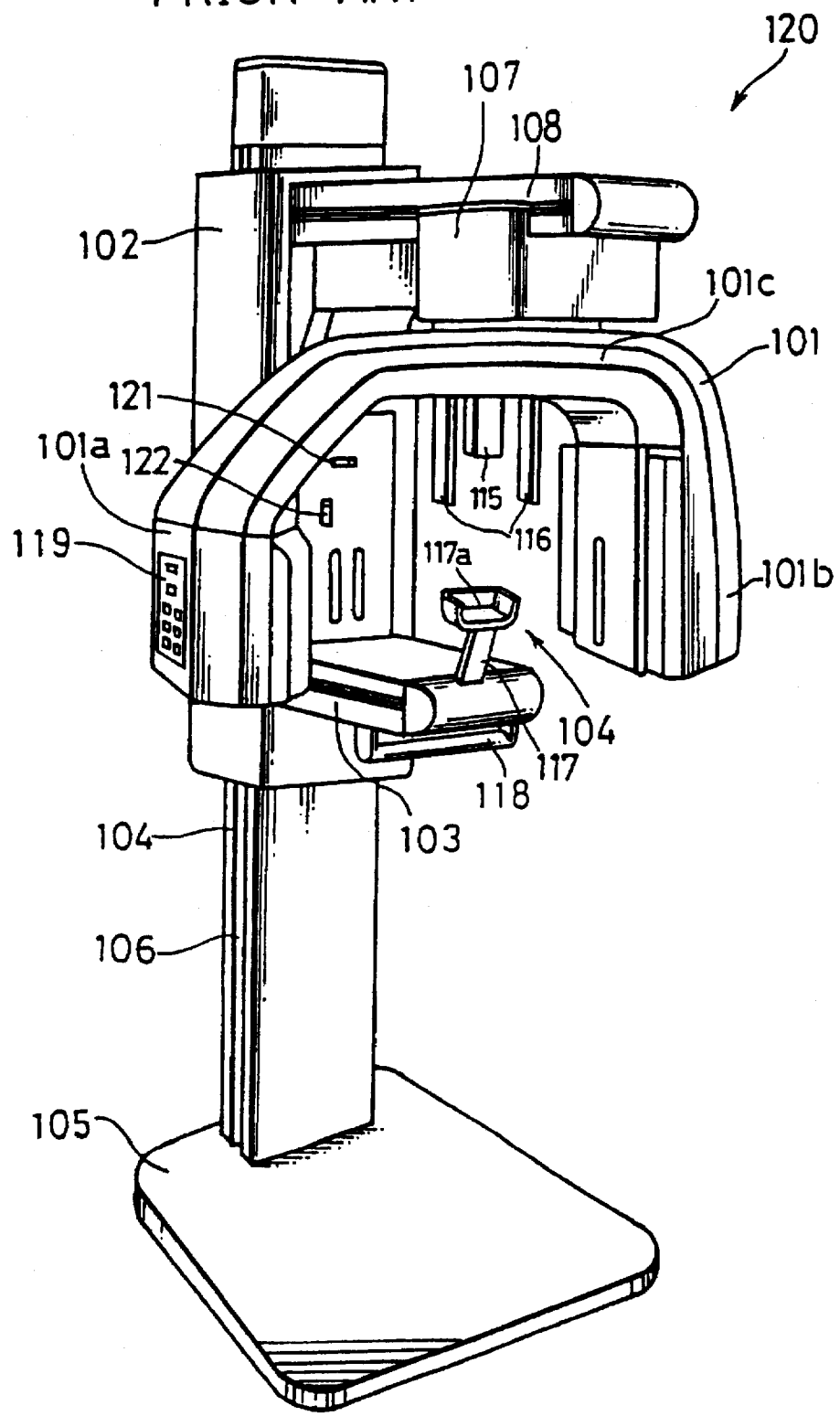
FIG. 51 is a perspective view showing other conventional radiographic apparatus 120.

FIG. 49 is a diagram showing display data of the display unit 51 when the projection direction is set in the P/A side in cephaloradiography. In this radiography, it can be set by changing the setting condition "projection direction" from "lateral" to "P/A" by using the right cursor key 73, and the remaining setting conditions "exposure,""auto level," "tube voltage," and "tube current" can be set same as in the lateral radiography. In this radiography, however, the setting condition about the "soft texture filter" in the lateral radiography is not display.

Thus, the plural radiographic modes, that is, dentition standard panoramic radiography, dentition magnified panoramic radiography, maxillary sinus panoramic radiography, jaw bone and dentition cross sectional linear tomography, maxillary sinus linear tomography, jaw bone and dentition parallel plane linear tomography, temporomandibular joint frontal linear tomography, temporomandibular lateral linear tomography, maxillary sinus scanogram radiography, temporomandibular joint scanogram radiography, temporomandibular joint distance measuring linear tomography, temporomandibular joint head angle measuring linear tomography, and cephaloradiography, are set by plural keys 52, 55–61, 66–69, and plural setting conditions corresponding to the radiographic mode selected by one of these keys 52, 55–61, 66–69 are displayed on one screen, and are sequentially selected by the up cursor key and down cursor key 70, 71, and hence parameters of the setting conditions can be set by left cursor key 72 and right cursor key 73. Moreover, by pressing "memory" key 74, the set radiographic conditions can be stored, and hence it is not necessary to set again, and the labor of setting operation can be saved. Moreover, since plural setting conditions and their parameters are displayed on one screen, a wrong input of parameter can be easily corrected, and the desired program can be entered by the so-called interactive system with the apparatus, without having to refer to the manual or code table used in the prior art.

In the foregoing embodiments, the liquid crystal display element is used as the display means 63, but the liquid crystal display element may be also replaced by the cathode ray tube (CRT), plasma display tube, electroluminescence (EL), etc.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and the range of equivalency of the claims are therefore intended to be embraced therein.

What is claimed is:

1. A radiographic apparatus comprising:
   a base;
   a post standing up on the base;
   an ascending/descending main body provided on the post so as to be free to move up and down;
   a swivel arm in which an X-ray source and detecting means for detecting X-rays radiated from the X-ray source are arranged so as to confront each other;
   swivel and driving means for moving and driving the swivel arm along a desired track, the swivel and driving means being interposed between the ascending/descending main body and the swivel arm;

holding means for positioning and holding a head of a patient at a desired radiographic position between the X-ray source and the detecting means;

a support frame, provided on and depended from the ascending/descending main body, for supporting the holding means, to which the holding means is attached; and an operation panel for inputting radiographic conditions, collectively disposed on an upper part of the support frame, the operation panel including input means for entering input information which determines the radiographic conditions as well as display means for displaying information which aids the input operation by the input means, and wherein:

the input means comprises selection means for selecting any one of a plurality of predetermined radiographic modes, means for selecting setting conditions of the radiographic mode selected by the radiographic mode selection means, and means for inputting parameters of the setting conditions selected by the setting conditions selection means; and the display means includes a display region to display the radiographic mode selected by the radiographic mode selection means, a display region to display the setting conditions of the radiographic mode displayed in the radiographic mode displaying region; a display region to display the parameters of the setting conditions displayed in the setting conditions display region, and a display region to schematically display in figures and characters information related to radiography, said information including desired radiographic position thereof, projection angle of said X-ray source, and tomographic shape, and the display means displays a plurality of tomographic position display lines of a radiographic site and each of said display lines moves the radiographic site in response to the parameters of the setting conditions selected by the setting conditions selection means.

2. The radiographic apparatus of claim 1, wherein the display means varies an interval between the respective tomographic position display lines.

3. The radiographic apparatus of claim 1, wherein a plurality of radiographic modes selected by the radiographic mode selection means comprise at least panoramic radiographic, jaw bone/dentition cross sectional tomography, dentition parallel tomography, maxillary sinus tomography, frontal direction temporomandibular joint tomography, temporomandibular temporal tomography, temporomandibular joint head angle measuring radiography, maxillary sinus scanogram filming, temporomandibular joint scanogram filming, linear scanning radiography, and cephaloradiography.

4. The radiographic apparatus of claim 1, wherein the input means comprises a nonvolatile memory for storing the radiographic mode, setting conditions and parameters set by the radiograpic mode selection means, setting condition selection means, and parameter setting means, respectively.

5. The radiographic apparatus of claim 4, wherein the display means possesses a region for schematically displaying the information related to radiography, including the radiographic position, projection angle, and tomographic mode, in figures and characters.

* * * * *